US012617801B2

(12) United States Patent
Carzaniga et al.

(10) Patent No.: US 12,617,801 B2
(45) Date of Patent: May 5, 2026

(54) TETRAHYDROTHIENO PYRIDINE DERIVATIVES AS DDRS INHIBITORS

(71) Applicant: CHIESI FARMACEUTICI S.P.A., Parma (IT)

(72) Inventors: Laura Carzaniga, Parma (IT); Fabio Rancati, Parma (IT); Andrea Rizzi, Parma (IT); Keith Christopher Knight, Parma (IT); Anna Karawajczyk, Parma (IT); Barbara Karolina Wołek, Parma (IT); Toby Matthew Grover Mullins, Parma (IT); Ben Paul Whittaker, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 416 days.

(21) Appl. No.: 18/283,867

(22) PCT Filed: Mar. 25, 2022

(86) PCT No.: PCT/EP2022/057940

§ 371 (c)(1),
(2) Date: Sep. 25, 2023

(87) PCT Pub. No.: WO2022/200578

PCT Pub. Date: Sep. 29, 2022

(65) Prior Publication Data

US 2024/0199635 A1 Jun. 20, 2024

(30) Foreign Application Priority Data

Mar. 26, 2021 (EP) .................................... 21165284

(51) Int. Cl.

| | |
|---|---|
| ***C07D 495/04*** | (2006.01) |
| ***A61K 31/444*** | (2006.01) |
| ***A61K 31/496*** | (2006.01) |
| ***A61K 31/497*** | (2006.01) |
| ***A61K 31/506*** | (2006.01) |
| ***A61K 31/541*** | (2006.01) |

(52) U.S. Cl.

CPC .......... *C07D 495/04* (2013.01); *A61K 31/444* (2013.01); *A61K 31/496* (2013.01); *A61K 31/497* (2013.01); *A61K 31/506* (2013.01); *A61K 31/541* (2013.01)

(58) Field of Classification Search

CPC .. C07D 495/04; A61K 31/444; A61K 31/496; A61K 31/497; A61K 31/506; A61K 31/541

USPC ...................................................... 514/227.8

See application file for complete search history.

(56) References Cited

FOREIGN PATENT DOCUMENTS

| | | | |
|---|---|---|---|
| CN | 104490889 | A | 4/2015 |
| CN | 107206004 | A | 9/2017 |
| CN | 107849044 | A | 3/2018 |
| CN | 108558848 | A | 9/2018 |
| CN | 111295386 | A | 6/2020 |
| CN | 117157300 | A | 12/2023 |
| JP | 2003073357 | A | 3/2003 |
| JP | 2018502900 | A | 2/2018 |
| JP | 2018519317 | A | 7/2018 |
| KR | 1020200087922 | A | 7/2020 |
| RU | 2625799 | C2 | 7/2017 |
| WO | WO-1999021617 | A2 | 5/1999 |
| WO | WO-2001098290 | A2 | 12/2001 |
| WO | WO-2016026372 | A1 | 2/2016 |
| WO | WO-2016064970 | A1 | 4/2016 |
| WO | WO-2017005583 | A1 | 1/2017 |
| WO | WO-2018221433 | A1 | 12/2018 |

OTHER PUBLICATIONS

English translation of the Combined Russian Office Action and Search Report received on Jul. 29, 2025, in corresponding Russian Patent Application No. 2023127301, 14 pages.

English translation of the Combined Chinese Office Action and Search Report issued Aug. 8, 2025, received on Sep. 4, 2025, in corresponding Chinese Patent Application No. 202280024330.7, 7 pages.

European Search Report issued Sep. 8, 2021 in Patent Application No. EP21165284, 2 pages.

International Search Report issued Jul. 4, 2022 in PCT/EP2022/057940, 3 pages.

*Primary Examiner* — Kristin A Vajda

(74) *Attorney, Agent, or Firm* — Element IP, PLC

(57) ABSTRACT

The present invention relates to compounds of general formula (I) inhibiting Discoidin Domain Receptors (DDR inhibitors), methods of preparing such compounds, pharmaceutical compositions containing them and therapeutic use thereof. The compounds of the invention may be useful for instance in the treatment of many disorders associated with DDR mechanisms.

(I)

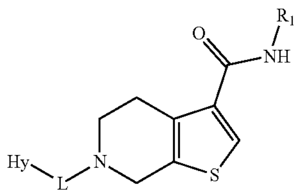

15 Claims, No Drawings

TETRAHYDROTHIENO PYRIDINE DERIVATIVES AS DDRS INHIBITORS

FIELD OF THE INVENTION

The present invention relates to compounds inhibiting Discoidin Domain Receptors (DDR inhibitors), methods of preparing such compounds, pharmaceutical compositions containing them and therapeutic use thereof.

The compounds of the invention may be useful for instance in the treatment of many disorders associated with DDR mechanisms.

BACKGROUND OF THE INVENTION

Discoidin Domain Receptors (DDRs) are type I transmembrane receptor tyrosine kinase (RTKs). The DDR family comprises two distinct members, DDR1 and DDR2.

DDRs are unique receptors among the other members of the RTK superfamily, in that DDRs are activated by collagen whereas other members of the RTK superfamily are typically activated by soluble peptide-like growth factors (see Vogel, W. (1997) Mol. Cell 1, 13-23; Shrivastava A. Mol Cell. 1997; 1:25-34). Moreover, DDRs are unusual RTKs also because they form ligand-independent stable dimers that are non-covalently linked (see Noordeen, N. A. (2006) J. Biol. Chem. 281, 22744-22751; Mihai C. J Mol Biol. 2009; 385:432-445).

The DDR1 subfamily is composed of five membrane-anchored isoforms, and the DDR2 subfamily is represented by a single protein. The five DDR1 isoforms all have in common the extracellular and transmembrane domains but differ in the cytoplasmic region (see Valiathan, R. R. (2012) Cancer Metastasis Rev. 31, 295-321; Alves, F. (2001) FASEB J. 15, 1321-1323).

DDR receptor family has been found involved in a series of fibrotic diseases, such as pulmonary fibrosis, and in particular idiopathic pulmonary fibrosis (IPF). The first evidence for a protective role of DDR1 deletion in lung fibrosis was generated in 2006 by the research group of Dr. Vogel (see Avivi-Green C, Am J Respir Crit Care Med 2006; 174:420-427). The authors demonstrated that DDR1-null mice were largely protected against bleomycin (BLM)-induced injury. Furthermore, myofibroblast expansion and apoptosis were much lower in these animals compared with their wild-type counterparts. Absence of inflammation in knockout mice was confirmed by lavage cell count and cytokines ELISA. These results indicated that DDR1 expression is a prerequisite for the development of lung inflammation and fibrosis.

DDR2 deficiency or downregulation reduces bleomycin-induced lung fibrosis (see Zhao H, Bian H, Bu X, Zhang S, Zhang P, Yu J, et al Mol Ther 2016; 24:1734-1744). Zhao et al, demonstrated that DDR2 plays a critical role in the induction of fibrosis and angiogenesis in the lung, in particular that DDR2 synergizes with transforming growth factor (TGF)-β to induce myofibroblast differentiation. Furthermore, they showed that treatment of injured mice with specific siRNA against DDR2 exhibited therapeutic efficacy against lung fibrosis. In a second publication, Jia et al showed that mice lacking DDR2 are protected from bleomycin-induced lung fibrosis (see Jia S, Am J Respir Cell Mol Biol 2018; 59:295-305. In addition, DDR2-null fibroblasts are significantly more prone to apoptosis than wild-type fibroblasts, supporting a paradigm in which fibroblast resistance to apoptosis is critical for progression of fibrosis.

Some compounds have been described in the literature as DDR1 or DDR2 antagonists.

WO2016064970 (Guangzhou) discloses tetrahydroisoquinoline-7-carboxamides as selective DDR1 inhibitors useful as therapeutic agents for preventing and treating inflammation, liver fibrosis, kidney fibrosis, lung fibrosis, skin scar, atherosclerosis and cancer.

Of note, antagonizing the DDR receptors may be useful for the treatment of fibrosis and disease, disorder and conditions that result from fibrosis and even more antagonizing both receptors DDR1 and DDR2 may be particularly efficacious in the treatment of the above-mentioned disease, disorder and conditions.

Several efforts have been done in the past years to develop novel DDR1 and DDR2 receptor antagonists useful for the treatment of several disease and some of those compounds have shown efficacy also in humans.

Despite the above cited prior art, there remains a potential for developing selective inhibitors of both receptors DDR1 and DDR2 useful for the treatment of diseases or conditions associated with a dysregulation of DDR receptors, in the respiratory field, in particular idiopathic pulmonary fibrosis (IPF), to be administered by the inhalation route and characterized by a good inhalatory profile, that corresponds to a good activity in the lung, a good lung retention and to a low metabolic stability in order to minimize the systemic exposure and correlated safety issues.

In this direction, we have surprisingly found a new series of compounds of general formula (I), as herein below reported, that solves the problem of providing inhibitors for receptors DDR1 and DDR2 for administration by inhalation, that are active as selective inhibitors of DDR1 and DDR2 receptors with respect to other human protein kinases. These compounds show high potency, good inhalatory profile, low metabolic stability, low systemic exposure, improved safety and tolerability.

SUMMARY OF THE INVENTION

In a first aspect the present invention relates to a compound of formula (I)

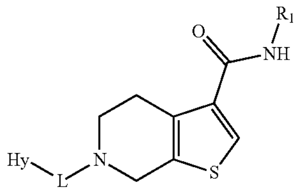

(I)

wherein

L is selected from the group consisting of —C(O)— and —$CH_2$—;

Hy is a monocyclic heteroaryl optionally substituted with one or more groups selected from —($C_1$-$C_4$)alkyl, halogen atoms, cyano, —$(CH_2)_n NR_4R_5$, —NH-heterocycloalkyl, —O—($C_1$-$C_6$)alkyl, —($C_1$-$C_6$)haloalkyl, —C(O)NH—($C_1$-$C_6$)alkylene-$NR_4R_5$, —O—($C_1$-$C_6$) alkylene-cycloalkyl, —NHC(O)—($C_1$-$C_6$)alkyl, —NHC(O)—($C_1$-$C_6$)alkylene-$NR_4R_5$, —NHC(O)—($C_1$-$C_6$)alkylene-O—($C_1$-$C_4$)alkyl, —NH—($C_1$-$C_6$)alkylene-O—($C_1$-$C_4$)alkyl, —NH—($C_1$-$C_6$)alkylene-OH, -heteroaryl optionally substituted by one or more —($C_1$-$C_4$)alkyl, —NH— heteroaryl, wherein said heteroaryl is optionally substituted by one or more —$(C_1-C_4)$alkyl, and heterocycloalkyl optionally substituted by one or more groups selected from oxo and —$(C_1-C_6)$alkyl;

$R_1$ is selected from the group consisting of:

Het which is an heteroaryl optionally substituted with one or more groups selected from —$(C_1-C_4)$alkyl, —$(C_1-C_4)$haloalkyl and aryl, wherein said aryl is optionally substituted with one or more groups selected from —$(C_1-C_4)$alkyl and halogen atoms; and

X (X)

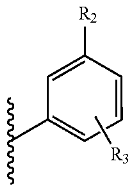

wherein $R_2$ is selected from the group consisting of —$O(C_1-C_4)$ haloalkyl, halogen atoms, —$O(C_3-C_7)$cycloalkyl and —$(C_1-C_4)$haloalkyl;

$R_3$ is H or is selected from the group consisting of halogen atoms, cyano, —$O(C_1-C_4)$alkyl, —$O(C_1-C_4)$haloalkyl, heterocycloalkyl-$(C_1-C_4)$alkylene-, —$(C_1-C_4)$alkylene-heterocycloalkyl-$NR_4R_5$, and heteroaryl optionally substituted with one or more —$(C_1-C_4)$ alkyl, and wherein said heterocycloalkyl is optionally substituted with one or more —$(C_1-C_4)$alkyl;

n is 0, 1 or 2;

$R_4$ is H or —$(C_1-C_4)$alkyl;

$R_5$ is H or —$(C_1-C_4)$alkyl;

and pharmaceutically acceptable salts thereof.

In a second aspect, the invention refers to a pharmaceutical composition comprising a compound of formula (I) and pharmaceutically acceptable salts thereof in a mixture with one or more pharmaceutically acceptable carrier or excipient.

In a third aspect, the invention refers to a compound of formula (I) and pharmaceutically acceptable salts or to a pharmaceutical composition comprising a compound of formula (I) and pharmaceutically acceptable salts thereof for use as a medicament.

In a further aspect, the invention refers to a compound of formula (I) and pharmaceutically acceptable salts thereof or to a pharmaceutical composition comprising a compound of formula (I) and pharmaceutically acceptable salts thereof for use in preventing and/or treating a disease, disorder or condition associated with dysregulation of DDR.

In a further aspect, the invention refers to a compound of formula (I) and pharmaceutically acceptable salts thereof or to a pharmaceutical composition comprising a compound of formula (I) and pharmaceutically acceptable salts thereof for use in the prevention and/or treatment of fibrosis and/or diseases, disorders, or conditions that involve fibrosis.

In a further aspect, the invention refers to a compound of formula (I) and pharmaceutically acceptable salts thereof or to a pharmaceutical composition comprising a compound of formula (I) and pharmaceutically acceptable salts thereof for use in the prevention and/or treatment of idiopathic pulmonary fibrosis (IPF).

DETAILED DESCRIPTION OF THE INVENTION

Definitions

Unless otherwise specified, the compound of formula (I) of the present invention is intended to include also its stereoisomers or pharmaceutically acceptable salts thereof.

Unless otherwise specified, the compound of formula (I) of the present invention is intended to include also the compounds of formula (Ia), (Iaa), (Iaa'), (Iaa"), (Iab), (Ib), (Iba) and (Ibb).

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "stereoisomer" refers to isomers of identical constitution that differ in the arrangement of their atoms in space. Enantiomers and diastereomers are examples of stereoisomers.

The term "enantiomer" refers to one of a pair of molecular species that are mirror images of each other and are not superimposable.

The term "diastereomer" refers to stereoisomers that are not mirror images.

The term "racemate" or "racemic mixture" refers to a composition composed of equimolar quantities of two enantiomeric species, wherein the composition is devoid of optical activity.

The term "halogen" or "halogen atoms" or "halo" as used herein includes fluorine, chlorine, bromine, and iodine atom.

The term "$(C_x-C_y)$alkyl" wherein x and y are integers, refers to a straight or branched chain alkyl group having from x to y carbon atoms. Thus, when x is 1 and y is 4, for example, the term comprises methyl, ethyl, n-propyl, isopropyl, n-butyl, isobutyl, sec-butyl, and t-butyl.

The term "$(C_x-C_y)$alkylene" wherein x and y are integers, refers to a bivalent saturated aliphatic chain derived from an alkane by removal of two hydrogen atoms from different carbon atoms, having from x to y carbon atoms, e.g. methylenyl.

The term "$O(C_x-C_y)$haloalkyl" wherein x and y are integers, refers to the above defined "$(C_x-C_y)$haloalkyl" groups wherein a carbon atom is linked to an oxygen atom.

Examples of said "$O(C_x-C_y)$haloalkyl" groups may thus include halogenated, poly-halogenated and fully halogenated Oalkyl groups wherein all hydrogen atoms are replaced by halogen atoms, e.g. trifluoromethoxy and difluoromethoxy.

The term "$(C_x-C_y)$alkylene-$NR_{x'}R_{y'}$" wherein x and y are integers, refers to the above defined "$(C_x-C_y)$alkylene" wherein the carbon atom is linked to a $NR_{x'}R_{y'}$, wherein x' and y' are integers, through the nitrogen atom.

The term "O($C_x$-$C_y$)alkyl" wherein x and y are integers, refers to the above defined "($C_x$-$C_y$)alkyl" groups wherein the carbon atom is linked to an oxygen atom, e.g. ethoxy and methoxy.

The term "($C_x$-$C_y$)haloalkyl" wherein x and y are integers refers to the above defined "($C_x$-$C_y$)alkyl" groups wherein one or more hydrogen atoms are replaced by one or more halogen atoms, which can be the same or different. Examples of said "($C_x$-$C_y$)haloalkyl" groups may thus include halogenated, poly-halogenated and fully halogenated alkyl groups wherein all hydrogen atoms are replaced by halogen atoms, e.g. trifluoromethyl, 1,1,1-trifluoro-2-methylpropan-2-yl, and 1,1-difluoroethyl.

The term "aryl" refers to mono cyclic carbon ring systems which have 6 ring atoms wherein the ring is aromatic. Examples of suitable aryl monocyclic ring systems include, for instance, phenyl.

The term "heteroaryl" refers to a mono- or bi-cyclic aromatic group containing one or more heteroatoms selected from S, N and O, and includes groups having two such monocyclic rings, or one such monocyclic ring and one monocyclic aryl ring, which are fused through a common bond, e.g. pyridinyl, pyrimidinyl, 1-methyl-1H-pyrazolyl, pyrazinyl, 1-methyl-1H-imidazolyl, isoxazolyl.

The term "—C(O)NH—($C_x$-$C_y$)alkylene-$NR_{x'}R_{y'}$", wherein x' and y' are integers, refers to a "($C_x$-$C_y$)alkylene-$NR_{x'}R_{y'}$" defined as described above, wherein the alkylene is linked to a —C(O)NH— group through its nitrogen atom.

The term "NHC(O)—($C_x$-$C_y$)alkylene-$NR_{x'}R_{y'}$" refers to a "($C_x$-$C_y$)alkylene-$NR_{x'}R_{y'}$", defined as described above, wherein the alkylene is linked to a —NHC(O)— group through its carbonyl group.

The term "NHC(O)—($C_x$-$C_y$)alkylene-O—($C_x$-$C_y$)alkyl" refers to the above defined "O($C_x$-$C_y$)alkyl" and the above defined "($C_x$-$C_y$)alkylene" wherein "O($C_x$-$C_y$)alkyl" and "($C_x$-$C_y$)alkylene" are linked through an oxygen and the above defined "($C_x$-$C_y$)alkylene" is furtherly linked to an amido group through its carbonyl moiety.

The term "NH-heteroaryl" refers to the above defined "heteroaryl" wherein the heteroaryl is linked to a nitrogen atom.

The term "heterocycloalkyl" refers to saturated or partly unsaturated mono- or bi-cyclic ring system of 3 to 12 ring atoms comprising one or more heteroatoms selected from N, S or O. Examples of heterocycloalkyl may include for instance, piperazinyl, oxopiperazinyl, dioxidothiomorpholino, oxetanyl and pyrrolidinyl.

The term "heterocycloalkyl-($C_x$-$C_y$)alkylene" refers to an heterocycloalkyl linked to a straight-chained or branched ($C_x$-$C_y$)alkylene group having from x to y carbon atoms.

A bond pointing to a wavy or squiggly line, such as

as used in structural formulas herein, depicts the bond that is the point of attachment of the moiety or substituent to the core or backbone structure.

When referring to substituents, a dash ("-") that is not between two letters, words, or symbols is meant to represent the point of attachment for such substituents.

The carbonyl group is herein preferably represented as —C(O)— as an alternative to the other common representations such as —CO—, —(CO)— or —C(=O)—.

Whenever basic amino groups are present in the compounds of formula (I), physiologically acceptable anions may be present, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate. Likewise, in the presence of acidic groups, corresponding physiological cation salts may be present as well, for instance including alkaline or alkaline earth metal ions.

The term "half maximal inhibitory concentration" (IC50) indicates the concentration of a particular compound or molecule required for obtaining 50% inhibition of a biological process in vitro.

The term "Ki" indicates the dissociation constant for the enzyme-inhibitor complex, expressed in molar units. It is an indicator of the binding affinity between inhibitor and DDR1 or DDR2 receptors.

As above indicated, the present invention refers to a series of compounds represented by the general formula (I) as herein below described in details, which are endowed with an inhibitory activity on receptors DDR1 and DDR2. Antagonizing receptors DDR1 and DDR2 can be particularly effective in the treatment of those diseases where the DDR receptors play a role, such as fibrosis and disease, disorder and condition related to fibrosis.

Indeed, as detailed in the experimental part below, the compounds of formula (I) of the present invention are able to act as inhibitors of both DDR1 and DDR2 receptors in a substantive and effective way. In particular, Table 5 below shows that for the compounds of the present invention, both the affinity for either DDR1 and DDR2 receptors and the inhibitory activity against either DDR1 and DDR2 receptors are below about 80 nM respectively in the binding (expressed as Ki) and the cell based assays (expressed as IC50). This confirms that the compounds of formula (I) are able to inhibit the two isoforms of DDR receptor mainly involved in fibrosis and diseases resulting from fibrosis. Accordingly, the compounds of formula (I) can be used in the treatment of fibrosis, in particular pulmonary fibrosis, when DDR1 and DDR2 are involved.

As indicated in the experimental part, comparative examples, in particular in Table 6, it is shown that, conversely to the comparative compound of Example C1, characterized by lacking a linker between the tetrahydrothieno pyridine ring and the Hy group, the presence of a —$CH_2$— or —C(O)— linker in that position in the present invention compounds unexpectedly and remarkably determines a relevant increase in the inhibitory activity on the DDR1 and DDR2 receptors.

Furthermore, as indicated in the same experimental part, data demonstrate that, conversely to the compound of Example C2, characterized by the absence of a linker between the tetrahydrothieno pyridine ring and the Hy group and by the —C(O)NH— group substitution at the α position with respect to sulphur atom, instead of the β position as in Example 3 of the present invention, the presence of the above mentioned linker concurrently with the substitution at the β position in the present invention compounds unexpectedly and noteworthy determines a relevant increase in the inhibitory activity against the DDR1 and DDR2 receptors.

Advantageously, the compounds of the present invention are endowed with a very high potency, they could be administered in human at a lower dosage respect to the compounds of the prior art, thus reducing the adverse events that typically occur administering higher dosages of drug.

In addition to being notably potent with respect to their inhibitory activity on both receptors DDR1 and DDR2, the compounds of the present invention are also characterized by being selective inhibitors of DDR1 and DDR2 receptors with respect to other human protein kinases, by a good inhalatory profile, that permits to act effectively on the lung compartment and have, at the same time, a low metabolic stability, that allows to minimize the drawbacks associated with the systemic exposure, such as safety and tolerability issues.

Therefore, the compounds of the present invention are particularly appreciated by the skilled person when looking at suitable and efficacious compounds useful for the treatment of fibrosis, in particular idiopathic pulmonary fibrosis, administered by the inhalation route and characterized by a good inhalatory profile, that corresponds to a good activity on the lung, a good lung retention and to a low metabolic stability, that minimizes the systemic exposure and correlated safety issues.

Thus, in one aspect the present invention relates to a compound of general formula (I)

(I)

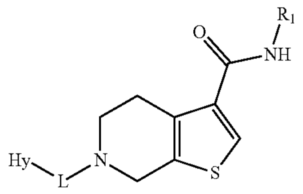

wherein

L is selected from the group consisting of —C(O)— and —$CH_2$—;

Hy is a monocyclic heteroaryl optionally substituted with one or more groups selected from —($C_1$-$C_4$)alkyl, halogen atoms, cyano, —$(CH_2)_n R_4 R_5$, —NH-heterocycloalkyl, —O—($C_1$-$C_6$)alkyl, —($C_1$-$C_6$)haloalkyl, —C(O)NH—($C_1$-$C_6$)alkylene-$NR_4R_5$, —O—($C_1$-$C_6$) alkylene-cycloalkyl, —NHC(O)—($C_1$-$C_6$)alkyl, —NHC(O)—($C_1$-$C_6$)alkylene-$NR_4R_5$, —NHC(O)—($C_1$-$C_6$)alkylene-O—($C_1$-$C_4$)alkyl, —NH—($C_1$-$C_6$)alkylene-O—($C_1$-$C_4$)alkyl, —NH—($C_1$-$C_6$)alkylene-OH, -heteroaryl optionally substituted by one or more —($C_1$-$C_4$)alkyl, —NH— heteroaryl, wherein said heteroaryl is optionally substituted by one or more —($C_1$-$C_4$)alkyl, and heterocycloalkyl optionally substituted by one or more groups selected from oxo and —($C_1$-$C_6$)alkyl;

$R_1$ is selected from the group consisting of:

Het which is an heteroaryl optionally substituted with one or more groups selected from —($C_1$-$C_4$)alkyl, —($C_1$-$C_4$)haloalkyl and aryl, wherein said aryl is optionally substituted with one or more groups selected from —($C_1$-$C_4$)alkyl and halogen atoms; and

X (X)

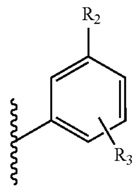

wherein $R_2$ is selected from the group consisting of —O($C_1$-$C_4$)haloalkyl, halogen atoms, —O($C_3$-$C_7$)cycloalkyl and —($C_1$-$C_4$)haloalkyl;

$R_3$ is H or is selected from the group consisting of halogen atoms, cyano, —O($C_1$-$C_4$)alkyl, —O($C_1$-$C_4$)haloalkyl, heterocycloalkyl-($C_1$-$C_4$)alkylene-, —($C_1$-$C_4$)alkylene-heterocycloalkyl-$NR_4R_5$, and heteroaryl optionally substituted with one or more —($C_1$-$C_4$)alkyl, and wherein said heterocycloalkyl is optionally substituted with one or more —($C_1$-$C_4$)alkyl;

n is 0, 1 or 2;

$R_4$ is H or —($C_1$-$C_4$)alkyl;

$R_5$ is H or —($C_1$-$C_4$)alkyl;

and pharmaceutically acceptable salts thereof.

In a preferred embodiment, the present invention relates to a compound of general formula (I) wherein L is —$CH_2$.

In another preferred embodiment, the present invention relates to a compound of general formula (I) wherein $R_1$ is X'

(X')

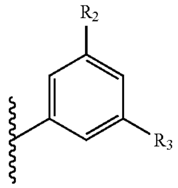

represented by general formula (Ia)

(Ia)

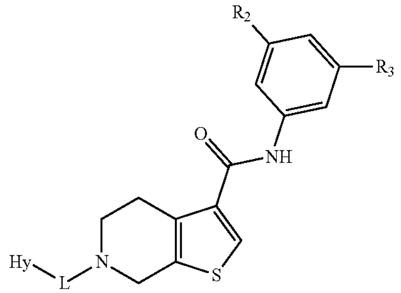

wherein L, Hy, $R_2$ and $R_3$ are as defined above.

In a further preferred embodiment, the present invention refers to a compound of formula (Ia) wherein L is —$CH_2$—, represented by formula (Iaa)

(Iaa)

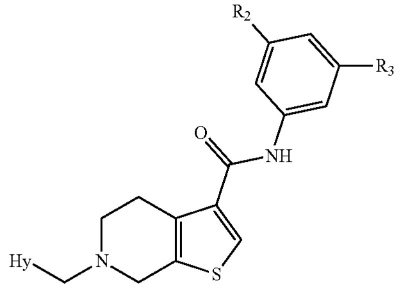

wherein Hy, $R_2$ and $R_3$ are as defined above.

In another preferred embodiment, the present invention relates to a compound of general formula (Iaa) wherein Hy is selected from the group consisting of pyridin-3-yl, pyrimidin-5-yl, ((1-methyl-1H-pyrazol-4-yl)amino)pyrimidin-5-yl, 4-(2-methoxyacetamido)pyridin-3-yl, 5-cyanopyridin-3-yl, 5-chloropyridin-3-yl, 5-methoxypyridin-3-yl, 5-methylpyridin-3-yl, 5-(trifluoromethyl)pyridin-3-yl, 3-aminopyrazin-2-yl, 2-aminopyrimidin-5-yl, 5-(4-methyl-3-oxopiperazin-1-yl)pyridin-3-yl, 5-(1,1-dioxidothiomorpholino)pyridin-3-yl, -((5-(2-(dimethylamino)acetamido) pyridin-3-yl, 2-(oxetan-3-ylamino)pyrimidin-5-yl, 2-acetamidopyrimidin-5-yl, (2-(methylamino)pyrimidin-5-yl, ((2-methoxyethyl)amino)pyrimidin-5-yl, 6-acetamidopyridin-3-yl, 2-aminopyridin-3-yl, ((2-hydroxyethyl) amino)pyrimidin-5-yl, 4-aminopyrimidin-5-yl, 2-amino-4-methylpyrimidin-5-yl, (2-fluoropropan-2-yl)pyrimidin-5-yl, 4-methoxypyrimidin-5-yl, 4-cyclopropoxypyrimidin-5-yl, (1-methyl-1H-pyrazol-4-yl)pyridin-3-yl and (5-fluoropyridin-3-yl)methyl.

In a further preferred embodiment, the present invention relates to a compound of general formula (Iaa) wherein $R_2$ is selected from the group consisting of trifluoromethyl, trifluoromethoxy, 1,1-difluoroethyl and difluoromethoxy.

In another particularly preferred embodiment, the present invention relates to a compound of general formula (Iaa) wherein $R_3$ is H or is selected from the group consisting of (4-methylpiperazin-1-yl)methyl, 4-methyl-1H-imidazol-1-yl, fluorine, (3-(dimethylamino)pyrrolidin-1-yl)methyl, (dimethylamino)methyl and cyano.

According to a preferred embodiment, the invention refers to at least one of the compounds of Formula (Iaa) listed in the Table 1 below and pharmaceutically acceptable salts thereof. These compounds are particularly active on receptors DDR1 and DDR2, as shown in Table 5.

TABLE 1

List of compounds of Formula (Iaa)

| Example No. | Structure | Chemical Name |
|---|---|---|
| 1 | 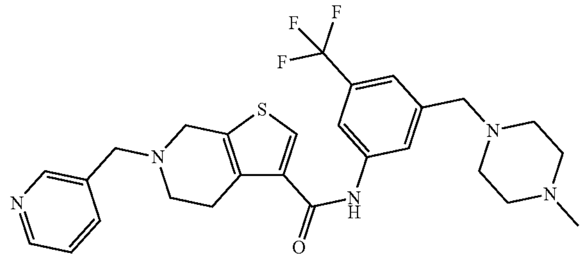 [SMILES: CN1CCN(Cc2cc(NC(=O)c3csc4c3CCN(Cc3cccnc3)C4)cc(C(F)(F)F)c2)CC1] | N-(3-((4-methylpiperazin-1-yl)methyl)-5-(trifluoromethyl)phenyl)-6-(pyridin-3-ylmethyl)-4,5,6,7-tetrahydrothieno[2,3-c]pyridine-3-carboxamide |
| 2 | 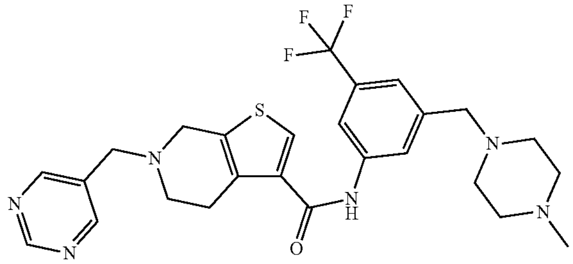 [SMILES: CN1CCN(Cc2cc(NC(=O)c3csc4c3CCN(Cc3cncnc3)C4)cc(C(F)(F)F)c2)CC1] | N-(3-((4-methylpiperazin-1-yl)methyl)-5-(trifluoromethyl)phenyl)-6-(pyrimidin-5-ylmethyl)-4,5,6,7-tetrahydrothieno[2,3-c]pyridine-3-carboxamide |
| 3 | 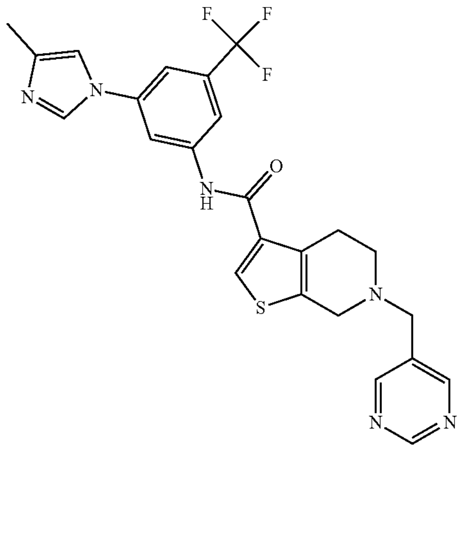 [SMILES: Cc1cn(-c2cc(NC(=O)c3csc4c3CCN(Cc3cncnc3)C4)cc(C(F)(F)F)c2)cn1] | N-(3-(4-methyl-1H-imidazol-1-yl)-5-(trifluoromethyl)phenyl)-6-(pyrimidin-5-ylmethyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 4 | 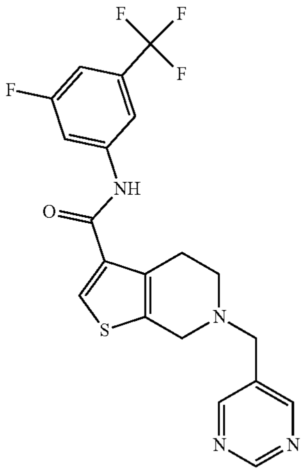 [SMILES: O=C(Nc1cc(F)cc(C(F)(F)F)c1)c1csc2c1CCN(Cc1cncnc1)C2] | N-(3-fluoro-5-(trifluoromethyl)phenyl)-6-(pyrimidin-5-ylmethyl)-4,5,6,7-tetrahydrothieno[2,3-c]pyridine-3-carboxamide |
| 5 | 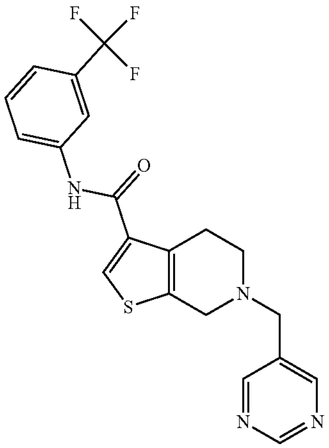 [SMILES: O=C(Nc1cccc(C(F)(F)F)c1)c1csc2c1CCN(Cc1cncnc1)C2] | 6-(pyrimidin-5-ylmethyl)-N-(3-(trifluoromethyl)phenyl)-4,5,6,7-tetrahydrothieno[2,3-c]pyridine-3-carboxamide |
| 7 | 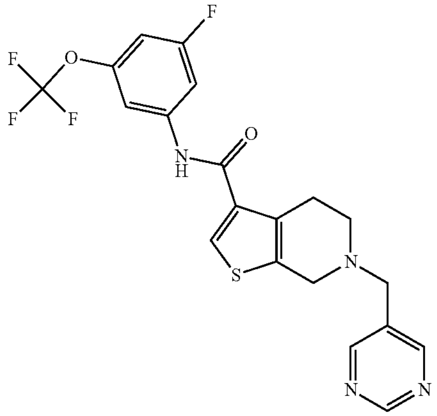 [SMILES: O=C(Nc1cc(F)cc(OC(F)(F)F)c1)c1csc2c1CCN(Cc1cncnc1)C2] | N-(3-fluoro-5-(trifluoromethoxy)phenyl)-6-(pyrimidin-5-ylmethyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 9 | 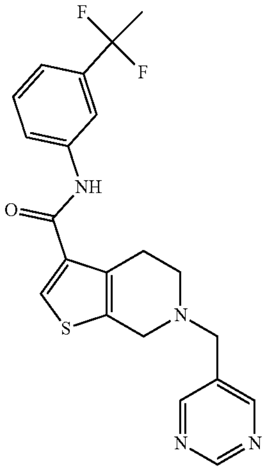 [SMILES: CC(F)(F)c1cccc(NC(=O)c2csc3c2CCN(Cc2cncnc2)C3)c1] | N-(3-(1,1-difluoroethyl)phenyl)-6-(pyrimidin-5-ylmethyl)-4,5,6,7-tetrahydrothieno[2,3-c]pyridine-3-carboxamide |
| 12 | 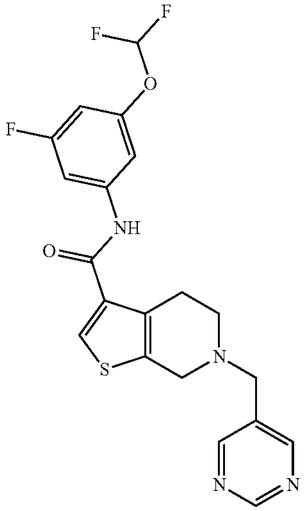 [SMILES: O=C(Nc1cc(F)cc(OC(F)F)c1)c1csc2c1CCN(Cc1cncnc1)C2] | N-(3-(difluoromethoxy)-5-fluorophenyl)-6-(pyrimidin-5-ylmethyl)-4,5,6,7-tetrahydrothieno[2,3-c]pyridine-3-carboxamide |
| 13 | 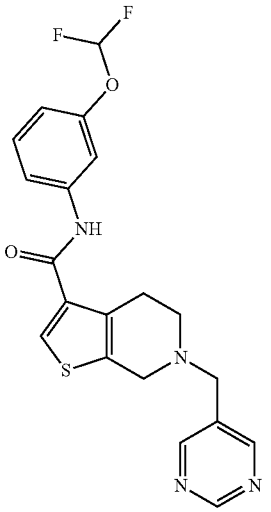 [SMILES: O=C(Nc1cccc(OC(F)F)c1)c1csc2c1CCN(Cc1cncnc1)C2] | N-(3-(difluoromethoxy)phenyl)-6-(pyrimidin-5-ylmethyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 14 | 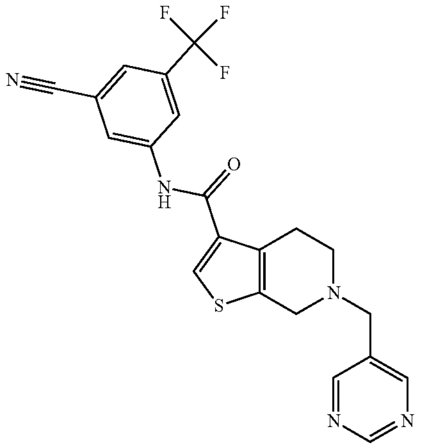 [SMILES: N#Cc1cc(NC(=O)c2csc3c2CCN(Cc2cncnc2)C3)cc(C(F)(F)F)c1] | N-(3-cyano-5-(trifluoromethyl)phenyl)-6-(pyrimidin-5-ylmethyl)-4,5,6,7-tetrahydrothieno[2,3-c]pyridine-3-carboxamide |
| 17 | 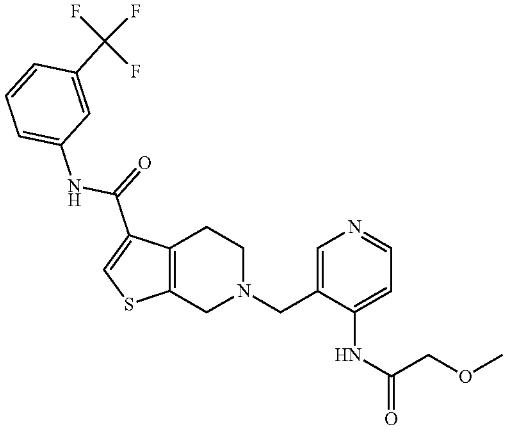 [SMILES: COCC(=O)Nc1ccncc1CN1CCc2c(C(=O)Nc3cccc(C(F)(F)F)c3)csc2C1] | 6-((4-(2-methoxyacetamido)pyridin-3-yl)methyl)-N-(3-(trifluoromethyl)phenyl)-4,5,6,7-tetrahydrothieno[2,3-c]pyridine-3-carboxamide |
| 18 | 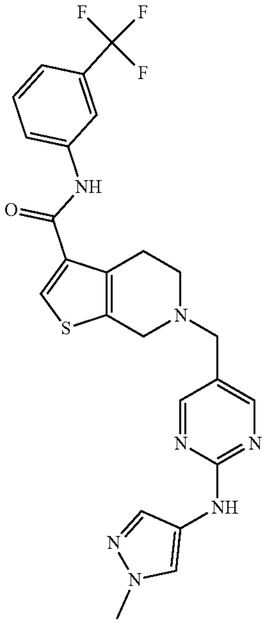 [SMILES: Cn1cc(Nc2ncc(CN3CCc4c(C(=O)Nc5cccc(C(F)(F)F)c5)csc4C3)cn2)cn1] | 6-((2-((1-methyl-1H-pyrazol-4-yl)amino)pyrimidin-5-yl)methyl)-N-(3-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 19 | 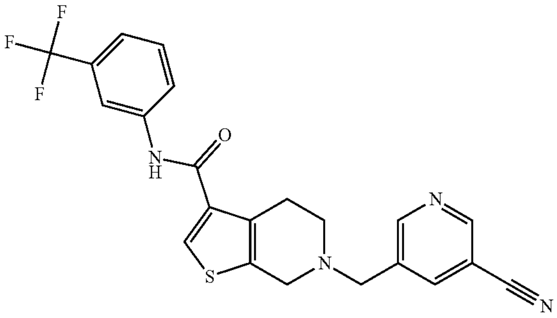 [SMILES: N#Cc1cncc(CN2CCc3c(C(=O)Nc4cccc(C(F)(F)F)c4)csc3C2)c1] | 6-((5-cyanopyridin-3-yl)methyl)-N-(3-(trifluoromethyl)phenyl)-4,5,6,7-tetrahydrothieno[2,3-c]pyridine-3-carboxamide |
| 20 | 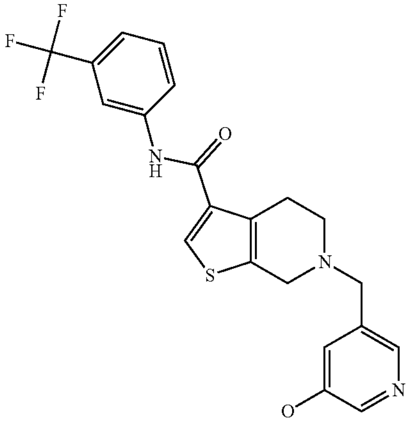 [SMILES: O=C(Nc1cccc(C(F)(F)F)c1)c1csc2c1CCN(Cc1cncc(O)c1)C2] | 6-((5-chloropyridin-3-yl)methyl)-N-(3-(trifluoromethyl)phenyl)-4,5,6,7-tetrahydrothieno[2,3-c]pyridine-3-carboxamide |
| 21 | 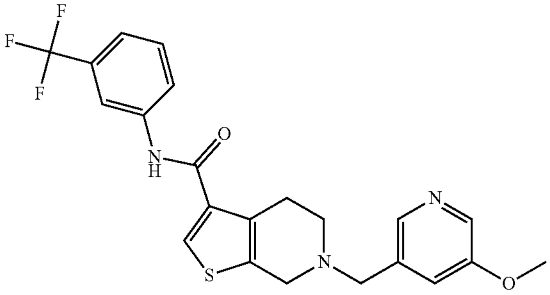 [SMILES: COc1cncc(CN2CCc3c(C(=O)Nc4cccc(C(F)(F)F)c4)csc3C2)c1] | 6-((5-methoxypyridin-3-yl)methyl)-N-(3-(trifluoromethyl)phenyl)-4,5,6,7-tetrahydrothieno[2,3-c]pyridine-3-carboxamide |
| 22 | 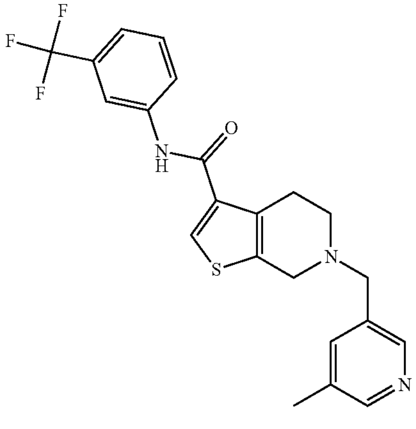 [SMILES: Cc1cncc(CN2CCc3c(C(=O)Nc4cccc(C(F)(F)F)c4)csc3C2)c1] | 6-((5-methylpyridin-3-yl)methyl)-N-(3-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 23 | 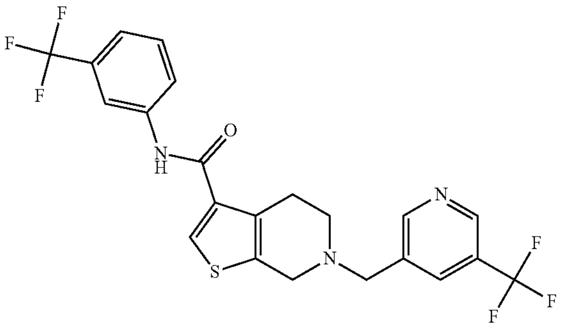 [SMILES: O=C(Nc1cccc(C(F)(F)F)c1)c1csc2c1CCN(Cc1cncc(C(F)(F)F)c1)C2] | N-(3-(trifluoromethyl)phenyl)-6-((5-(trifluoromethyl)pyridin-3-yl)methyl)-4,5,6,7-tetrahydrothieno[2,3-c]pyridine-3-carboxamide |
| 24 | 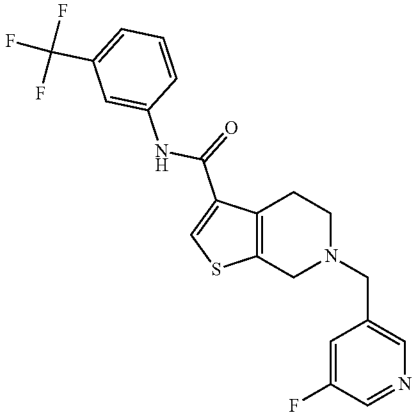 [SMILES: O=C(Nc1cccc(C(F)(F)F)c1)c1csc2c1CCN(Cc1cncc(F)c1)C2] | 6-((5-fluoropyridin-3-yl)methyl)-N-(3-(trifluoromethyl)phenyl)-4,5,6,7-tetrahydrothieno[2,3-c]pyridine-3-carboxamide |
| 25 | 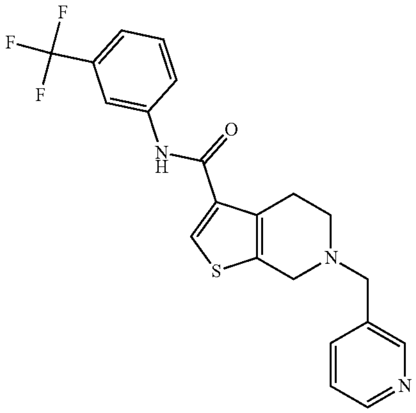 [SMILES: O=C(Nc1cccc(C(F)(F)F)c1)c1csc2c1CCN(Cc1cccnc1)C2] | 6-(pyridin-3-ylmethyl)-N-(3-(trifluoromethyl)phenyl)-4,5,6,7-tetrahydrothieno[2,3-c]pyridine-3-carboxamide |
| 27 | 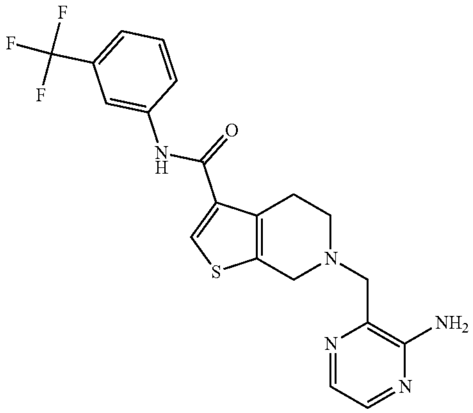 [SMILES: Nc1nccnc1CN1CCc2c(C(=O)Nc3cccc(C(F)(F)F)c3)csc2C1] | 6-((3-aminopyrazin-2-yl)methyl)-N-(3-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 28 | 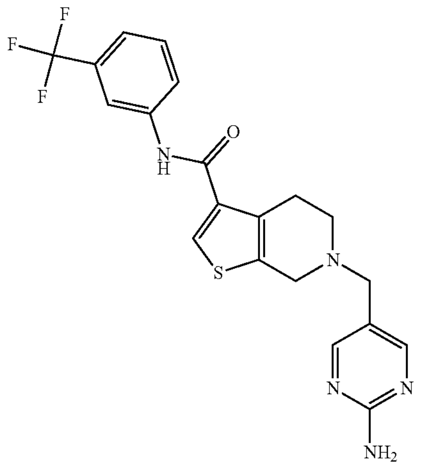 [SMILES: Nc1ncc(CN2CCc3c(C(=O)Nc4cccc(C(F)(F)F)c4)csc3C2)cn1] | 6-((2-aminopyrimidin-5-yl)methyl)-N-(3-(trifluoromethyl)phenyl)-4,5,6,7-tetrahydrothieno[2,3-c]pyridine-3-carboxamide |
| 29 | 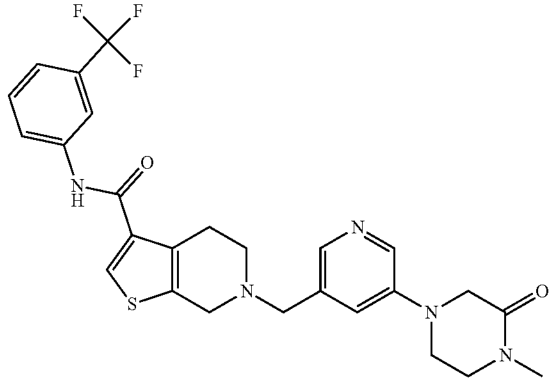 [SMILES: CN1CCN(c2cncc(CN3CCc4c(C(=O)Nc5cccc(C(F)(F)F)c5)csc4C3)c2)CC1=O] | 6-((5-(4-methyl-3-oxopiperazin-1-yl)pyridin-3-yl)methyl)-N-(3-(trifluoromethyl)phenyl)-4,5,6,7-tetrahydrothieno[2,3-c]pyridine-3-carboxamide |
| 30 | 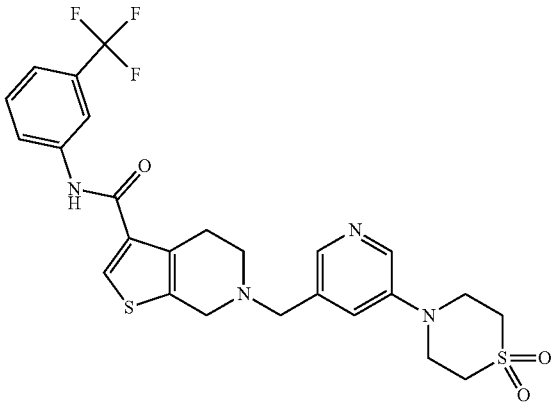 [SMILES: O=C(Nc1cccc(C(F)(F)F)c1)c1csc2c1CCN(Cc1cncc(N3CCS(=O)(=O)CC3)c1)C2] | 6-((5-(1,1-dioxidothiomorpholino)pyridin-3-yl)methyl)-N-(3-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 31 | 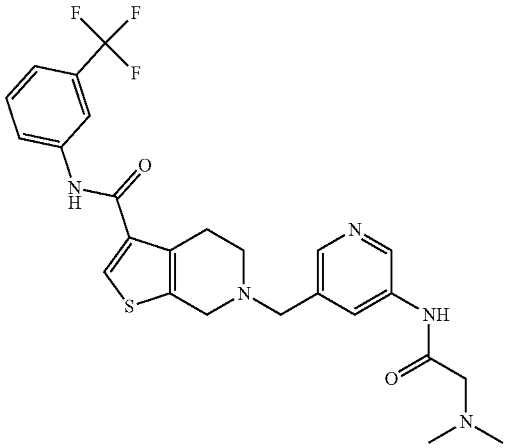 [SMILES: CN(C)CC(=O)Nc1cncc(CN2CCc3c(C(=O)Nc4cccc(C(F)(F)F)c4)csc3C2)c1] | 6-((5-(2-(dimethylamino)acetamido)pyridin-3-yl)methyl)-N-(3-(trifluoromethyl)phenyl)-4,5,6,7-tetrahydrothieno[2,3-c]pyridine-3-carboxamide |
| 37 | 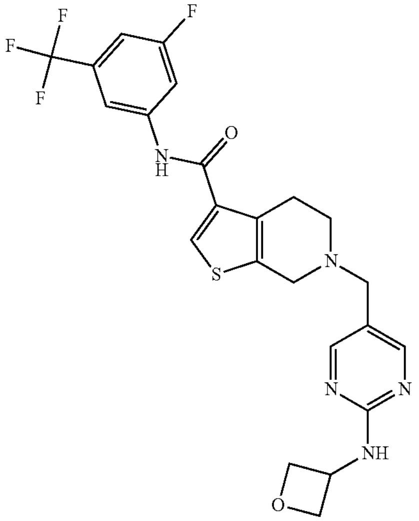 [SMILES: O=C(Nc1cc(F)cc(C(F)(F)F)c1)c1csc2c1CCN(Cc1cnc(NC3COC3)nc1)C2] | N-(3-fluoro-5-(trifluoromethyl)phenyl)-6-((2-(oxetan-3-ylamino)pyrimidin-5-yl)methyl)-4,5,6,7-tetrahydrothieno[2,3-c]pyridine-3-carboxamide |
| 38 | 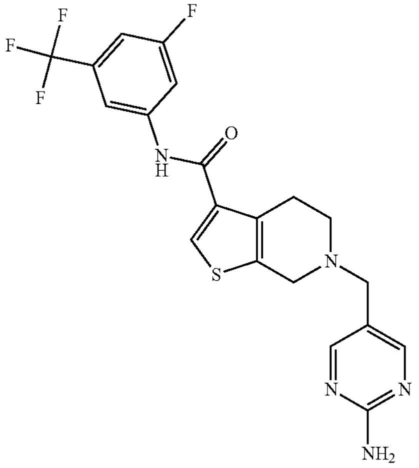 [SMILES: Nc1ncc(CN2CCc3c(C(=O)Nc4cc(F)cc(C(F)(F)F)c4)csc3C2)cn1] | 6-((2-aminopyrimidin-5-yl)methyl)-N-(3-fluoro-5-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 39 | 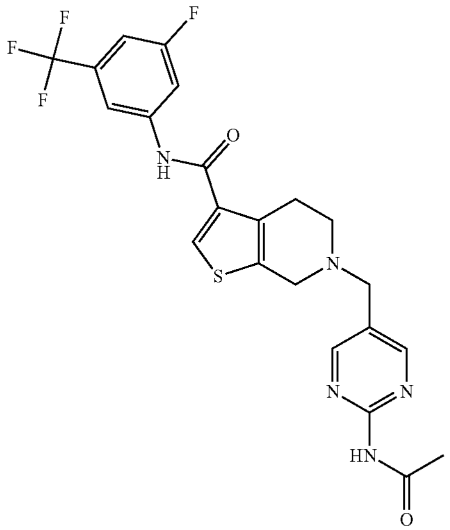 [SMILES: CC(=O)Nc1ncc(CN2CCc3c(C(=O)Nc4cc(F)cc(C(F)(F)F)c4)csc3C2)cn1] | 6-((2-acetamidopyrimidin-5-yl)methyl)-N-(3-fluoro-5-(trifluoromethyl)phenyl)-4,5,6,7-tetrahydrothieno[2,3-c]pyridine-3-carboxamide |
| 40 | 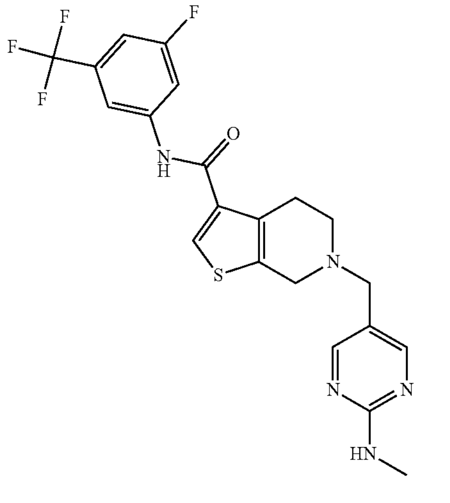 [SMILES: CNc1ncc(CN2CCc3c(C(=O)Nc4cc(F)cc(C(F)(F)F)c4)csc3C2)cn1] | N-(3-fluoro-5-(trifluoromethyl)phenyl)-6-((2-(methylamino)pyrimidin-5-yl)methyl)-4,5,6,7-tetrahydrothieno[2,3-c]pyridine-3-carboxamide |
| 41 | 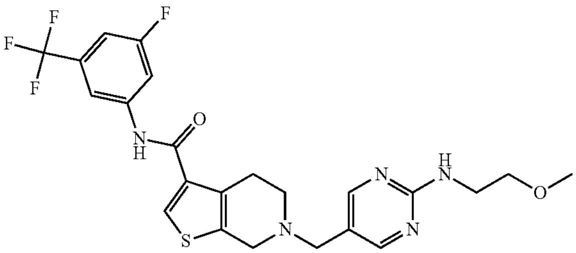 [SMILES: COCCNc1ncc(CN2CCc3c(C(=O)Nc4cc(F)cc(C(F)(F)F)c4)csc3C2)cn1] | N-(3-fluoro-5-(trifluoromethyl)phenyl)-6-((2-((2-methoxyethyl)amino)pyrimidin-5-yl)methyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 42 | 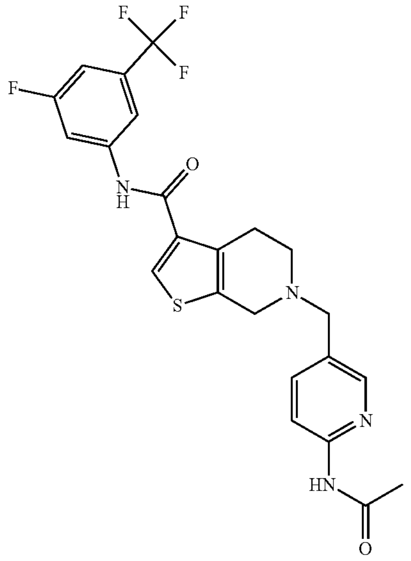 [SMILES: CC(=O)Nc1ccc(CN2CCc3c(C(=O)Nc4cc(F)cc(C(F)(F)F)c4)csc3C2)cn1] | 6-((6-acetamidopyridin-3-yl)methyl)-N-(3-fluoro-5-(trifluoromethyl)phenyl)-4,5,6,7-tetrahydrothieno[2,3-c]pyridine-3-carboxamide |
| 43 | 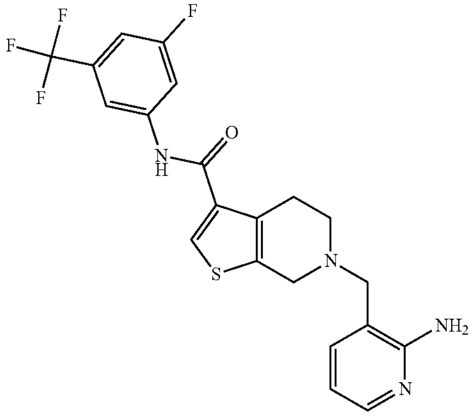 [SMILES: Nc1ncccc1CN1CCc2c(C(=O)Nc3cc(F)cc(C(F)(F)F)c3)csc2C1] | 6-((2-aminopyridin-3-yl)methyl)-N-(3-fluoro-5-(trifluoromethyl)phenyl)-4,5,6,7-tetrahydrothieno[2,3-c]pyridine-3-carboxamide |
| 44 | 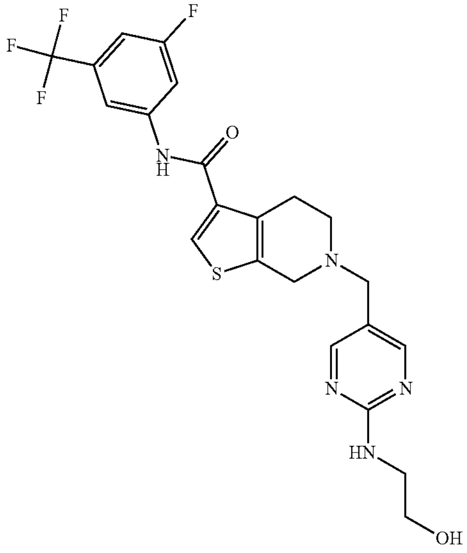 [SMILES: O=C(Nc1cc(F)cc(C(F)(F)F)c1)c1csc2c1CCN(Cc1cnc(NCCO)nc1)C2] | N-(3-fluoro-5-(trifluoromethyl)phenyl)-6-((2-((2-hydroxyethyl)amino)pyrimidin-5-yl)methyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 45 | 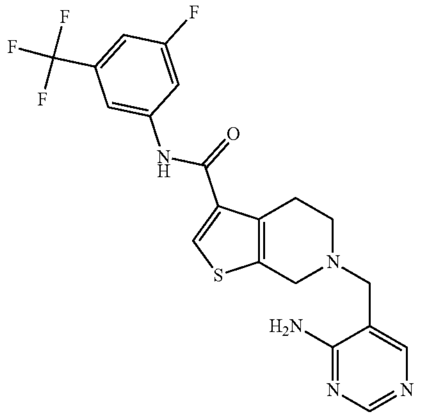 [SMILES: Nc1ncncc1CN1CCc2c(C(=O)Nc3cc(F)cc(C(F)(F)F)c3)csc2C1] | 6-((4-aminopyrimidin-5-yl)methyl)-N-(3-fluoro-5-(trifluoromethyl)phenyl)-4,5,6,7-tetrahydrothieno[2,3-c]pyridine-3-carboxamide |
| 46 | 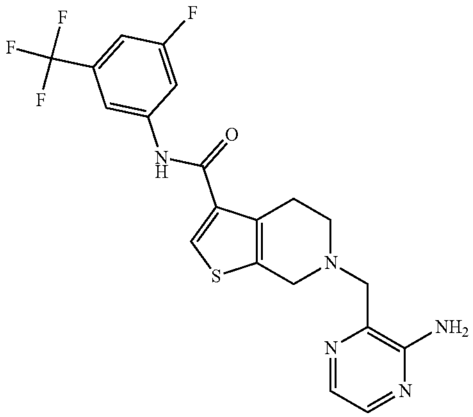 [SMILES: Nc1nccnc1CN1CCc2c(C(=O)Nc3cc(F)cc(C(F)(F)F)c3)csc2C1] | 6-((3-aminopyrazin-2-yl)methyl)-N-(3-fluoro-5-(trifluoromethyl)phenyl)-4,5,6,7-tetrahydrothieno[2,3-c]pyridine-3-carboxamide |
| 47 | 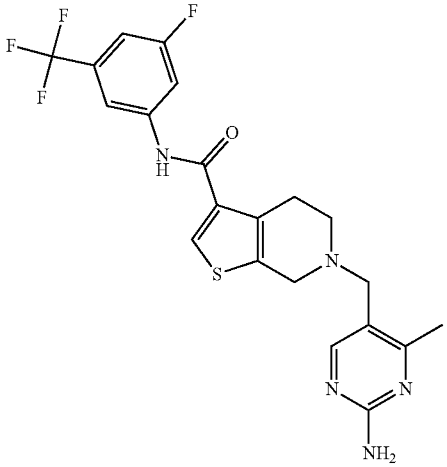 [SMILES: Cc1nc(N)ncc1CN1CCc2c(C(=O)Nc3cc(F)cc(C(F)(F)F)c3)csc2C1] | 6-((2-amino-4-methylpyrimidin-5-yl)methyl)-N-(3-fluoro-5-(trifluoromethyl)phenyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 48 | 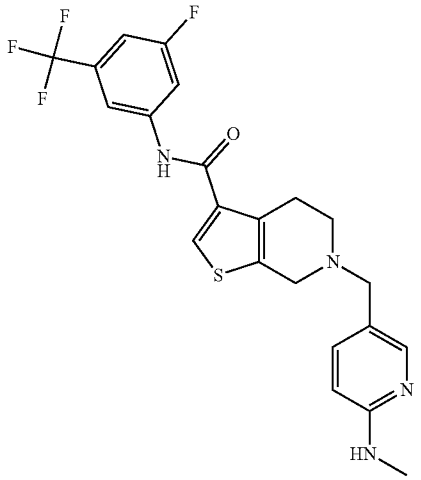 [SMILES: CNc1ccc(CN2CCc3c(C(=O)Nc4cc(F)cc(C(F)(F)F)c4)csc3C2)cn1] | N-(3-fluoro-5-(trifluoromethyl)phenyl)-6-((6-(methylamino)pyridin-3-yl)methyl)-4,5,6,7-tetrahydrothieno[2,3-c]pyridine-3-carboxamide |
| 50 | 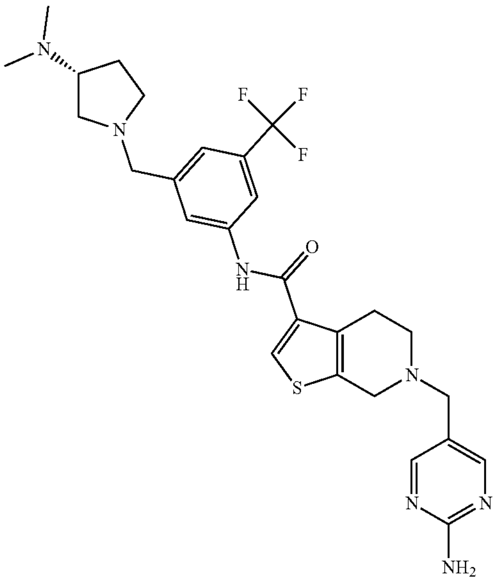 [SMILES: CN(C)[C@@H]1CCN(Cc2cc(NC(=O)c3csc4c3CCN(Cc3cnc(N)nc3)C4)cc(C(F)(F)F)c2)C1] | (R)-6-((2-aminopyrimidin-5-yl)methyl)-N-(3-((3-(dimethylamino)pyrrolidin-1-yl)methyl)-5-(trifluoromethyl)phenyl)-4,5,6,7-tetrahydrothieno[2,3-c]pyridine-3-carboxamide |
| 51 | 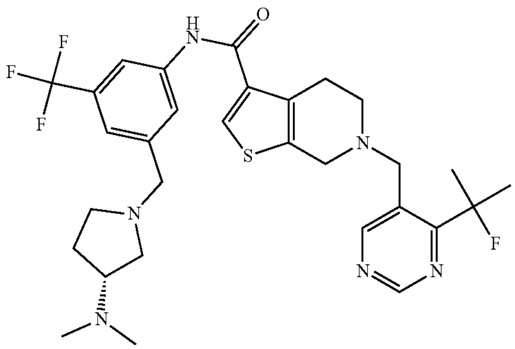 [SMILES: CN(C)[C@@H]1CCN(Cc2cc(NC(=O)c3csc4c3CCN(Cc3cncnc3C(C)(C)F)C4)cc(C(F)(F)F)c2)C1] | (R)-N-(3-((3-(dimethylamino)pyrrolidin-1-yl)methyl)-5-(trifluoromethyl)phenyl)-6-((4-(2-fluoropropan-2-yl)pyrimidin-5-yl)methyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 52 | 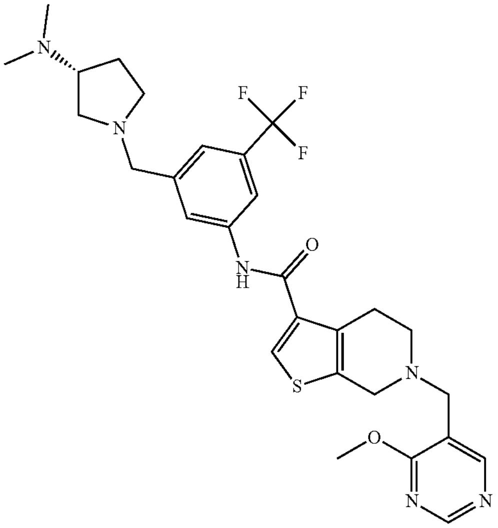 [SMILES: COc1ncncc1CN1CCc2c(C(=O)Nc3cc(CN4CC[C@@H](N(C)C)C4)cc(C(F)(F)F)c3)csc2C1] | (R)-N-(3-((3-(dimethylamino)pyrrolidin-1-yl)methyl)-5-(trifluoromethyl)phenyl)-6-((4-methoxypyrimidin-5-yl)methyl)-4,5,6,7-tetrahydrothieno[2,3-c]pyridine-3-carboxamide |
| 53 | 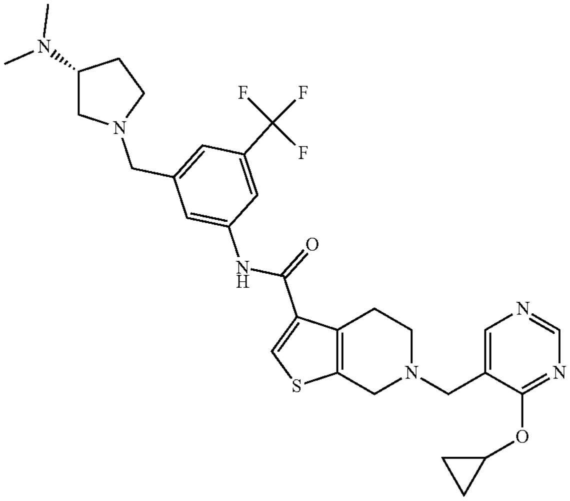 [SMILES: CN(C)[C@@H]1CCN(Cc2cc(NC(=O)c3csc4c3CCN(Cc3cncnc3OC3CC3)C4)cc(C(F)(F)F)c2)C1] | (R)-6-((4-cyclopropoxypyrimidin-5-yl)methyl)-N-(3-((3-(dimethylamino)pyrrolidin-1-yl)methyl)-5-(trifluoromethyl)phenyl)-4,5,6,7-tetrahydrothieno[2,3-c]pyridine-3-carboxamide |
| 54 | 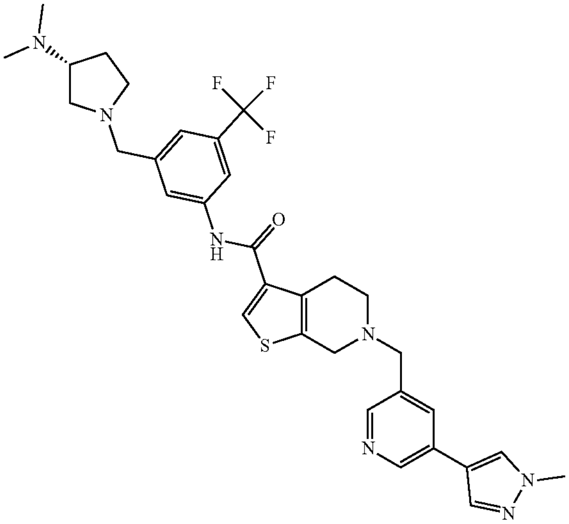 | (R)-N-(3-((3-(dimethylamino)pyrrolidin-1-yl)methyl)-5-(trifluoromethyl)phenyl)-6-((5-(1-methyl-1H-pyrazol-4-yl)pyridin-3-yl)methyl)-4,5,6,7-tetrahydrothieno[2,3-c]pyridine-3-carboxamide |

TABLE 1-continued

| List of compounds of Formula (Iaa) | | |
|---|---|---|
| Example No. | Structure | Chemical Name |
| 55 | 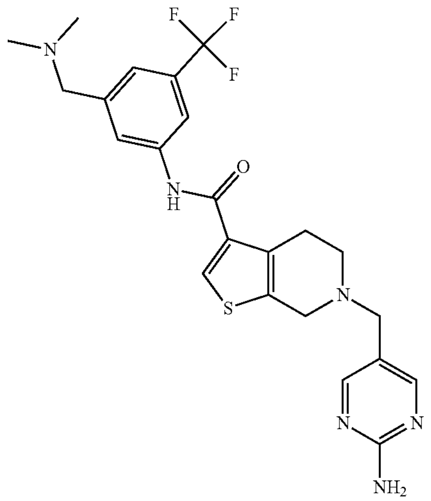 [SMILES: CN(C)Cc1cc(NC(=O)c2csc3c2CCN(Cc2cnc(N)nc2)C3)cc(C(F)(F)F)c1] | 6-((2-aminopyrimidin-5-yl)methyl)-N-(3-((dimethylamino)methyl)-5-(trifluoromethyl)phenyl)-4,5,6,7-tetrahydrothieno[2,3-c]pyridine-3-carboxamide |
| 58 | 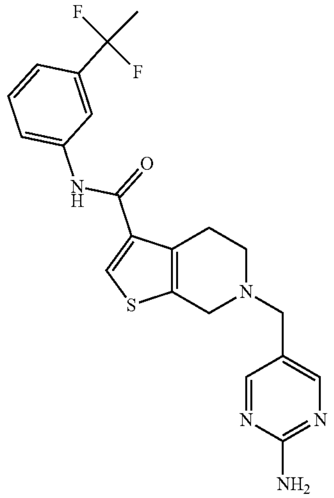 [SMILES: CC(F)(F)c1cccc(NC(=O)c2csc3c2CCN(Cc2cnc(N)nc2)C3)c1] | 6-((2-aminopyrimidin-5-yl)methyl)-N-(3-(1,1-difluoroethyl)phenyl)-4,5,6,7-tetrahydrothieno[2,3-c]pyridine-3-carboxamide |
| 59 | 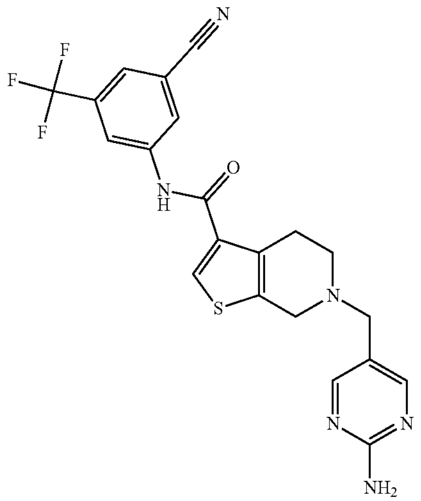 [SMILES: N#Cc1cc(NC(=O)c2csc3c2CCN(Cc2cnc(N)nc2)C3)cc(C(F)(F)F)c1] | 6-((2-aminopyrimidin-5-yl)methyl)-N-(3-cyano-5-(trifluoromethyl)phenyl)-4,5,6,7-tetrahydrothieno[2,3-c]pyridine-3-carboxamide |

In another preferred embodiment the present invention refers to a compound of formula (I) wherein L is —$CH_2$—, $R_1$ is X"

(X")

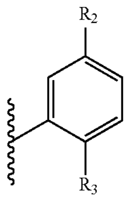

represented by formula (Iaa')

(Iaa')

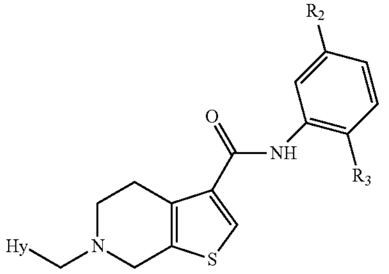

wherein Hy, $R_2$ and $R_3$ are as defined above.

In another preferred embodiment, the present invention relates to a compound of general formula (Iaa') wherein $R_2$ is trifluoromethyl.

In a further preferred embodiment, the present invention relates to a compound of general formula (Iaa') wherein $R_3$ is fluorine.

In a further particularly preferred embodiment, the present invention relates to a compound of general formula (Iaa') wherein Hy is pyrimidin-5-yl.

According to a preferred embodiment, the invention refers to a compound of Formula (Iaa') listed in the Table 2 below and pharmaceutically acceptable salts thereof. These compounds are particularly active on receptors DDR1 and DDR2, as shown in Table 5.

TABLE 2

List of compounds of Formula (Iaa')

| Example No. | Structure | Chemical Name |
|---|---|---|
| 11 | 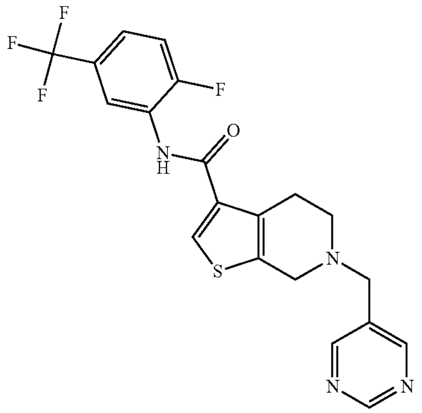 [SMILES: O=C(Nc1cc(C(F)(F)F)ccc1F)c1csc2c1CCN(Cc1cncnc1)C2] | N-(2-fluoro-5-(trifluoromethyl)phenyl)-6-(pyrimidin-5-ylmethyl)-4,5,6,7-tetrahydrothieno[2,3-c]pyridine-3-carboxamide |

In another preferred embodiment the present invention refers to a compound of formula (I) wherein L is —$CH_2$—, $R_1$ is X'''

(X''')

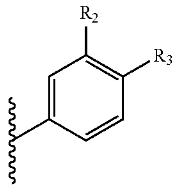

represented by formula (Iaa")

(Iaa")

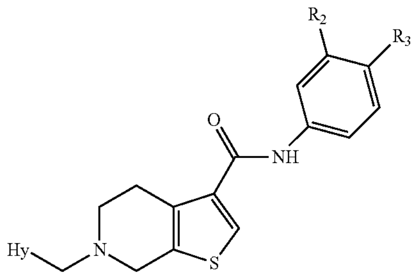

wherein Hy, $R_2$ and $R_3$.

In a particularly preferred embodiment, the present invention relates to a compound of general formula (Iaa") wherein $R_2$ is selected from the group consisting of trifluoromethyl and trifluoromethoxy.

In another particularly preferred embodiment, the present invention relates to a compound of general formula (Iaa")

wherein $R_3$ is selected from the group consisting of fluorine, chlorine and (dimethylamino)methyl.

In a further preferred embodiment, the present invention relates to a compound of general formula (Iaa") wherein Hy is pyrimidin-5-yl and 2-aminopyrimidin-5-yl.

According to a preferred embodiment, the invention refers to at least one of the compounds of Formula (Iaa") listed in the Table 3 below and pharmaceutically acceptable salts thereof. These compounds are particularly active on receptors DDR1 and DDR2, as shown in Table 5.

TABLE 3

| List of compounds of Formula (Iaa") | | |
|---|---|---|
| Example No. | Structure | Chemical Name |
| 8 | 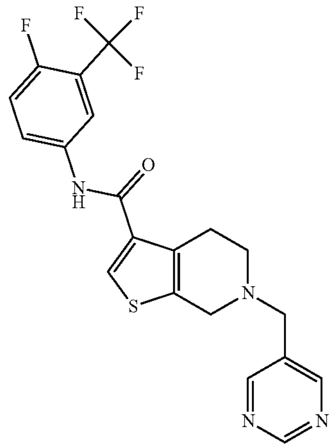 [SMILES: O=C(Nc1ccc(F)c(C(F)(F)F)c1)c1csc2c1CCN(Cc1cncnc1)C2] | N-(4-fluoro-3-(trifluoromethyl)phenyl)-6-(pyrimidin-5-ylmethyl)-4,5,6,7-tetrahydrothieno[2,3-c]pyridine-3-carboxamide |
| 10 | 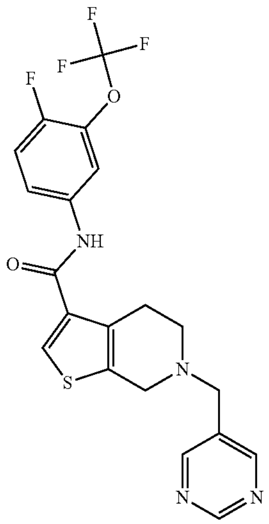 [SMILES: O=C(Nc1ccc(F)c(OC(F)(F)F)c1)c1csc2c1CCN(Cc1cncnc1)C2] | N-(4-fluoro-3-(trifluoromethoxy)phenyl)-6-(pyrimidin-5-ylmethyl)-4,5,6,7-tetrahydrothieno[2,3-c]pyridine-3-carboxamide |

TABLE 3-continued

List of compounds of Formula (Iaa")

| Example No. | Structure | Chemical Name |
| --- | --- | --- |
| 56 | 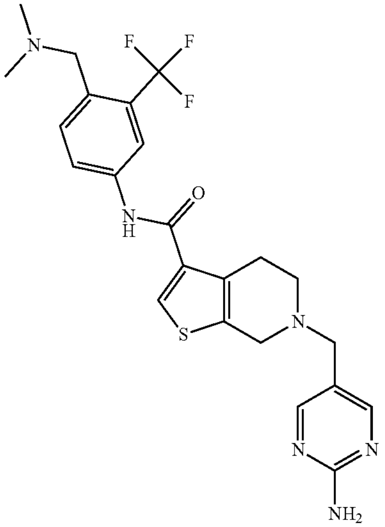 [SMILES: CN(C)Cc1ccc(NC(=O)c2csc3c2CCN(Cc2cnc(N)nc2)C3)cc1C(F)(F)F] | 6-((2-aminopyrimidin-5-yl)methyl)-N-(4-((dimethylamino)methyl)-3-(trifluoromethyl)phenyl)-4,5,6,7-tetrahydrothieno[2,3-c]pyridine-3-carboxamide |
| 61 | 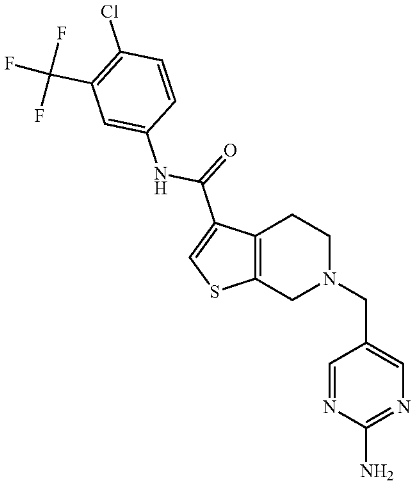 [SMILES: Nc1ncc(CN2CCc3c(C(=O)Nc4ccc(Cl)c(C(F)(F)F)c4)csc3C2)cn1] | 6-((2-aminopyrimidin-5-yl)methyl)-N-(4-chloro-3-(trifluoromethyl)phenyl)-4,5,6,7-tetrahydrothieno[2,3-c]pyridine-3-carboxamide |

In another preferred embodiment, the present invention refers to a compound of formula (Ia) wherein L is —C(O)—, represented by formula (Jab)

(Iab)

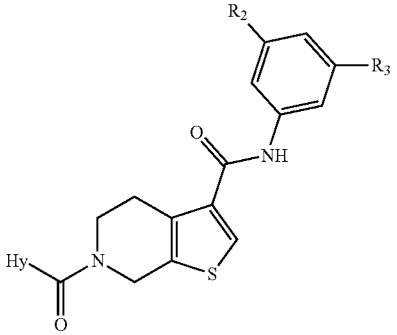

wherein Hy, $R_2$ and $R_3$ are as defined above.

In a particularly preferred embodiment, the present invention relates to a compound of general formula (Iab) wherein $R_2$ is trifluoromethyl.

In another particularly preferred embodiment, the present invention relates to a compound of general formula (Iab) wherein $R_3$ is fluorine.

In a further preferred embodiment, the present invention relates to a compound of general formula (Iab) wherein Hy is 1-methyl-1H-imidazole-5-yl. According to a preferred embodiment, the invention refers to the compound of Formula (Jab) in the Table 7 below and pharmaceutically acceptable salts thereof.

TABLE 7

List of compounds of Formula (Iab)

| Example No. | Structure | Chemical Name |
| --- | --- | --- |
| 49 | 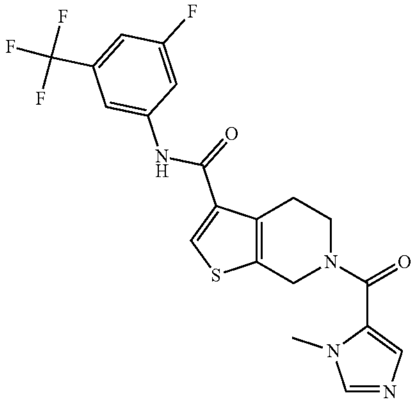 [SMILES: Cn1cncc1C(=O)N1CCc2c(C(=O)Nc3cc(F)cc(C(F)(F)F)c3)csc2C1] | N-(3-fluoro-5-(trifluoromethyl)phenyl)-6-(1-methyl-1H-imidazol-5-carbonyl)-4,5,6,7-tetrahydrothieno[2,3-c]pyridine-3-carboxamide |

In a further preferred embodiment, the present invention refers to a compound of formula (I) wherein $R_1$ is Het, represented by the formula (Ib)

(Ib)

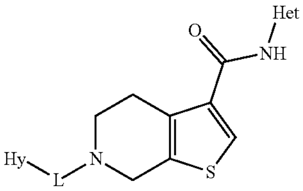

wherein

L is selected from the group consisting of —C(O)— and —$CH_2$—;

Hy is a monocyclic heteroaryl optionally substituted by one or more groups selected from —($C_1$-$C_4$)alkyl, halogen atoms, cyano, —$(CH_2)_nR_4R_5$, —O—($C_1$-$C_6$) alkyl, —($C_1$-$C_6$)haloalkyl, —NHC(O)—($C_1$-$C_6$)alkylene-O—($C_1$-$C_4$)alkyl and —NH-heteroaryl, wherein said heteroaryl is optionally substituted by one or more —($C_1$-$C_4$)alkyl;

Het is an heteroaryl optionally substituted by one or more groups selected from —($C_1$-$C_4$)alkyl, —($C_1$-$C_4$)haloalkyl and aryl, wherein said aryl is optionally substituted by one or more groups selected from —($C_1$-$C_4$)alkyl and halogen atoms; wherein $R_4$ is H;

$R_5$ is H or —($C_1$-$C_4$)alkyl;

and pharmaceutically acceptable salts thereof.

In another preferred embodiment the present invention refers to a compound of formula (Ib) wherein L is —$CH_2$—, represented by formula (Iba)

(Iba)

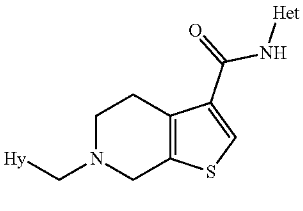

wherein Hy and Het are as defined above.

In a further preferred embodiment, the present invention relates to a compound of general formula (Iba) wherein Hy is selected from the group consisting of pyrimidin-5-yl, 3-aminopyrazin-2-yl, 5-methoxypyridin-3-yl, 5-fluoropyridin-3-yl, pyridin-3-yl, 3-aminopyrazin-2-yl and (2-((1-methyl-1H-pyrazol-4-yl)amino)pyrimidin-5-yl)methyl.

In another particularly preferred embodiment, the present invention relates to a compound of general formula (Iba) wherein Het is selected from the group consisting of 5-(1,1,1-trifluoro-2-methylpropan-2-yl)isoxazol-3-yl, (trifluoromethyl)pyridin-3-yl, 2-((dimethylamino)methyl)-6-(trifluoromethyl)pyridin-4-yl, 5-(trifluoromethoxy)pyridin-3-yl and 3-(tert-butyl)-1-methyl-1H-pyrazol-5-yl.

According to a preferred embodiment, the invention refers to at least one of the compounds of Formula (Iba) listed in the Table 4 below and pharmaceutically acceptable salts thereof. These compounds are particularly active on receptors DDR1 and DDR2, as shown in Table 5.

TABLE 4

| List of compounds of Formula (Iba) | | |
|---|---|---|
| Example No. | Structure | Chemical Name |
| 6 | 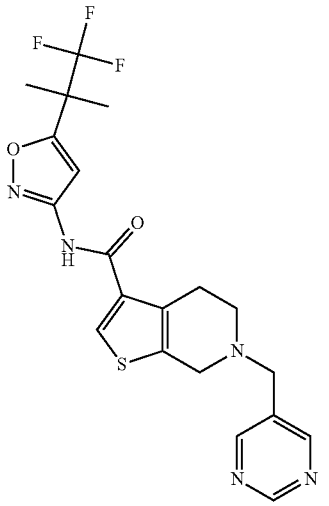 [SMILES: CC(C)(c1cc(NC(=O)c2csc3c2CCN(Cc2cncnc2)C3)no1)C(F)(F)F] | 6-(pyrimidin-5-ylmethyl)-N-(5-(1,1,1-trifluoro-2-methylpropan-2-yl)isoxazol-3-yl)-4,5,6,7-tetrahydrothieno[2,3-c]pyridine-3-carboxamide |
| 15 | 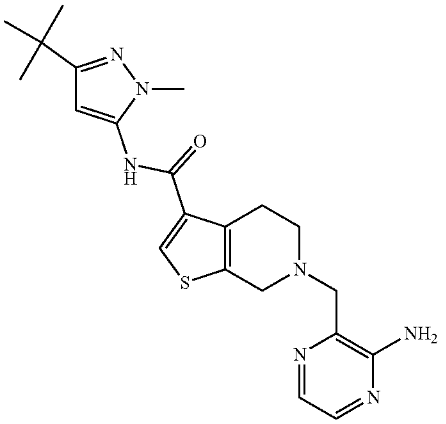 [SMILES: Cn1nc(C(C)(C)C)cc1NC(=O)c1csc2c1CCN(Cc1nccnc1N)C2] | 6-((3-aminopyrazin-2-yl)methyl)-N-(3-(tert-butyl)-1-methyl-1H-pyrazol-5-yl)-4,5,6,7-tetrahydrothieno[2,3-c]pyridine-3-carboxamide |
| 16 | 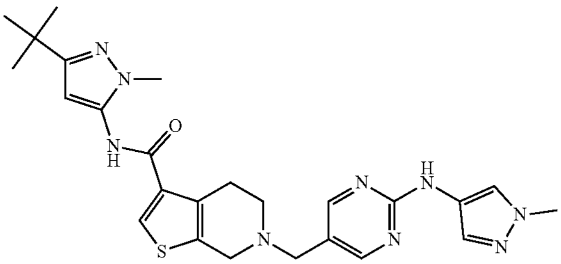 [SMILES: Cn1cc(Nc2ncc(CN3CCc4c(C(=O)Nc5cc(C(C)(C)C)nn5C)csc4C3)cn2)cn1] | N-(3-(tert-butyl)-1-methyl-1H-pyrazol-5-yl)-6-((2-((1-methyl-1H-pyrazol-4-yl)amino)pyrimidin-5-yl)methyl)-4,5,6,7-tetrahydrothieno[2,3-c]pyridine-3-carboxamide |

TABLE 4-continued

| List of compounds of Formula (Iba) | | |
|---|---|---|
| Example No. | Structure | Chemical Name |
| 26 | 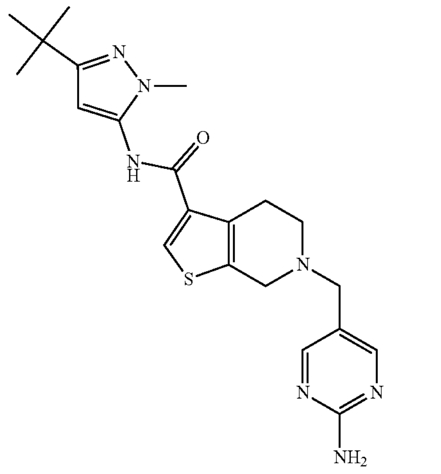 [SMILES: Cn1nc(C(C)(C)C)cc1NC(=O)c1csc2c1CCN(Cc1cnc(N)nc1)C2] | 6-((2-aminopyrimidin-5-yl)methyl)-N-(3-(tert-butyl)-1-methyl-1H-pyrazol-5-yl)-4,5,6,7-tetrahydrothieno[2,3-c]pyridine-3-carboxamide |
| 32 | 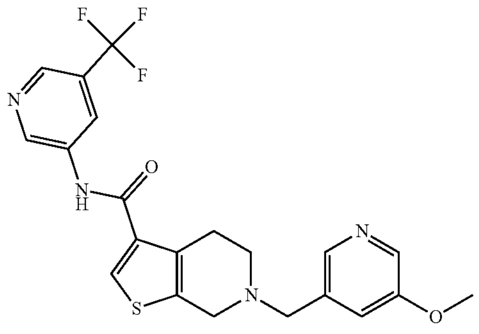 [SMILES: COc1cncc(CN2CCc3c(C(=O)Nc4cncc(C(F)(F)F)c4)csc3C2)c1] | 6-((5-methoxypyridin-3-yl)methyl)-N-(5-(trifluoromethyl)pyridin-3-yl)-4,5,6,7-tetrahydrothieno[2,3-c]pyridine-3-carboxamide |
| 33 | 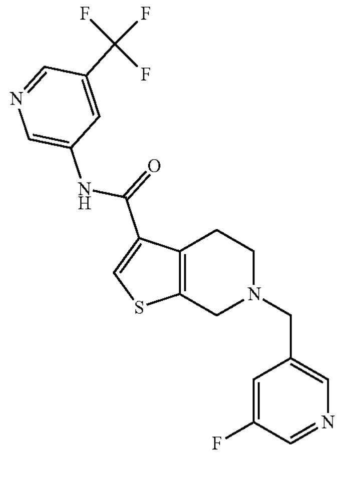 [SMILES: O=C(Nc1cncc(C(F)(F)F)c1)c1csc2c1CCN(Cc1cncc(F)c1)C2] | 6-((5-fluoropyridin-3-yl)methyl)-N-(5-(trifluoromethyl)pyridin-3-yl)-4,5,6,7-tetrahydrothieno[2,3-c]pyridine-3-carboxamide |

TABLE 4-continued

| List of compounds of Formula (Iba) | | |
|---|---|---|
| Example No. | Structure | Chemical Name |
| 34 | 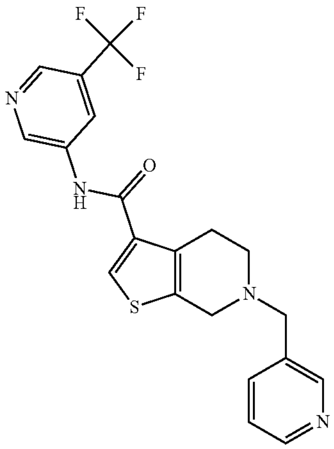 [SMILES: O=C(Nc1cncc(C(F)(F)F)c1)c1csc2c1CCN(Cc1cccnc1)C2] | 6-(pyridin-3-ylmethyl)-N-(5-(trifluoromethyl)pyridin-3-yl)-4,5,6,7-tetrahydrothieno[2,3-c]pyridine-3-carboxamide |
| 35 | 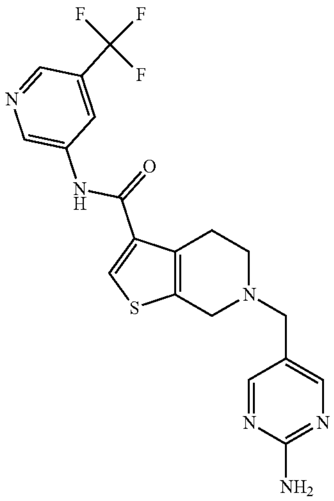 [SMILES: Nc1ncc(CN2CCc3c(C(=O)Nc4cncc(C(F)(F)F)c4)csc3C2)cn1] | 6-((2-aminopyrimidin-5-yl)methyl)-N-(5-(trifluoromethyl)pyridin-3-yl)-4,5,6,7-tetrahydrothieno[2,3-c]pyridine-3-carboxamide |
| 36 | 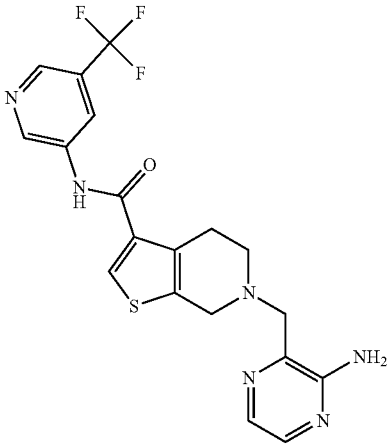 [SMILES: Nc1nccnc1CN1CCc2c(C(=O)Nc3cncc(C(F)(F)F)c3)csc2C1] | 6-((3-aminopyrazin-2-yl)methyl)-N-(5-(trifluoromethyl)pyridin-3-yl)-4,5,6,7-tetrahydrothieno[2,3-c]pyridine-3-carboxamide |

TABLE 4-continued
| List of compounds of Formula (Iba) | | |
|---|---|---|
| Example No. | Structure | Chemical Name |
| 57 | 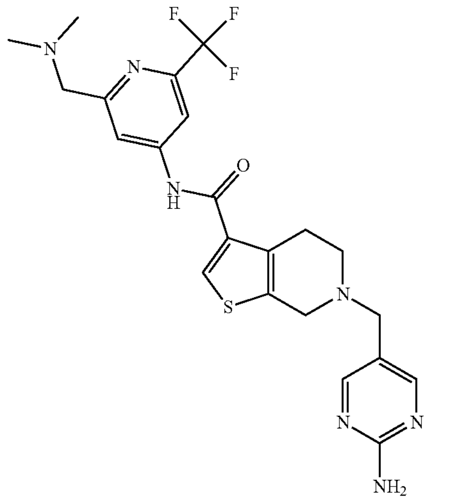 | 6-((2-aminopyrimidin-5-yl)methyl)-N-(2-((dimethylamino)methyl)-6-(trifluoromethyl)pyridin-4-yl)-4,5,6,7-tetrahydrothieno[2,3-c]pyridine-3-carboxamide |
| 60 | 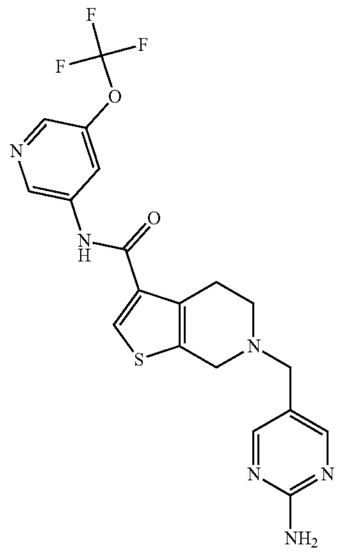 [SMILES: Nc1ncc(CN2CCc3c(C(=O)Nc4cncc(OC(F)(F)F)c4)csc3C2)cn1] | 6-((2-aminopyrimidin-5-yl)methyl)-N-(5-(trifluoromethoxy)pyridin-3-yl)-4,5,6,7-tetrahydrothieno[2,3-c]pyridine-3-carboxamide |

TABLE 4-continued

| List of compounds of Formula (Iba) | | |
|---|---|---|
| Example No. | Structure | Chemical Name |
| 62 | 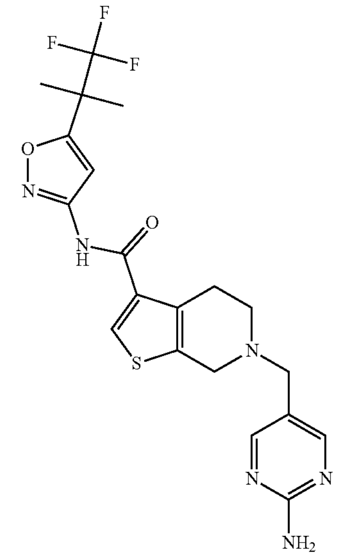 [SMILES: CC(C)(c1cc(NC(=O)c2csc3c2CCN(Cc2cnc(N)nc2)C3)no1)C(F)(F)F] | 6-((2-aminopyrimidin-5-yl)methyl)-N-(5-(1,1,1-trifluoro-2-methylpropan-2-yl)isoxazol-3-yl)-4,5,6,7-tetrahydrothieno[2,3-c]pyridine-3-carboxamide |
| 63 | 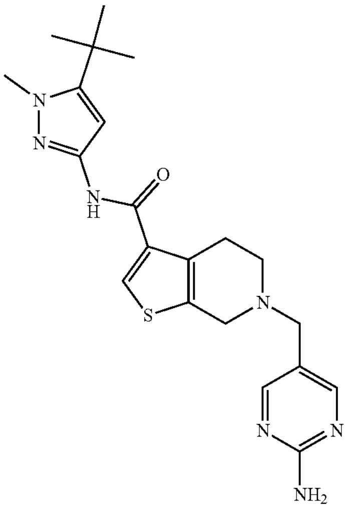 [SMILES: Cn1nc(NC(=O)c2csc3c2CCN(Cc2cnc(N)nc2)C3)cc1C(C)(C)C] | 6-((2-aminopyrimidin-5-yl)methyl)-N-(5-(tert-butyl)-1-methyl-1H-pyrazol-3-yl)-4,5,6,7-tetrahydrothieno[2,3-c]pyridine-3-carboxamide |
| 64 | 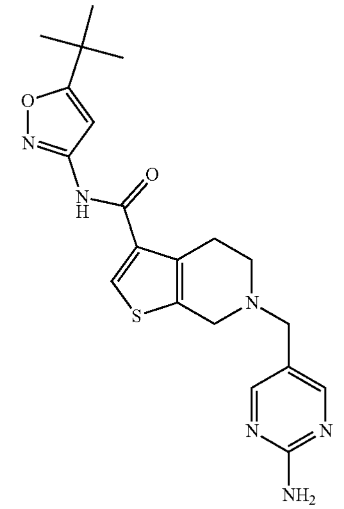 [SMILES: CC(C)(C)c1cc(NC(=O)c2csc3c2CCN(Cc2cnc(N)nc2)C3)no1] | 6-((2-aminopyrimidin-5-yl)methyl)-N-(5-(tert-butyl)isoxazol-3-yl)-4,5,6,7-tetrahydrothieno[2,3-c]pyridine-3-carboxamide |

TABLE 4-continued

| List of compounds of Formula (Iba) | | |
|---|---|---|
| Example No. | Structure | Chemical Name |
| 65 | 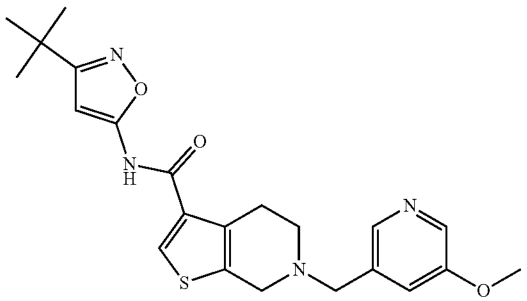 [SMILES: COc1cncc(CN2CCc3c(C(=O)Nc4cc(C(C)(C)C)no4)csc3C2)c1] | N-(3-(tert-butyl)isoxazol-5-yl)-6-((5-methoxypyridin-3-yl)methyl)-4,5,6,7-tetrahydrothieno[2,3-c]pyridine-3-carboxamide |

In a further preferred embodiment the present invention refers to a compound of formula (Ib) wherein L is —C(O)—, represented by formula (Ibb)

(Ibb)

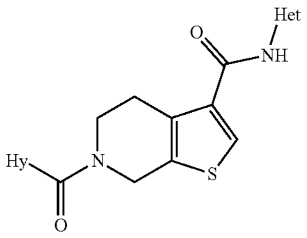

wherein Hy and Het are as defined above.

The compounds of the invention, including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be obtained using the methods described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

In some cases, generally known protective groups (PG) could be employed when needed to mask or protect sensitive or reactive moieties, in accordance to general principles of chemistry (Protective group in organic syntheses, 3rd ed. T. W. Greene, P. G. M. Wuts).

The compounds of formula (I) of the present invention have surprisingly been found to effectively inhibit both receptor DDR1 and DDR2. Advantageously, the inhibition of receptors DDR1 and DDR2 may result in efficacious treatment of the diseases or condition wherein the DDR receptors are involved.

In this respect, it has now been found that the compounds of formula (I) of the present invention have an antagonist drug potency expressed as inhibition constant Ki on DDR1 and DDR2 lower than 80 nM, as shown in the present experimental part.

Preferably, the compounds of the present invention have a Ki on DDR1 and DDR2 lower than 50 nM. Even more preferably, the compounds of the present invention have a Ki on DDR1 and DDR2 lower than 25 nM.

In addition, it has been found that the compounds of formula (I) of the present invention have the affinity for both DDR1 and DDR2 receptors and the inhibitory activity against both DDR1 and DDR2 receptors below about 80 nM respectively in the binding (expressed as Ki) and the cell based assays (expressed as IC50), as shown in the experimental part. Preferably, the compounds of the present invention have a Ki and/or an IC50 on DDR1 and DDR2 receptors lower than 50 nM. Even more preferably, the compounds of the present invention have a Ki and/or an IC50 on DDR1 and DDR2 receptors lower than 25 nM.

In one aspect, the present invention refers to a compound of formula (I) according to any of the embodiments disclosed above for use as a medicament.

In a preferred embodiment, the invention refers to a compound of formula (I) and pharmaceutically acceptable salts thereof, for use in treating diseases, disorders, or conditions associated with dysregulation of DDR.

In another aspect, the invention refers to the use of a compound of formula (I) as above described in the preparation of a medicament for the treatment of disorders associated with dysregulation of DDR.

In a preferred embodiment, the invention refers to a compound of formula (I) or a pharmaceutically acceptable salt thereof, for use in the prevention and/or treatment of a disease, disorder or condition associated with DDR receptor mechanism. In one embodiment, the present invention refers to a compound of formula (I) useful for the prevention and/or treatment of fibrosis and/or diseases, disorders, or conditions that involve fibrosis.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Preferably, the compounds of formula (I) as above described are useful for the treatment and/or prevention of fibrosis such as pulmonary fibrosis, idiopathic pulmonary fibrosis (IPF), hepatic fibrosis, renal fibrosis, ocular fibrosis, cardiac fibrosis, arterial fibrosis and systemic sclerosis.

More preferably, the compounds of formula (I) as above described are for the treatment of idiopathic pulmonary fibrosis (IPF).

In one aspect, the invention also refers to a method for the prevention and/or treatment of disorders associated with DDR receptors mechanisms, said method comprises administering to a patient in need of such treatment a therapeutically effective amount of a compound of formula (I) as above described.

In a further aspect, the invention refers to the use of a compound of formula (I) as above described for the treatment of disorders associated with DDR receptors mechanism.

In another aspect, the invention refers to the use of a compound of formula (I) as above described in the preparation of a medicament for the treatment of disorders associated with DDR receptors mechanism.

In a further aspect, the invention refers to a method for the prevention and/or treatment of disorder or condition associated with dysregulation of DDR receptors 1 and 2, said method comprising administering a patient in need of such treatment a therapeutically effective amount of a compound of formula (I) as above described.

In a further aspect, the present invention refers to the use of a compound of formula (I) as above described for the treatment of a disease, disorder or condition associated with dysregulation of DDR receptors 1 and 2.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects and it can nevertheless be routinely determined by the skilled artisan.

The compounds of formula (I) may be administered once or according to a dosing regimen wherein a number of doses are administered at varying intervals of time for a given period of time. Typical daily dosages may vary depending upon the route of administration chosen.

The present invention also refers to a pharmaceutical composition comprising a compound of formula (I) according to any of its embodiment in admixture with at least one or more pharmaceutically acceptable carrier or excipient.

In one embodiment, the invention refers to a pharmaceutical composition of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the invention and their pharmaceutical compositions may be accomplished according to patient needs, for example, orally, nasally, parenterally (subcutaneously, intravenously, intramuscularly, intrasternally and by infusion) and by inhalation.

Preferably, the compounds of the present invention are administered orally or by inhalation.

In one preferred embodiment, the pharmaceutical composition comprising the compound of formula (I) is a solid oral dosage form such as tablets, gelcaps, capsules, caplets, granules, lozenges and bulk powders.

In one embodiment, the pharmaceutical composition comprising the compound of formula (I) is a tablet.

The compounds of the invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like.

In a further embodiment, the pharmaceutical composition comprising a compound of formula (I) is a liquid oral dosage forms such as aqueous and non-aqueous solutions, emulsions, suspensions, syrups, and elixirs. Such liquid dosage forms can also contain suitable known inert diluents such as water and suitable known excipients such as preservatives, wetting agents, sweeteners, flavorants, as well as agents for emulsifying and/or suspending the compounds of the invention.

In a further embodiment, the pharmaceutical composition comprising the compound of formula (I) is an inhalable preparation such as inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers.

The compounds of the invention can be administered as the sole active agent or in combination with other pharmaceutical active ingredients.

The dosages of the compounds of the invention depend upon a variety of factors including among others the particular disease to be treated, the severity of the symptoms, the route of administration and the like.

The invention is also directed to a device comprising a pharmaceutical composition comprising a compound of Formula (I) according to the invention, in form of a single- or multi-dose dry powder inhaler or a metered dose inhaler.

All preferred groups or embodiments described above for compounds of formula (I) may be combined among each other and apply as well mutatis mutandis.

The compounds of the invention, including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be obtained using the methods described herein or by using other known methods, reagents and starting materials. When typical or preferred process conditions (i.e. reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes described below and reported in the following schemes should not be viewed as limiting the scope of the synthetic methods available for the preparation of the compounds of the invention.

The compounds of formula (I) including all the compounds or at least one of the here above listed can be generally prepared according to the procedure outlined in detail in the Schemes shown below, using generally known methods.

In a first embodiment of the present invention, compounds of formula (I) wherein $R_1$, L and Hy are as defined above, can be prepared as described in Scheme 1.

Compounds of formula (I) may be prepared according to Scheme 1 as described hereinafter providing at least one non-limiting synthetic route for the preparation of all examples.

Scheme 1
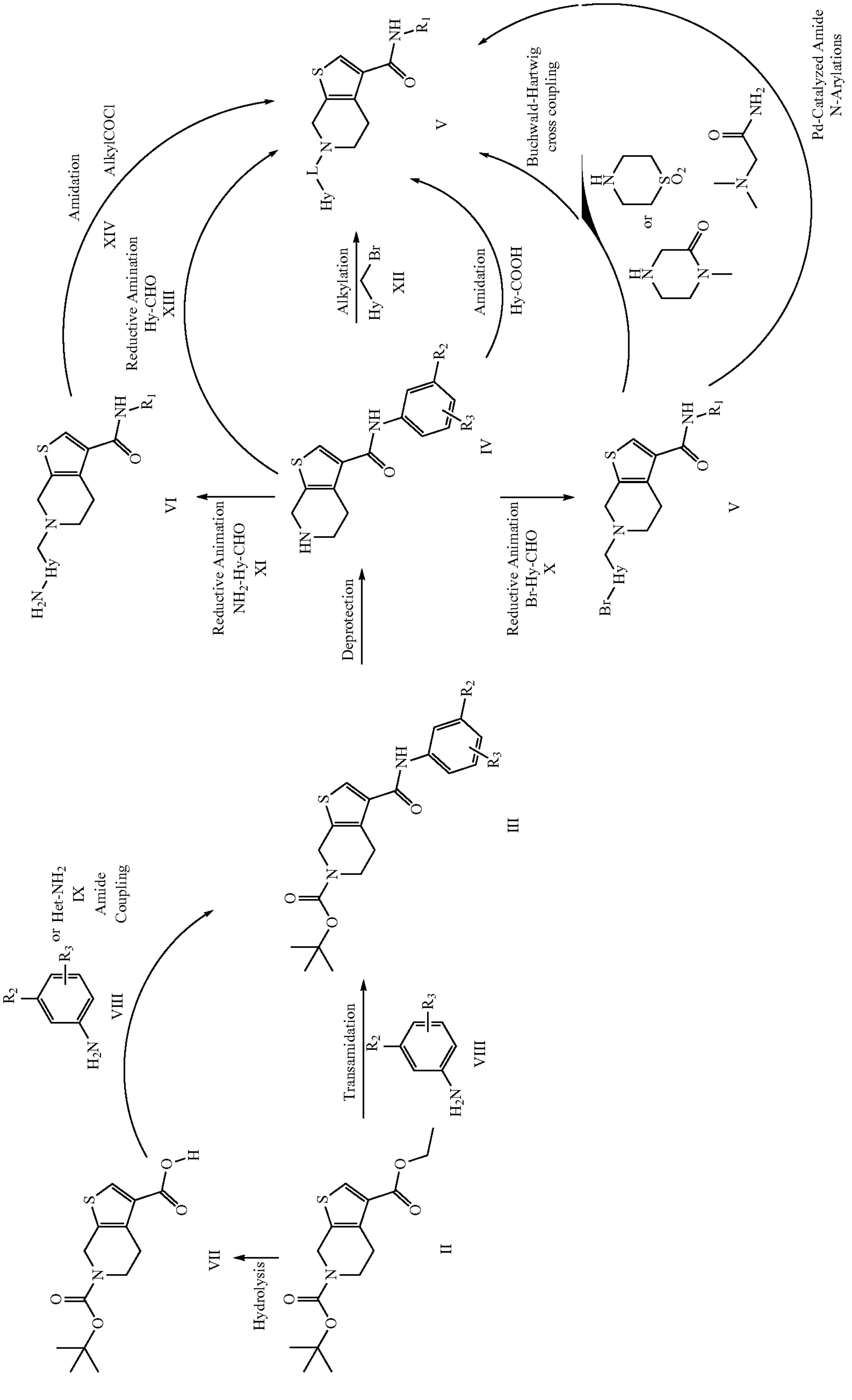

According to Scheme 1, Intermediate III may be prepared following a one-step synthesis starting from intermediate II, under direct amidation of esters (transamidation) conditions, using for example butyllithium as a promoter in a suitable organic solvent, such as THE or Dioxane, at a temperature ranging from −78° C. to room temperature for few hours. Intermediate IV can be obtained from intermediate III under suitable deprotection conditions, using for example aqueous HCl or HCl in Dioxane or TFA, in a suitable solvent, such as DCM, at a suitable temperature ranging from 0° C. to room temperature. Applying suitable alkylation conditions with the appropriate alkylbromide intermediate XII, for example using a suitable base, such as DIPEA or TEA, in a suitable solvent, such as DMF or DMA, at room temperature, compounds of formula (I) can be obtained.

Alternatively, intermediate III can be prepared from intermediate II performing an hydrolysis using a suitable aqueous inorganic base, such as NaOH, in a suitable solvent, such as MeOH, at room temperature, followed by an amide coupling with the proper amine VIII or IX, under suitable amide coupling conditions, in the presence of an agent that activates the carboxylic acid partner, such as TBTU or HATU or T3P, and in the presence of an organic base such as DIPEA or TEA, in a suitable organic solvent, such as DCM or DMF, and at a temperature generally around room temperature.

Alternatively, intermediate III can be prepared from intermediate II via amidation in the presence of TCFH and 1-methylimidazole to give the transient activated acylimidazolinium intermediate that is reacted with the appropriate amine VIII or IX in a solvent such as DMF, at RT. In a different approach, intermediate III can be prepared from intermediate II the presence of an appropriate chlorinating reagent, such as $POCl_3$ or thionyl chloride or oxalyl chloride, in a solvent such as pyridine or cyclopentylmethylether in the presence of a catalytic amount of DMF, at a temperature ranging from 5° C. to room temperature, to get the corresponding acyl chloride that is treated directly with the appropriate amine VIII or IX.

Differently, intermediate IV can be converted into intermediate V applying reductive amination conditions with the appropriate aldehyde X, with a suitable reducing agent, such as $Na(OAc)_3BH$ or $NaCNBH_3$, in a suitable solvent, such as DCM or EtOH, in the presence of an acid, such as acetic acid, and in the presence of a dehydrating agent, such as magnesium sulfate, if needed, or in the presence of a suitable coordinating agent, such as titanium tetrahydroisopropoxide, if needed, at a temperature ranging from room temperature to 50° C. Intermediate V can be converted into compounds of formula (I) performing a Buchwald-Hartwig cross-coupling with the appropriate amine using the suitable palladium catalyst, such as RuPhos Pd G3, and the suitable base, such as cesium carbonate, in a suitable solvent, such as DMF or Dioxane. Alternatively, Intermediate V can be converted into compounds of formula (I) performing a Pd-catalyzed amide N-arylation with the appropriate amide, using the suitable palladium catalyst, such as $Pd(dba)_2$, with a suitable ligand, such as XantPhos, in a suitable solvent, such as toluene, in the presence of a catalytic amount of aluminium triflate, at a temperature of 110° C.

In a different approach, intermediate VI can be prepared from intermediate V applying the suitable reductive amination conditions described above with the appropriate aldehyde XI and subsequently transformed into compounds of formula (I) via amidation with the proper acylchloride XIV using the suitable base, such as TEA or DIPEA, in a suitable solvent, such as THF, at room temperature. Compounds of formula (I) can also be obtained from intermediate IV following reductive amination conditions described above and using the appropriate aldehyde XIII. Differently, compounds of formula (I) can be prepared from intermediate IV via amidation with the proper carboxylic acid, applying the conditions described above.

In another embodiment, compounds of formula (I) may be prepared according to Scheme 2.

Scheme 2

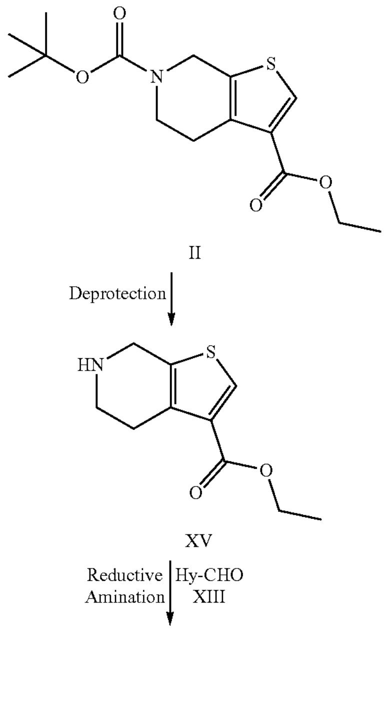

-continued

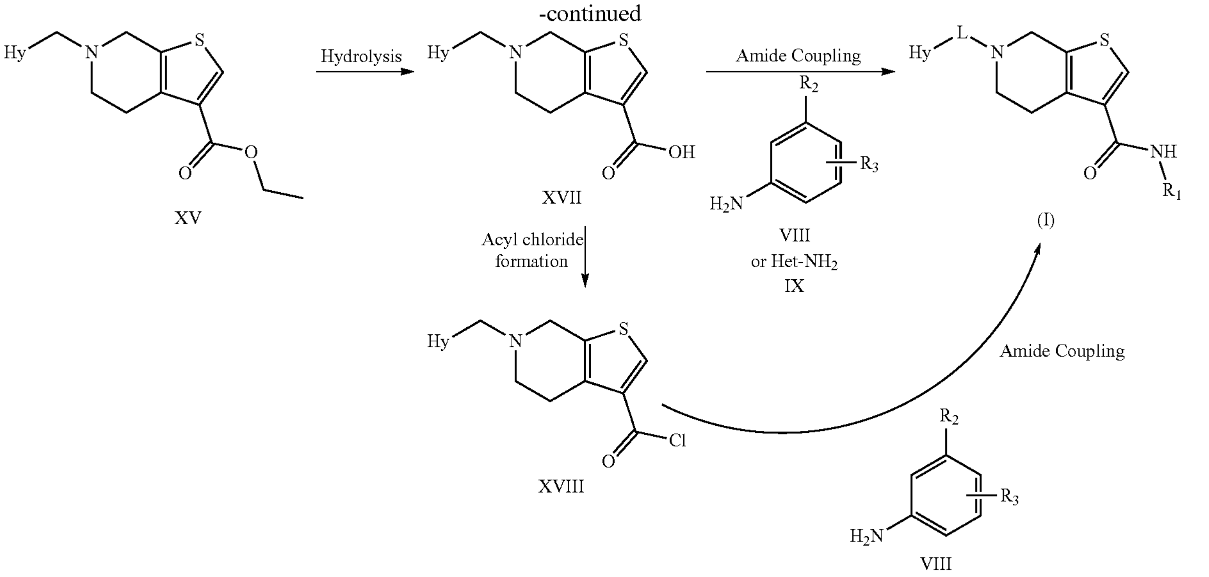

According to Scheme 2, intermediate XV can be obtained from intermediate II under suitable deprotection conditions, using for example aqueous HCl or HCl in Dioxane or TFA, in a suitable solvent, such as DCM or Diethyl Ether at a suitable temperature ranging from 0° C. to room temperature. Intermediate XV can undergo reductive amination to afford intermediate XVI, with the appropriate aldehyde XIII, with a suitable reductant agent, such as $Na(OAc)_3BH$ or $NaCNBH_3$, in a suitable solvent, such as DCM or EtOH, in the presence of an acid, such as acetic acid, and in the presence of a dehydrating agent, such as magnesium sulfate, if needed, or in the presence of a suitable coordinating agent, such as titanium tetrahydroisopropoxide, if needed, at a temperature ranging from room temperature to 50° C. Subsequently, compounds of formula (I) can be prepared from intermediate XVI performing an hydrolysis using a suitable aqueous inorganic base, such as NaOH, in a suitable solvent, such as MeOH, at room temperature, followed by an amide coupling with the proper amine VIII or IX, under suitable amide coupling conditions, in the presence of an agent that activates the carboxylic acid partner, such as TBTU or HATU or T3P, and in the presence of organic base such as DIPEA or TEA, in a suitable organic solvent such as DCM or DMF, and at a temperature generally around room temperature. Alternatively, compounds of formula (I) can be prepared from intermediate XVII the presence of an appropriate chlorinating reagent, such as $POCl_3$ or thionyl chloride or oxalyl chloride, in a solvent such as pyridine or cyclopentylmethyl ether, if needed, in the presence of a catalytic amount of DMF, if needed, at a temperature ranging from 5° C. to 50° C., to get the corresponding acyl chloride XVIII that may undergo an amide coupling with the appropriate amide VIII using the proper base, such as TEA, in a proper solvent, such as DCM, at around room temperature.

The various aspects of the invention described in this application are illustrated by the following examples which are not meant to limit the invention in any way.

PREPARATIONS OF INTERMEDIATES AND EXAMPLES

Chemical Names of the compounds were generated with Structure To Name Place IUPAC Name Name by PerkinElmer ChemDraw Professional 19.1.1.21. All reagents, for which the synthesis is not described in the experimental part, are either commercially available, or are known compounds or may be formed from known compounds by known methods by a person skilled in the art.

In the procedures that follow, some of the starting materials are identified through an “Intermediate” or “Example” number with indications on step number. This is provided merely for assistance to the skilled chemist.

A “similar” or “analogous” procedure means that such a procedure may involve minor variations, for example reaction temperature, reagent/solvent amount, reaction time, work-up conditions or chromatographic purification conditions.

Abbreviation—Meaning

RM=reaction mixture; TEA=triethylamine; HATU=(Dimethylamino)-N,N-dimethyl(3H-[1,2,3]triazolo[4,5-b]pyridin-3-yloxy)methaniminium hexafluorophosphate; DMAP=4-Dimetilamminopiridina; TCFH=Chloro-N,N,N',N'-tetramethylformamidinium hexafluorophosphate; DMF=N,N-dimethylformamide; $Et_2O$=diethyl ether; EtOAc=Ethyl acetate; THF=tetrahydrofuran; DCM=dichloromethane; ACN=acetonitrile; MeOH=methyl alcohol; IMS=Industrial methylated spirit; RT=room temperature; LCMS=Liquid Chromatography/Mass Spectrometry; HPLC=high pressure liquid chromatography; TLC=Thin Layer Chromatography; SCX=solid cation exchange; DMSO-d6=deuterated dimethyl sulfoxide. $CDCl_3$=deuterated chloroform; $NaBH_3CN$=sodium cyanoborohydride ACN-d3=deuterated acetonitrile; NMR=nuclear magnetic resonance; DIPEA=N,N-Diisopropylethylamine; HCOOH=formic acid; UPLC=Ultra Performance Liquid Chromatography; n-BuLi=n-butyllithium; RuPhos=2-Dicyclohexylphosphino-2',6'-diisopropoxybiphenyl; XantPhos=4,5-Bis(diphenylphosphino)-9,9-dimethylxanthene; $Pd(dba)_2$=Bis(dibenzylideneacetone)palladium (0); RuPhos Pd G3=(2-Dicyclohexylphosphino-2',6'-diisopropoxy-1,1'-biphenyl)[2-(2'-amino-1,1'-biphenyl)] palladium(II) methanesulfonate; STAB=sodium triacetoxyborohydride; AcOH=Acetic acid; T3P=Propanephosphonic acid anhydride; prep HPLC=preparative high performance liquid chromatography; pTLC=preparative thin layer chromatography; FCC=flash column chromatography; SM=starting material; eq.=equivalents.

General Experimental Details

NMR Characterization:

$^1$H NMR spectra were recorded on Varian MR-400 spectrometer operating at 400 MHZ (proton frequency), equipped with: a self-shielded Z-gradient coil 5 mm 1H/nX broadband probe head for reverse detection, deuterium digital lock channel unit, quadrature digital detection unit with transmitter offset frequency shift or on Bruker Avance III HD 400 MHz or on Bruker Fourier 300 MHz. Chemical shifts are reported as δ values in ppm relative to tetramethyl silane (TMS) as an internal standard. Coupling constants (J values) are given in hertz (Hz) and multiplicities are reported using the following abbreviations (s=singlet, d=doublet, t=triplet, q=quartet, dd=doublet of doublets, dt=doublet of triplets, m=multiplet, br=broad, nd=not determined).

In some cases, signals NH from amide bond or amine bond (Exchangeable protons) are not visible.

In a few cases, some signals could be hidden under the signal of water or under the signal of DMSO or other residual solvents.

LC/UV/MS Analytical Methods

LC/MS retention times are estimated to be affected by an experimental error of 0.5 min.

Method 1 Acquity CSH C18 column 50 mm×2.1 mm 1.7 μm, maintained at 40° C.; Mobile Phase: Eluent B (ACN/water 95:5+0.05% HCOOH) in Eluent A (water/ACN 95:5+0.05% HCOOH) from 1% to 99.9% within 3.5 min. Flow rate: 1 mL/min. Wavelength: 210-400 nm DAD. UPLC+Waters PDA+Waters QDA.

Method 2 Kinetex® XB-C18 column, 4.6×50 mm, 2.6 μm maintained at 25° C. Mobile phase: water (0.1% HCOOH) in ACN (0.1% HCOOH), from 80% to 5% within 3.90 min; Flow rate: 1.0 ml/min; wavelength: 190-340 nm DAD. Dionex UHPLC Ultimate 3000 with DAD detector/Thermo Scientific MSQ Plus.

Method 3 Kinetex® XB-C18 column, 4.6×50 mm, 2.6 μm maintained at 25° C. Mobile phase: water (0.1% HCOOH) in ACN (0.1% HCOOH), from 95% to 20% within 4.75 min; Flow rate: 1.0 ml/min; wavelength: 190-340 nm DAD. Dionex UHPLC Ultimate 3000 with DAD detector/Thermo Scientific MSQ Plus.

Method 4 Kinetex® XB-C18 column, 4.6×50 mm, 2.6 μm maintained at 25° C. Mobile phase: water (0.1% HCOOH) in ACN (0.1% HCOOH), from 90% to 5% within 3.90 min; Flow rate: 1.0 ml/min; wavelength: 190-340 nm DAD. Dionex UHPLC Ultimate 3000 with DAD detector/Thermo Scientific MSQ Plus.

Method 5 Kinetex® XB-C18 column, 4.6×50 mm, 2.6 μm maintained at 25° C. Mobile phase: water (0.1% HCOOH) in ACN (0.1% HCOOH), from 70% to 5% within 3.90 min; Flow rate: 1.0 ml/min; wavelength: 190-340 nm DAD. Dionex UHPLC Ultimate 3000 with DAD detector/Thermo Scientific MSQ Plus.

Method 6 Kinetex® XB-C18 column, 4.6×50 mm, 2.6 μm maintained at 25° C. Mobile phase: water (0.1% HCOOH) in ACN (0.1% HCOOH), from 70% to 5% within 3.90 min; Flow rate: 1.0 ml/min; wavelength: 190-340 nm DAD. Dionex UHPLC Ultimate 3000 with DAD detector/Thermo Scientific ISQ EC mass spectrometer.

Method 7 Kinetex® XB-C18 column, 4.6×50 mm, 2.6 μm maintained at 25° C. Mobile phase: water (0.1% HCOOH) in ACN (0.1% HCOOH), from 80% to 5% within 3.90 min; Flow rate: 1.0 ml/min; wavelength: 190-340 nm DAD. Dionex UHPLC Ultimate 3000 with DAD detector/Thermo Scientific ISQ EC mass spectrometer.

Method 8 Acquity UPLC BEH Shield RP18 column, 100×2.1 mm, 1.72 μm (Plus guard cartridge), maintained at 40° C. Mobile phase: ACN in water+10 nM ammonium bicarbonate from 5% to 95% within 5.6 min. Flow rate: 0.4 ml/min. Wavelength: 210-400 nm DAD. UPLC+Waters DAD+Waters SQD2, single quadrapole UPLC-MS Method 9 Acquity UPLC HSS C18 column, 100×2.1 mm, 1.8 μm (Plus guard cartridge), maintained at 40° C. Mobile phase: ACN (0.1% HCOOH) in water (0.1% HCOOH) from 5% to 95% within 5.6 min. Flow rate: 0.4 ml/min. Wavelength: 210-400 nm DAD. UPLC+Waters DAD+Waters SQD2, single quadrapole UPLC-MS Method 10: Acquity UPLC BEH C18 column, 100×2.1 mm, 1.7 μM, maintained at 40° C. Mobile phase: ACN (0.03% $NH_3$) in water (0.03% $NH_3$), from 5% to 95% within 5.6 min; Flow rate: 0.4 ml/min; Wavelength: 100-800 nm DAD. Acquity UPLC with PDA detector and ZQ Mass Spectrometer.

Method 11: Agilent Zorbax column 4.6×50 mm, 3.5 μm, maintained at 40° C. Mobile phase: ACN (0.1% HCOOH) in water (0.1% HCOOH), from 5% to 95% within 2 min. Flow rate: 3.0 ml/min. Wavelength: 210-400 nm DAD. Waters 2795/2695 separations module+Waters DAD+Micromass ZQ, single quadrapole LC-MS.

Method 12: Acquity BEH UPLC column, 2.1×50 mm, 1.7 μm, maintained at 40° C. Mobile phase: ACN (0.03% $NH_3$) in water (0.03% $NH_3$), from 8% to 97% within 1.5 min; Flow rate: 0.8 ml/min; Wavelength: 210-400 nm DAD. Acquity H-Class UPLC with PDA detector and QDa.

Method 13: Waters Sunfire C18 column, 4.6×50 mm, 3.5 μm, maintained at 40° C. Mobile phase ACN in water+10 mM ammonium bicarbonate, from 5 to 95% within 2.5 mins. Flow rate: 2.0 ml/min. Wavelength: 210-400 nm DAD. Waters 2795 separations module+Waters DAD+Micromass ZQ, single quadrapole LC-MS Where the preparation of starting materials is not described, these are commercially available, known in the literature, or readily obtainable by those skilled in the art using standard procedures. All solvents were purchased from commercial sources and were used without additional purification.

Preparative HPLC was performed using reversed phase (C18) preparative HPLC both in basic conditions (ACN+0.1% $NH_3$, $H_2O$+0.1% $NH_3$) and in acidic conditions (ACN+0.1% HCOOH, H O+0.1% HCOOH), in the last case, the residue was triturated with $NaHCO_3$ (15% aq. sol.), then the precipitate was filtered through the Schott funnel, rinsed with water, transferred to the vial and dried on high vacuum overnight at RT or alternatively SCX (NH) was utilized to obtained free base of the product, unless differently stated. Thin layer chromatography was performed on Merck silica gel 60 F254 TLC plates. Preparative thin-layer chromatography (pTLC) was performed with Uniplate 1000 micron or 500 micron silica gel plates. Flash chromatography was performed.

General Synthetic Procedures

General Procedure A

To a mixture of the required carboxylic acid (1.00 eq) and HATU (1.20 to 2.00 eq) in DMF (0.1M concentration) N,N-diisopropylethylamine (3.00 to 8.00 eq) was added. The reaction mixture was stirred at RT for 15 minutes then the required amine (1.00 eq) was added. The reaction mixture was stirred at RT until LCMS indicated consumption of starting material and then concentrated.

General Procedure B

The required carboxylic acid (1.00 eq) was suspended in thionyl chloride (30 eq) and the reaction mixture was stirred at 50° C. for 2 h. The reaction mixture was allowed to cool to RT and concentrated under vacuum. The residue was suspended in toluene and re-concentrated to give the intermediate acyl chloride. To a solution of the required aniline (1.00 eq) and TEA (3.00 eq) in DCM (0.1M concentration), the acyl chloride was added. The reaction mixture was stirred at RT until LCMS indicated consumption of starting material and then concentrated under vacuum.

General Procedure C

To a solution of the required amine (1.00 eq) and the required aldehyde (1.00 eq) in MeOH (0.03M concentration) titanium(IV) isopropoxide (3.00 eq) was added and refluxed for 2 h. The reaction cooled to RT and $NaBH_3CN$ (2.50 eq) was added and stirring continued at RT overnight. The reaction was quenched with water, filtered through celite and concentrated under vacuum.

General Procedure D

To a solution of the required aldehyde (1.00 eq) in DCM (0.1 M concentration) was added the required amine (1.10 eq), titanium(IV) isopropoxide (2.00 eq) and AcOH (3.00 eq). The reaction mixture was stirred at room temperature for 1 h. STAB (2.00 eq) was added and the reaction mixture was stirred at room temperature until LCMS indicated consumption of starting material. The residue was loaded onto an Isolute SCX-II cartridge, washed with MeOH, then released with 2M $NH_3$/MeOH. The eluate was concentrated under vacuum.

General Procedure E

STAB (2.00 eq) was added to a mixture of aldehyde (1.25 eq), amine (1.00 eq), AcOH (0.01 eq) and $MgSO_4$ (4.00 eq) in DCM (15.00 mL) and the mixture stirred for at room temperature until LCMS indicated consumption of starting material. The mixture was partitioned between saturated $NaHCO_3$ (aq) and DCM, then re-extracted with DCM. The combined organic extracts were dried ($Na_2SO_4$) and concentrated under vacuum.

General Procedure F

To a mixture of the required aldehyde (1.00 eq) and the required amine (1.00 eq) in MeOH (0.075 M concentration) was added AcOH (10 eq) and the reaction mixture was stirred at 65° C. for 90 mins. The reaction mixture was cooled to room temperature and concentrated under vacuum. The residue was suspended in DCM (0.025 M concentration) and sodium STAB (3.50 eq) was added. The reaction mixture was stirred at room temperature for 18 hours. The reaction mixture was diluted with DCM and treated with a 10% sol of $KHSO_{4(aq)}$. After stirring for 15 minutes, the mixture was basified with saturated aqueous $Na_2CO_3$ and the layers separated. The aqueous layer was extracted with DCM and the combined organic extracts filtered through a hydrophobic frit and concentrated under vacuum.

General Procedure G

To a solution of the required acid (1.00 eq), the required amine (1.00 to 1.30 eq) and 1-methylimidazole (3.50 eq) in ACN (0.2M concentration), TCFH (1.20 to 1.50 eq) was added. The reaction mixture was stirred at room temperature until LCMS indicated consumption of starting material and partitioned between saturated $NaHCO_{3(aq)}$ and EtOAc. The phases were separated, the aqueous phase was extracted with 2×EtOAc and the combined organic phases were passed through a hydrophobic frit and concentrated under vacuum.

General Procedure H

To a mixture of the required aldehyde (1.00 eq) and the required amine (1.50 eq) in DMF (0.075 M concentration) was added AcOH (2.00 eq) and $MgSO_4$ (2.00 eq). The reaction mixture was stirred at room temperature for 1 hr followed by addition of STAB (2.00 eq). The reaction mixture was heated at 60° C. overnight. The reaction was partitioned between DCM and aqueous $NaHCO_3$. The combined organic phases were filtered through a hydrophobic frit and the solvent was concentrated under vacuum.

Preparation of Intermediate 1: 2-((1-methyl-1H-pyrazol-4-yl)amino)pyrimidine-5-carbaldehyde

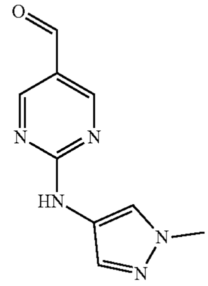

Step 1; 2-((1-methyl-1H-pyrazol-4-yl)amino)pyrimidine-5-carbaldehyde 2-chloropyrimidine-5-carbaldehyde (50 mg, 0.351 mmol) was dissolved in THF (3.5 mL), then 1-methyl-1H-pyrazol-4-amine (41 mg, 0.421 mmol) was added. Reaction mixture was stirred overnight at RT. The mixture was quenched with addition of DCM and brine. The phases were separated and the water layer was washed with DCM (×2). All combined organic phases were dried over $Na_2SO_4$, filtered and concentrated. Crude material was purified by FCC eluting with Hexane/EtOAc 1:1 to give the titled product (35 mg, 39%).

$^1H$ NMR (300 MHz, DMSO-d6) δ 10.45 (s, 1H), 9.80 (s, 1H), 8.92-8.79 (m, 2H), 7.99 (d, J=0.8 Hz, 1H), 7.56 (d, J=0.8 Hz, 1H), 3.83 (s, 3H).

Preparation of Intermediate 20: 2-(oxetan-3-ylamino)pyrimidine-5-carbaldehyde

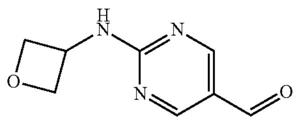 [SMILES: O=Cc1cnc(NC2COC2)nc1]

Step 1: 2-(oxetan-3-ylamino)pyrimidine-5-carbaldehyde

To a solution of 2-chloropyrimidine-5-carbaldehyde (50 mg, 0.351 mmol, 1.00 eq) in DMSO (1.5 mL), TEA (0.049 mL, 0.351 mmol, 1.00 eq) and 3-aminooxetane (0.027 mL, 0.386 mmol, 1.10 eq) were added and the solution was stirred at 60° C. for 2 hours. The reaction mixture was allowed to cool to room temperature, diluted with DCM and washed with water and brine. The organic layer was dried ($MgSO_4$) and concentrated to afford the tile compound (62 mg, 100%).

LC-MS (ESI): m/z (M+1)=180.2; $t_R$=1.00 min Method 11

Preparation of Intermediate 21: 2-((2-methoxyethyl)amino)pyrimidine-5-carbaldehyde

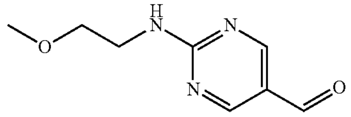

Step 1: 2-chloro-5-(diethoxymethyl)pyrimidine (Intermediate 22)

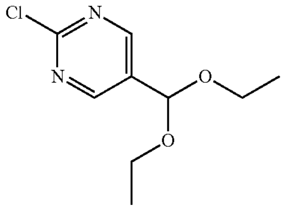

To a suspension of 2-chloropyrimidine-5-carbaldehyde (3000 mg, 21.0 mmol, 1.00 eq) and p-toluenesulfonic acid monohydrate (400 mg, 2.10 mmol, 0.10 eq) in EtOH (60 mL) triethyl orthoformate (11 mL, 63.1 mmol, 3.00 eq) was added and the mixture was heated to 80° C. and stirred for 3 hours. The mixture was cooled to 0° C. and 10 mL of saturated aqueous $NaHCO_3$ was added and the EtOH was evaporated. The resulting suspension was extracted with EtOAc and the organics were combined, dried ($MgSO_4$) and concentrated. The residue was purified by FCC on silica gel (120 g, 0-20% EtOAc in cyclohexane) to afford the title compound (3760 mg, 17.4 mmol, 82%).

$^1$H NMR (400 MHz, DMSO-d6) δ 8.77 (s, 2H), 5.70 (s, 1H), 3.65-3.56 (m, 4H), 1.19 (t, J=7.1 Hz, 6H).

Step 2: 5-(diethoxymethyl)-N-(2-methoxyethyl) pyrimidin-2-amine (Intermediate 23)

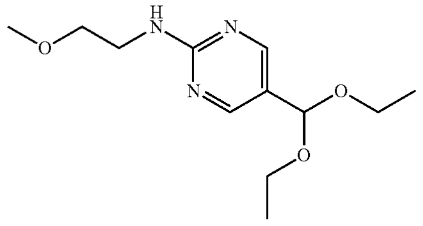 [SMILES: CCOC(OCC)c1cnc(NCCOC)nc1]

To a solution of Intermediate 22 (200 mg, 0.923 mmol, 1.00 eq) and 2-methoxyethylamine (80 μL, 0.923 mmol, 1.00 eq) in DMF (3.0 mL) $K_2CO_3$ (319 mg, 2.31 mmol, 2.50 eq) was added and the mixture was stirred at 80° C. for 2 hours. The reaction mixture was diluted with EtOAc and washed with water, 1:1 water/brine and brine, dried over $MgSO_4$, and concentrated. The residue was purified by silica FCC (12 g, 0-80% EtOAc in cyclohexane) to afford the title compound (103 mg, 44%)

$^1$H NMR (400 MHz, DMSO-d6) δ 8.25 (s, 2H), 7.23 (dd, J=5.5, 5.5 Hz, 1H), 5.42 (s, 1H), 3.57-3.44 (m, 8H), 3.26 (s, 3H), 1.16 (t, J=7.0 Hz, 6H).

Step 3: 2-((2-methoxyethyl)amino)pyrimidine-5-carbaldehyde (Intermediate 21)

To a solution of Intermediate 23 (101 mg, 0.396 mmol, 1.00 eq) in THE (1.0 mL) was added a solution of 1 M HCl (21 mL, 20.6 mmol, 52.0 eq) and the mixture was stirred at rt for 5 hours then at 50° C. overnight. The mixture was cooled in an ice bath and basified with 2M aq. NaOH to ~pH 13. The aqueous layer was extracted with EtOAc and the combined organics were dried ($MgSO_4$), concentrated to afford the title compound (60 mg, 84%)

$^1$H NMR (400 MHz, DMSO-d6) δ 9.74 (s, 1H), 8.77 (d, J=2.9 Hz, 1H), 8.71 (d, J=2.9 Hz, 1H), 8.36 (t, J=5.3 Hz, 1H), 3.57-3.47 (m, 4H), 3.27 (s, 3H).

Preparation of Intermediate 24: 2-(2-hydroxyethylamino)pyrimidine-5-carbaldehyde

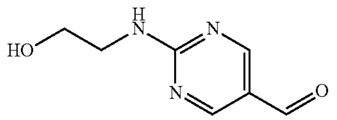 [SMILES: O=Cc1cnc(NCCO)nc1]

Step 1: 2-[[5-(diethoxymethyl)pyrimidin-2-yl] amino]ethanol (Intermediate 25)

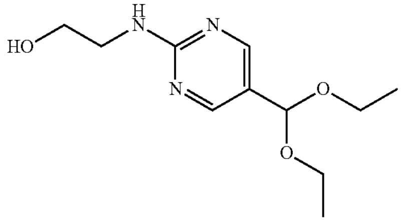 [SMILES: CCOC(OCC)c1cnc(NCCO)nc1]

To a solution of 2-chloro-5-(diethoxymethyl)pyrimidine (200 mg, 0.923 mmol, 1.00 eq) and ethanolamine (0.056 mL, 0.923 mmol, 1.00 eq) in DMF (3.00 mL) was added $K_2CO_3$ (319 mg, 2.31 mmol, 2.50 eq) and the mixture was stirred at 80° C. for 2 hours. The reaction mixture was diluted in EtOAc and washed with water, 1:1 water/brine, brine, dried over $MgSO_4$, filtered and concentrated. The residue was purified by silica FCC (12 g, 0-100% EtOAc in c-Hex, 15 CV) to afford the title compound (63 mg, 28%).

$^1$H NMR (400 MHz, DMSO-d6) δ 8.24 (s, 2H), 7.14 (t, J=5.6 Hz, 1H), 5.42 (s, 1H), 4.67 (t, J=5.6 Hz, 1H), 3.59-3.45 (m, 6H), 3.38-3.34 (m, 2H), 1.16 (t, J=7.0 Hz, 6H)

Step 2: 2-(2-hydroxyethylamino)pyrimidine-5-carbaldehyde (Intermediate 24)

To a solution of Intermediate 25 (61 mg, 0.253 mmol, 1.00 eq) in THE (1.00 mL) was added a solution of 1M HCl in $H_2O$ (13 mL, 13.1 mmol, 52.0 eq) and the mixture was stirred at rt for 5 hours then at 50° C. overnight. The mixture was cooled in an ice bath and basified with 2M aq. NaOH to ~pH 13. The aqueous layer was extracted with EtOAc.

Most material stayed in the aqueous layer. This was concentrated and the solid triturated in MeOH. The dissolved material was combined with the organics extract and concentrated to afford the title compound (42 mg) Taken onto the next step without further purification assuming a quantitative yield LC-MS (ESI): m/z (M+1)=168.2; $t_R$=0.88 min Method 11

Preparation of Intermediate 26: 2-amino-4-methylpyrimidine-5-carbaldehyde

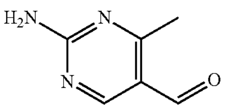

Step 1: (2-amino-4-methylpyrimidin-5-yl)methanol (Intermediate 27)

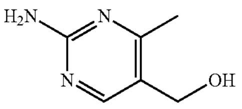

To a suspension of 2-amino-4-methyl-pyrimidine-5-carboxylic acid (250 mg, 1.63 mmol, 1.00 eq) in THE (12 mL) was added Isobutyl chloroformate (0.25 mL, 1.96 mmol, 1.20 eq) followed by 4-Methylmorpholine (0.22 mL, 1.96 mmol, 1.20 eq) at 0° C. After stirring for 2 hours the precipitate was removed by filtration. To the filtrate was added a solution of $NaBH_4$ (93 mg, 2.45 mmol, 1.50 eq) in water (0.60 mL) at 0° C. The reaction was allowed to warm to rt and stirred for 3 hours. The reaction mixture was diluted in EtOAc and washed with water, brine, dried over $MgSO_4$, filtered and concentrated. The residue was used in the next step directly.

Step 2: 2-amino-4-methylpyrimidine-5-carbaldehyde (Intermediate 26)

To a solution of Intermediate 27 (100%, 148 mg, 1.06 mmol, 1.00 eq) in THF (6.00 mL) was added Manganese (IV) oxide (462 mg, 5.32 mmol, 5.00 eq) and the mixture was stirred at rt overnight. The mixture was diluted in EtOAc, filtered through a pad of celite and concentrated. Crude product taken directly to the next step.

Preparation of Intermediate 28: (R)-1-(3-amino-5-(trifluoromethyl)benzyl)-N,N-dimethylpyrrolidin-3-amine

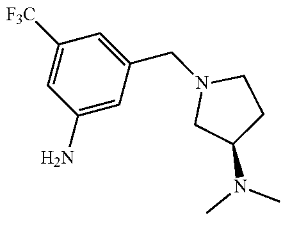 [SMILES: CN(C)[C@@H]1CCN(Cc2cc(N)cc(C(F)(F)F)c2)C1]

Step 1: (R)—N,N-dimethyl-1-(3-nitro-5-(trifluoromethyl)benzyl)pyrrolidin-3-amine (Intermediate 29)

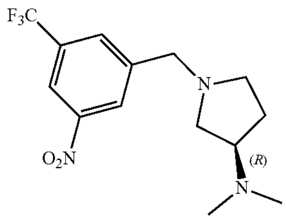

To a solution of 3-nitro-5-(trifluoromethyl)benzaldehyde (750 mg, 3.42 mmol) and (R)-(+)-3-(dimethylamino)pyrrolidine (478 uL, 3.77 mmol) in DCM (23.00 mL) at room temperature titanium(IV) isopropoxide (2.0 mL, 6.85 mmol) and AcOH (588 µL, 10.3 mmol) were added. The reaction mixture was stirred at room temperature for 1 h. STAB (1.45 g, 6.85 mmol) was then added and the reaction mixture stirred at room temperature for a further 2.5 h. The reaction mixture was quenched by addition of water and the phases were separated. The aqueous phase was adjusted to pH 9 by addition of NaOH and DCM was added. The combined phases were filtered through a Celite pad and then separated.

The aqueous phase was re-extracted with DCM and the combined organic phases were filtered through a hydrophobic frit and concentrated under vacuum. Purification by Silica FCC (24 g cartridge, 0-5% 2M $NH_3$/MeOH in DCM) to give the title compound (786 mg, 72%).

$^1H$ NMR (300 MHz, DMSO-d6) δ 8.43 (s, 1H), 8.38 (s, 1H), 8.13 (s, 1H), {3.86 (d, J=14.2 Hz, 1H), 3.73 (d, J=14.2 Hz, 1H), AB system}, 2.79-2.53 (m, 3H), 2.39-2.30 (m, 1H), 2.08 (s, 6H), 1.94-1.81 (m, 1H), 1.69-1.57 (m, 1H). 1H not observed and assumed to be overlapping with DMSO signal.

Step 2: (R)-1-(3-amino-5-(trifluoromethyl)benzyl)-N,N-dimethylpyrrolidin-3-amine (Intermediate 28)

To palladium (10% wt. on carbon, 79 mg, 0.739 mmol) was added a solution of Intermediate 29 (786 mg, 2.48 mmol) in IMS (24.5 mL). The reaction mixture was stirred at room temperature under an atmosphere of hydrogen for 2 h. The reaction mixture was filtered through celite and the filter bed washed with DCM. The filtrate was concentrated under vacuum to give the title compound (710 mg, 99%).

$^1H$ NMR (400 MHz, $CDCl_3$) δ 6.94 (s, 1H), 6.84 (s, 1H), 6.77 (s, 1H), 3.81 (s, 2H), 3.58 (d, J=13.2 Hz, 1H), 3.50 (d, J=13.3 Hz, 1H), 2.83-2.69 (m, 3H), 2.53-2.45 (m, 1H), 2.31 (dd, J=6.8, 8.3 Hz, 1H), 2.20 (s, 6H), 2.05-1.95 (m, 1H), 1.77-1.68 (m, 1H)

The intermediates reported in the following table were prepared via reductive amination as described for Intermediate 28, step 1-2, applying the corresponding, commercially amines and/or corresponding aryl aldehyde in step 1.

| Intermediate No | Structure | Step 1 SM Amount (yield) | Step 2 Final product amount (yield) | Data |
|---|---|---|---|---|
| 30 | 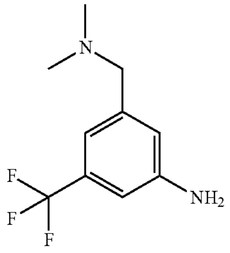 | dimethylamino (2M solution in THF): 0.50 mL, 1.00 mmol (1.1 eq) (84 mg, 37%) | 67 mg (91%) | $^1$H NMR (400 MHz, $CDCl_3$) δ 6.93 (s, 1H), 6.82 (s, 1H), 6.80 (s, 1H), 3.82 (s, 2H), 3.36 (s, 2H), 2.24-2.24 (m, 6H) |
| 31 | 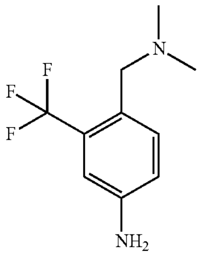 | 4-nitro-2-(trifluoromethyl) benzaldehyde: 125 mg, 0.570 mmol dimethylamino (2M solution in THF): 0.31 mL, 0.628 mmol (132 mg, 93%) | 104 mg (90%) | $^1$H NMR (400 MHz, $CDCl_3$) δ 7.45 (d, J = 8.5 Hz, 1H), 6.92 (d, J = 2.5 Hz, 1H), 6.81 (dd, J = 2.4, 8.3 Hz, 1H), 3.78 (s, 2H), 3.45 (s, 2H), 2.24 (s, 6H) |

Preparation of Intermediate 32: 4-(cyclopropoxy)pyrimidine-5-carbaldehyde

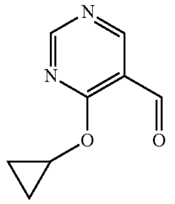 [SMILES: O=Cc1cncnc1OC1CC1]

Step 1: ethyl 4-(cyclopropoxy)pyrimidine-5-carboxylate (Intermediate 33)

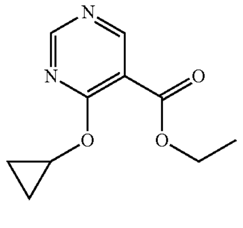

A solution of cyclopropanol (0.9 M in THF, 2.7 mL, 2.41 mmol, 1.50 eq) was added to a solution of NaH (60% dispersion in mineral oil, 129 mg, 3.22 mmol, 2.00 eq) in THE (2.0 mL) and the reaction mixture was stirred over ice/water for 10 min, prior to addition of a solution of ethyl 4-chloropyrimidine-5-carboxylate (300 mg, 1.61 mmol, 1.00 eq) in THE (0.7 mL). The reaction mixture was stirred for 10 min, allowed to warm to room temperature, and stirred for 1.5 h. The reaction mixture was cooled over ice/water and saturated $NH_4Cl_{(aq)}$ was added. The aqueous phase was extracted with 3×EtOAc and the combined organic phases were passed through a hydrophobic frit and concentrated under vacuum to give the title compound (326 mg, 97%).

$^1$H NMR (400 MHz, $CDCl_3$) δ 8.97 (s, 1H), 8.91 (s, 1H), 4.52-4.47 (m, 1H), 4.36 (q, J=7.1 Hz, 2H), 1.37 (t, J=7.1 Hz, 3H), 0.88 (d, J=4.6 Hz, 4H)

Step 2: [4-(cyclopropoxy)pyrimidin-5-yl]methanol (Intermediate 34)

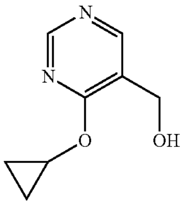 [SMILES: OCc1cncnc1OC1CC1]

A solution of Intermediate 33 (251 mg, 1.21 mmol, 1.00 eq) in anhydrous THE (10.9 mL) was sparged with argon for 10 min and cooled over a dry-ice/acetone bath prior to dropwise addition of 2 M $LiAlH_4$ (2M in THF, 0.54 mL, 1.08 mmol, 0.900 eq). The reaction mixture was stirred for 10 min, until TLC indicated consumption of SM and diluted with anhydrous $Et_2O$ (10 mL). The flask was transferred to an ice/water bath, water (41 μL), 15% NaOH (aq) (41 μL) and water (123 μL) were added and the reaction mixture was stirred while warming to room temperature for 15 min. $MgSO_4$ was added and the reaction mixture was stirred for 15 min and filtered. The filtrate was concentrated under vacuum The solid obtained was purified by FCC on 15 μm silica gel (25 g cartridge, 0-7% 2M $NH_3$/MeOH in DCM) to afford the title compound (107 mg, 53%)

LC-MS (ESI): m/z (M+1)=167; $t_R$=0.72 min Method 12

Step 3: 4-(cyclopropoxy)pyrimidine-5-carbaldehyde (Intermediate 32)

To a solution of Intermediate 34 (130 mg, 0.782 mmol, 1.00 eq) in anhydrous DCM (4 mL), stirred over an ice/water bath, was added Dess-Martin periodinane (431 mg, 1.02 mmol, 1.30 eq). The reaction mixture was allowed to warm to room temperature, stirred for 2 h and diluted with DCM. The organic phase was washed with 10% wt. $Na_2S_2O_{5\,(aq)}$, followed by saturated $NaHCO_{3(aq)}$. The $NaHCO_{3(aq)}$ solution was extracted with DCM and the combined organic phases were passed through a hydrophobic frit and concentrated partially under vacuum to give the title compound (194 mg, >100%).

$^1$H NMR (400 MHz, CDCl) δ 10.27 (s, 1H), 8.98 (s, 1H), 8.93 (s, 1H), 4.59-4.54 (m, 1H), 0.94-0.85 (m, 4H).

Preparation of Intermediate 35: 2-((dimethylamino)methyl)-6-(trifluoromethyl)pyridin-4-amine

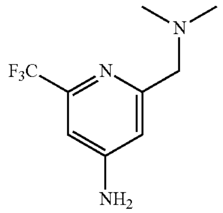

Step 1: 4-amino-N-methoxy-N-methyl-6-(trifluoromethyl)picolinamide (Intermediate 36)

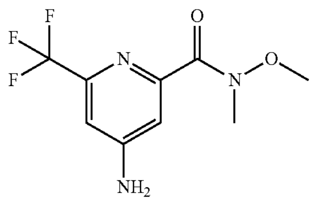 [SMILES: CON(C)C(=O)c1cc(N)cc(C(F)(F)F)n1]

Prepared from 4-amino-6-(trifluoromethyl)picolinic acid (445 mg, 2.16 mmol) and N,O-dimethylhydroxylamine hydrochloride (232 mg, 2.37 mmol) according to general procedure A. Purification was performed by silica FCC (80 g cartridge, 0-50% EtOAc in cyclohexane (+0.1% $NEt_3$)) to afford the title compound (369 mg, 68%).

$^1$H NMR (400 MHz, DMSO-d6) δ 6.96 (d, J=2.1 Hz, 1H), 6.84-6.78 (m, 3H), 3.67 (s, 3H), 3.24 (s, 3H)

Step 2: 4-amino-6-(trifluoromethyl)picolinaldehyde (Intermediate 37)

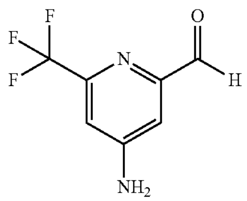

To a stirred solution of Intermediate 36 (308 mg, 1.24 mmol) in THE (4.82 mL) cooled in an ice/water bath was added $LiAlH_4$ (2M in THF, 0.62 mL, 1.24 mmol) dropwise maintaining the internal temperature below 6° C. The reaction mixture was stirred for 1 h and diluted with anhydrous $Et_2O$ (5 mL). Water (47 μL), 15% $NaOH_{(aq)}$ (47 μL) and water (141 μL) were added, the reaction mixture was allowed to warm to room temperature and stirred for 15 min. Anhydrous $MgSO_4$ was added, the reaction mixture was stirred for 15 min, filtered and the filtrate was concentrated under vacuum to give the title compound (252 mg, >100%), which was used in the next step without purification LC-MS (ESI): m/z (M+1)=191; $t_R$=0.95 min Method 12

Step 3: 2-((dimethylamino)methyl)-6-(trifluoromethyl)pyridin-4-amine (Intermediate 35)

Prepared from Intermediate 37 (126 mg, 0.663 mmol) and dimethylamine (2M solution in THF) (0.33 mL, 0.663 mmol) according to general procedure D. Purification was performed by silica FCC (12 g cartridge, 0-8% 2M $NH_3$/MeOH in DCM) to afford the title compound (65 mg, 44%).

$^1$H NMR (400 MHz, DMSO-d6) δ 6.78-6.77 (m, 2H), 6.49 (s, 2H), 3.34 (s, 2H), 2.18 (s, 6H).

Preparation of Intermediate 38: 5-(trifluoromethoxy)pyridin-3-amine (hydrochloride Salt)

Step 1: tert-butyl N-[5-(trifluoromethoxy)-3-pyridyl]carbamate (Intermediate 39)

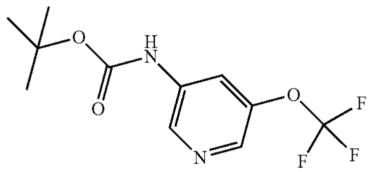 [SMILES: CC(C)(C)OC(=O)Nc1cncc(OC(F)(F)F)c1]

A mixture of tert-Butyl carbamate (102 mg, 0.868 mmol, 1.20 eq), Xantphos (63 mg, 0.108 mmol, 0.150 eq), Tris (dibenzylideneacetone)dipalladium(0)-chloroform adduct (37 mg, 0.0362 mmol, 0.0500 eq) and $Cs_2CO_3$ (283 mg, 0.868 mmol, 1.20 eq) in 1,4-dioxane (5 mL) was degassed with nitrogen and treated with 3-bromo-5-(trifluoromethoxy)pyridine (175 mg, 0.723 mmol, 1.00 eq). The reaction was stirred at 100° C. for 1 hour. The reaction mixture was allowed to cool to room temperature, filtered through a pad of Celite, which was then washed with dioxane, and the combined organic phases concentrated under vacuum. The residue was purified by silica FCC (0-100%, EtOAc in cyclohexane), then dried under vacuum overnight to afford the title compound (115 mg, 0.413 mmol, 57%).

$^1$H NMR (400 MHz, $CDCl_3$) δ 8.33 (d, J=2.3 Hz, 1H), 8.23-8.21 (m, 1H), 8.07 (s, 1H), 7.04 (s, 1H), 1.54 (s, 9H).

Step 2: 5-(trifluoromethoxy)pyridin-3-amine (hydrochloride Salt) (Intermediate 38)

To a solution of Intermediate 39 (115 mg, 0.413 mmol, 1.00 eq) in 1,4-dioxane (3 mL) was added HCl 4N in 1,4-dioxane (3.0 mL, 0.413 mmol, 1.00 eq). The reaction mixture was stirred at room temperature overnight. The reaction mixture was diluted with $Et_2O$ (20 mL) and filtered. The solid was washed with $Et_2O$ and dried under vacuum to afford the title compound (60 mg, 0.280 mmol, 68%).

LC-MS (ESI): m/z (M+1)=179; $t_R$=0.88 min Method 13

Preparation of Intermediate 40: N-(5-formylpyrimidin-2-yl)acetamide

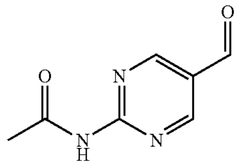

Step 1: N-(5-formylpyrimidin-2-yl)acetamide (Intermediate 40)

2-Aminopyrimidine-5-carboxaldehyde (100 mg, 0.812 mmol, 1.00 eq) was dissolved in Acetic anhydride (2.0 mL, 22.8 mmol, 28.1 eq) and the reaction mixture was heated at 140° C. for 90 min. The reaction mixture was allowed to cool to room temperature and the solid precipitated out, reaction washed with 2:1 cyclohexane/$Et_2O$ and filtered, solid washed with cyclohexane and dried in vacuo. To afford the title compound (84 mg, 0.509 mmol, 62.6% yield).

$^1$H NMR (400 MHz, $CDCl_3$) δ 10.03 (s, 1H), 9.04 (s, 2H), 8.76 (s, 1H), 2.58 (s, 3H).

Example 1: preparation of N-(3-((4-methylpiperazin-1-yl)methyl)-5-(trifluoromethyl)phenyl)-6-(pyridin-3-ylmethyl)-4,5,6,7-tetrahydrothieno[2,3-c]pyridine-3-carboxamide Example 1

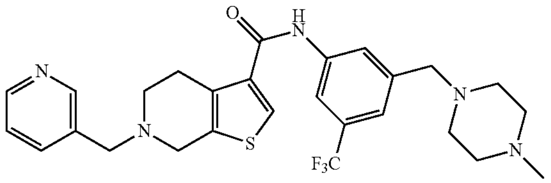

Step 1; tert-butyl 3-((3-((4-methylpiperazin-1-yl)methyl)-5-(trifluoromethyl)phenyl)carbamoyl)-4,7-dihydrothieno[2,3-c]pyridine-6(5H)-carboxylate (Intermediate 2)

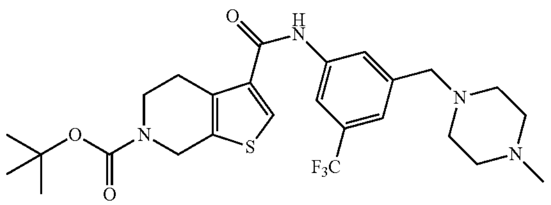 [SMILES: CN1CCN(Cc2cc(NC(=O)c3csc4c3CCN(C(=O)OC(C)(C)C)C4)cc(C(F)(F)F)c2)CC1]

3-((4-methylpiperazin-1-yl)methyl)-5-(trifluoromethyl) aniline (1050 mg, 3.84 mmol) was dissolved in dry THE (Volume: 50 ml, Ratio: 2.500) under Nitrogen and the mixture was stirred at −78° C. for 15 min, then n-BuLi 2.5M in hexanes (1.342 ml, 3.36 mmol) was added dropwise in 5 min and the reaction was stirred for 1 hr at −78° C. A solution of 6-(tert-butyl) 3-ethyl 4,7-dihydrothieno[2,3-c] pyridine-3,6(5H)-dicarboxylate (950 mg, 3.05 mmol) in THE (Volume: 20 ml, Ratio: 1.000) was added dropwise for 10 min, the temperature was increased at RT and the reaction was stirred for 1 hr. 10 mL of water was added to quench the reaction and the solvent was evaporated by reduce pressure. The solid was dissolved in DCM (50 mL) and the organic layer was washed with $H_2O$ (2×20 mL) and Brine (1×20 mL). The organic layer was dried with $Na_2SO_4$, filtrated and concentrated until dryness. The crude was purified by reverse phase FCC to afford the title compound (1.41 g, 2.62 mmol, 86% yield).

$^1$H NMR (400 MHz, Acetone-d6) d ppm 9.58 (s, 1H) 8.19 (s, 1H) 8.09 (s, 1H) 7.94 (s, 1H) 7.38 (s, 1H) 4.65 (s, 2H) 3.67 (t, J=5.81 Hz, 2H) 3.57 (s, 2H) 2.91-3.05 (m, 2H) 2.32-2.56 (m, 8H) 2.21 (s, 3H) 1.47 (s, 9H).

Step 2; N-(3-((4-methylpiperazin-1-yl)methyl)-5-(trifluoromethyl)phenyl)-4,5,6,7-tetrahydrothieno[2,3-c]pyridine-3-carboxamide trihydrochloride (Intermediate 3)

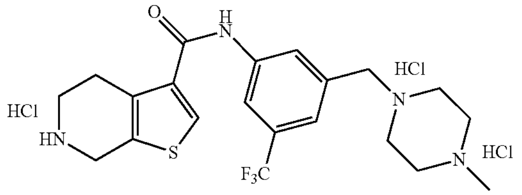 [SMILES: Cl ; CN1CCN(Cc2cc(NC(=O)c3csc4c3CCNC4)cc(C(F)(F)F)c2)CC1 ; Cl ; Cl]

Intermediate 2 (1.41 g, 2.62 mmol) was dissolved in concentrated HCl (3.0 ml, 99 mmol) and the solution was stirred at RT for 10 min. 50 mL of ethanol was added at the reaction and the solvent was evaporated by reduced pressure until obtaining the title compound (1.31 g, 2.391 mmol, 91% yield).

Step 3; 6-(4-cyanobenzyl)-N-(3-((4-methylpiperazin-1-yl)methyl)-5-(trifluoromethyl)phenyl)-4,5,6,7-tetrahydrothieno[2,3-c]pyridine-3-carboxamide Example 1

Intermediate 3 (30 mg, 0.055 mmol), 3-(bromomethyl) pyridine hydrobromide (13.85 mg, 0.055 mmol) were dissolved in DMF (Volume: 3 ml), then DIPEA (0.057 ml, 0.329 mmol) was added in one portion. The solution was stirred on at RT. The crude was purified in prepHPLC (column XSelect® CSH™ Prep C18 5 μm OBD™ 19×100 mm; 5-95% ACN/$H_2O$ (0.1% HCOOH), 20 ml/min, RT). The relevant fractions were combined and loaded onto an Isolute® SCX-2 cartridge, washed with MeOH and the product was eluted with 7N methanolic ammonia. The residue was concentrated under vacuum to afford the title compound (17.6 mg, 0.033 mmol, 60.7% yield).

$^1$H NMR (400 MHz, ACN-d3) 6 ppm 8.70 (br s, 1H), 8.56 (s, 1H), 8.49 (d, J=4.60 Hz, 1H), 7.99 (s, 1H), 7.84 (d, J=7.23 Hz, 2H), 7.76 (br d, J=7.67 Hz, 1H), 7.30-7.36 (m, 2H), 3.73

(s, 2H), 3.67 (s, 2H), 3.54 (s, 2H), 2.94 (br t, J=5.59 Hz, 2H), 2.78 (t, J=5.70 Hz, 2H), 2.27-2.53 (br s, 8H), 2.20 (s, 3H).

LC-MS (ESI): m/z (M+1)=530.4; $t_R$=0.53 Method 1

The following compound was prepared via nucleophilic substitution as described for Example 1, steps 1-3, applying the corresponding commercially available benzyl bromide in step 3.

| Ex. No | Structure | SM Amount | Product Amount (yield) | Method purification | Data |
|---|---|---|---|---|---|
| 2 | 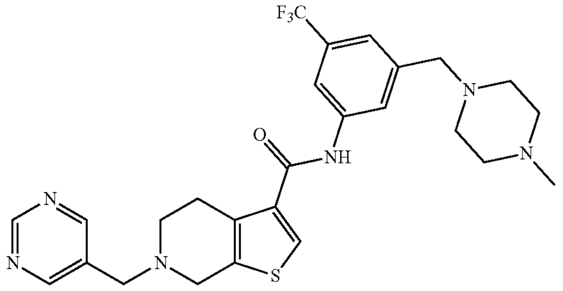 [SMILES: CN1CCN(Cc2cc(NC(=O)c3csc4c3CCN(Cc3cncnc3)C4)cc(C(F)(F)F)c2)CC1] | Intermediate 3: 50 mg | 27.4 mg (57%) | prepHPLC + SCX | $^1$H NMR (400 MHz, ACN-d3) δ ppm 9.07 (s, 1H), 8.71-8.74 (m, 3H), 7.99 (s, 1H), 7.86 (s, 1H), 7.83 (s, 1H), 7.35 (s, 1H), 3.71 and 3.72 (2s, 2H each, 4H), 3.54 (s, 2H), 2.95 (br t, J = 5.70 Hz, 2H), 2.80 (t, J = 5.81 Hz, 2H), 2.27-2.55 (m, 8H), 2.20 (s, 3H) LC-MS (ESI): Method 1 $t_R$ = 0.60 min; m/z (M + 1) = 531.4 |

Example 3: preparation of N-(3-(4-methyl-1H-imidazol-1-yl)-5-(trifluoromethyl)phenyl)-6-(pyrimidin-5-ylmethyl)-4,5,6,7-tetrahydrothieno[2,3-c]pyridine-3-carboxamide

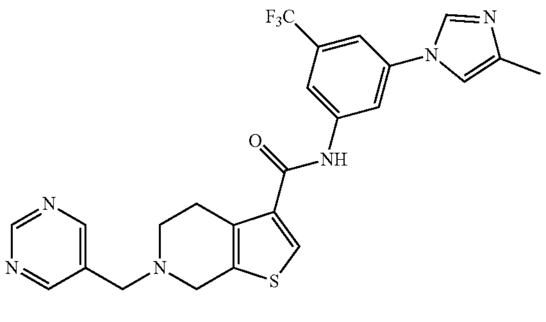 [SMILES: Cc1cn(-c2cc(NC(=O)c3csc4c3CCN(Cc3cncnc3)C4)cc(C(F)(F)F)c2)cn1]

Example 3

Step 1; tert-butyl 3-((3-(4-methyl-1H-imidazol-1-yl)-5-(trifluoromethyl)phenyl)carbamoyl)-4,7-dihydrothieno[2,3-c]pyridine-6(5H)-carboxylate (Intermediate 4)

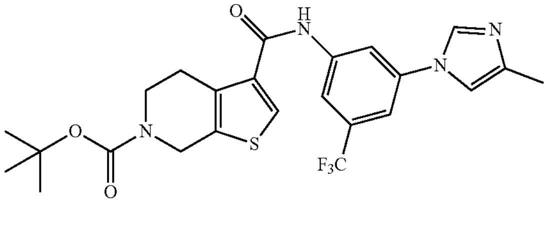 [SMILES: Cc1cn(-c2cc(NC(=O)c3csc4c3CCN(C(=O)OC(C)(C)C)C4)cc(C(F)(F)F)c2)cn1]

To a solution 6-(tert-butoxycarbonyl)-4,5,6,7-tetrahydrothieno[2,3-c]pyridine-3-carboxylic acid (1.5 g, 5.29 mmol) and 3-(4-methyl-1H-imidazol-1-yl)-5-(trifluoromethyl)aniline (1.277 g, 5.29 mmol) in DCM (26.5 ml), DIPEA (5.55 ml, 31.8 mmol) was added followed by T3P (6.30 ml, 10.59 mmol) and reaction mixture was stirred at RT overweekend. The reaction mixture was diluted with DCM, water was added and this mixture was stirred for 10 min The aqueous phase was washed with DCM (3×50 mL), then the combined organic phases were washed with brine, dried over $Na_2SO_4$, filtrated and concentrated under reduced pressure. The crude was purified via FCC (DCM to 10% MeOH in DCM) to afford the title compound (362 mg, 0.715 mmol, 13.50% yield).

$^1$H NMR (300 MHz, DMSO-d6) δ 10.52 (s, 1H), 8.19 (q, J=1.9, 1.4 Hz, 3H), 8.07 (d, J=1.9 Hz, 1H), 7.74-7.67 (m, 1H), 7.46 (t, J=1.3 Hz, 1H), 4.60 (s, 2H), 3.58 (t, J=5.8 Hz, 2H), 2.87 (t, J=5.8 Hz, 2H), 2.18 (d, J=1.0 Hz, 3H), 1.43 (s, 9H).

Step 2; N-(3-(4-methyl-1H-imidazol-1-yl)-5-(trifluoromethyl)phenyl)-4,5,6,7-tetrahydrothieno[2,3-c]pyridine-3-carboxamide hydrochloride (Intermediate 5)

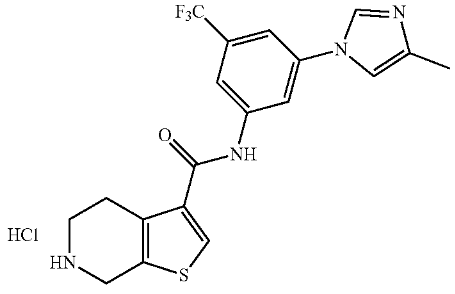 [SMILES: Cl ; Cc1cn(-c2cc(NC(=O)c3csc4c3CCNC4)cc(C(F)(F)F)c2)cn1]

Intermediate 4 (0.362 g, 0.715 mmol) in DCM (3.57 ml), 4N HCl in Dioxane (0.893 ml, 3.57 mmol) was added and the reaction mixture was stirred at RT overnight. $Et_2O$ was added to the reaction mixture till no more precipitation was observed, then the precipitate was filtered off, to afford the title compound (0.33 g, 0.745 mmol, 104% yield).

$^1$H NMR (300 MHz, DMSO-d6) δ 11.05 (s, 1H), 9.61 (s, 1H), 9.55 (s, 1H), 8.60 (s, 1H), 8.57 (s, 1H), 8.29 (s, 1H), 7.98 (s, 1H), 7.91 (s, 1H), 4.39 (s, 2H), 3.37 (m, 2H), 3.13 (m, 2H), 2.36 (d, J=1.1 Hz, 3H).

Step 3; N-(3-(4-methyl-1H-imidazol-1-yl)-5-(trifluoromethyl)phenyl)-6-(pyrimidin-5-ylmethyl)-4,5,6,7-tetrahydrothieno[2,3-c]pyridine-3-carboxamide Example 3

Intermediate 5 (100 mg, 0.246 mmol) and pyrimidine-5-carbaldehyde (27.9 mg, 0.258 mmol) were suspended in AcOH (1230 μl) under Argon atmosphere and treated with STAB (104 mg, 0.492 mmol). The reaction was stirred for 16 hr. The reaction mixture was diluted with MeOH and concentrated under vacuum. The dried reaction mixture was re-dissolved in DCM and washed with 1M NaOH followed by water and brine. The combined organic layers were concentrated and purified via prepHPLC to afford the title compound (22 mg, 0.044 mmol, 17.94% yield).

$^1$H NMR (400 MHz, DMSO-d6) δ 10.50 (s, 1H), 9.13 (s, 1H), 8.80 (s, 2H), 8.20 (dd, J=4.6, 2.6 Hz, 3H), 8.08 (d, J=1.9 Hz, 1H), 7.70 (s, 1H), 7.47 (s, 1H), 3.77 (s, 2H), 3.69 (s, 2H), 2.90 (d, J=6.0 Hz, 2H), 2.76 (t, J=5.8 Hz, 2H), 2.18 (d, J=1.0 Hz, 3H).

LC-MS (ESI): m/z (M+1)=499.0; $t_R$=2.75 Method 3

Example 4: Preparation of N-(3-fluoro-5-(trifluoromethyl)phenyl)-6-(pyrimidin-5-ylmethyl)-4,5,6,7-tetrahydrothieno[2,3-c]pyridine-3-carboxamide

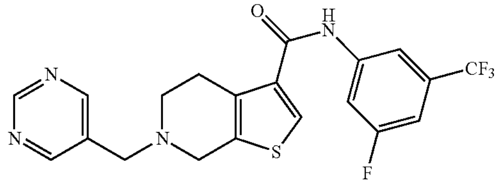 [SMILES: O=C(Nc1cc(F)cc(C(F)(F)F)c1)c1csc2c1CCN(Cc1cncnc1)C2]

Example 4

Step 1; ethyl 4,5,6,7-tetrahydrothieno[2,3-c]pyridine-3-carboxylate hydrochloride (Intermediate 6)

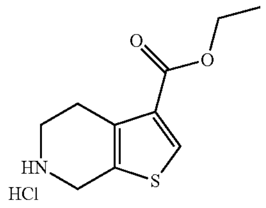

To a solution of 6-(tert-butyl) 3-ethyl 4,7-dihydrothieno[2,3-c]pyridine-3,6(5H)-dicarboxylate (4.88 g, 15.67 mmol) in Diethyl ether (Volume: 78 ml), 4N HCl in Dioxane (19.59 ml, 78 mmol) was added and the reaction mixture was stirred at RT overnight. The solid was separated and dried under reduced pressure to afford the title compound (3.58 g, 14.45 mmol, 92% yield).

Step 2; ethyl 6-(pyrimidin-5-ylmethyl)-4,5,6,7-tetrahydrothieno[2,3-c]pyridine-3-carboxylate (Intermediate 7)

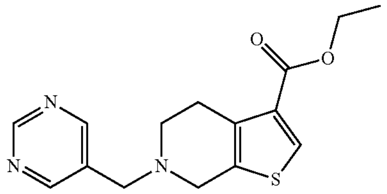 [SMILES: CCOC(=O)c1csc2c1CCN(Cc1cncnc1)C2]

Intermediate 6 (3.0 g, 12.11 mmol) and pyrimidine-5-carbaldehyde (1.309 g, 12.11 mmol) were placed in flask under argon. Anhydrous DCM (121 ml) was added followed by AcOH (0.693 ml, 12.11 mmol). Reaction mixture was stirred 30 min at RT. Next STAB (5.13 g, 24.22 mmol) was added and reaction mixture stirred at RT over weekend.

Then reaction mixture was diluted with DCM and washed with a mixture of $K_2CO_3$ (sat) and water 1:1. Aqueous phase was extracted with DCM twice, organic layers were combined, dried over $MgSO_4$ and evaporated under reduced pressure. The crude was purified via FCC with DCM/MeOH (DCM to 10% MeOH in DCM) to afford the title compound (1.97 g, 6.49 mmol, 54% yield).

$^1$H NMR (300 MHz, $CDCl_3$) δ 9.16 (s, 1H), 8.76 (s, 2H), 7.95 (s, 1H), 4.29 (q, J=7.1 Hz, 2H), 3.74 (s, 2H), 3.70 (s, 2H), 3.07-2.97 (m, 2H), 2.84 (t, J=5.9 Hz, 2H), 1.34 (t, J=7.1 Hz, 3H).

Step 3; sodium 6-(pyrimidin-5-ylmethyl)-4,5,6,7-tetrahydrothieno[2,3-c]pyridine-3-carboxylate (Intermediate 8)

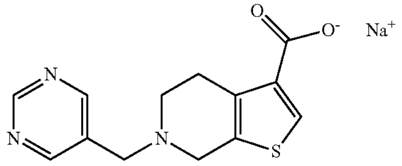 [SMILES: O=C([O-])c1csc2c1CCN(Cc1cncnc1)C2 ; [Na+]]

To a solution of Intermediate 7 (1.97 g, 6.49 mmol) in MeOH (64.9 ml), NaOH 1N (6.49 ml, 6.49 mmol) was added, reaction mixture was stirred at RT overweekend. The solvent was evaporated under vacuum to obtained the title compound.

$^1$H NMR (300 MHz, DMSO-d6) δ 9.10 (s, 1H), 8.77 (s, 2H), 7.45 (s, 1H), 3.70 (s, 2H), 3.58 (s, 2H), 2.90 (t, J=5.8 Hz, 2H), 2.66 (t, J=5.8 Hz, 2H).

Step 4; N-(3-fluoro-5-(trifluoromethyl)phenyl)-6-(pyrimidin-5-ylmethyl)-4,5,6,7-tetrahydrothieno[2,3-c]pyridine-3-carboxamide (Example 4)

Intermediate 8 (0.1 g, 0.336 mmol) was dissolved in DMF (0.841 ml) and DCM (2.52 ml) then DIPEA (0.352 ml, 2.018 mmol) and HATU (0.256 g, 0.673 mmol) were added. RM was stirred for 15 minutes and then 3-fluoro-5-(trifluoromethyl)aniline (0.044 ml, 0.336 mmol) was added. The reaction was stirred at 60° C. over the weekend. Then DCM and brine were added to the reaction mixture and it was stirred for 20 min. Next, the phases were separated and organic layer was washed with water, separated and contrated under vacuum. The crude product was purified via flash column chromatography (DCM:MeO from, 1:0 to 0:1). It was repurified via preparative TLC (DCM:MeOH, 95:5) to afford the title compound (20 mg, 0.046 mmol, 14% yield).

$^1$H NMR (300 MHz, DMSO-d6) δ 10.52 (s, 1H), 9.12 (s, 1H), 8.79 (s, 2H), 8.13 (s, 1H), 7.99-7.90 (m, 2H), 7.36 (d, J=8.3 Hz, 1H), 3.75 (s, 2H), 3.67 (s, 2H), 2.88 (t, J=5.6 Hz, 2H), 2.75 (t, J=5.7 Hz, 2H).

LC-MS (ESI): m/z (M+1)=437.0; $t_R$=1.92 min Method 2

The following compounds were prepared as described for Example 4, steps 1-4, applying the corresponding, commercially available aryl amine in step 4. Such procedures may involve minor variations. In some cases, where modification involved coupling agents (e.g. HATU instead of T3P) or chromatographic purification conditions (eg. prepHPLC or flash chromatography), such changes were reported in the table. In Example 8 the starting material of step 3 was converted into the corresponding carboxylic acid by deblocking the sodium salt obtained as described in example 9, step 1.

Example 9: preparation of N-(3-(1,1-difluoroethyl)phenyl)-6-(pyrimidin-5-ylmethyl)-4,5,6,7-tetrahydrothieno[2,3-c]pyridine-3-carboxamide

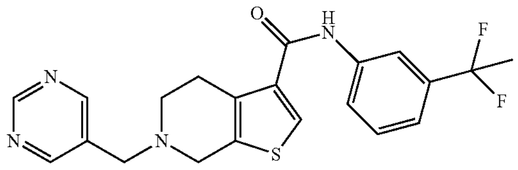

| Example No | Structure | Intermediate 8 Amount | Product Amount (yield) | Purification | Data |
|---|---|---|---|---|---|
| 5 | 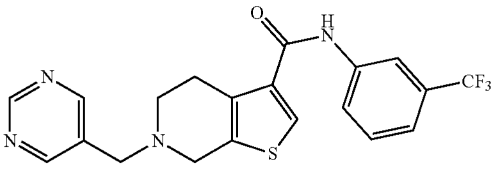 [SMILES: O=C(Nc1cccc(C(F)(F)F)c1)c1csc2c1CCN(Cc1cncnc1)C2] | 100 mg (1 eq.) | 31 mg (22%) | prepHPLC + washing with $NaHCO_3$ sol | $^1$H NMR (300 MHz, DMSO-d6) δ 10.35 (s, 1H), 9.12 (s, 1H), 8.79 (s, 2H), 8.19 (s, 1H), 8.11 (s, 1H), 7.97 (d, J = 8.3 Hz, 1H), 7.58 (t, J = 7.9 Hz, 1H), 7.47-7.37 (m, 1H), 3.76 (s, 2H), 3.68 (s, 2H), 2.88 (d, J = 5.8 Hz, 2H), 2.75 (t, J = 5.7 Hz, 2H). LC-MS (ESI): method 6 $t_R$ = 1.72 min; m/z (M + 1) = 419.1 |
| 6 | 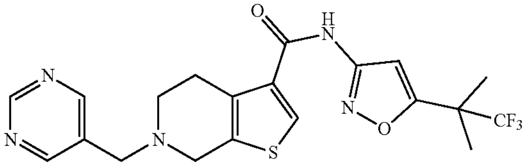 [SMILES: CC(C)(c1cc(NC(=O)c2csc3c2CCN(Cc2cncnc2)C3)no1)C(F)(F)F] | 80 mg (1 eq.) $T_3P$ (2 eq.) replaces HATU | 55 mg (45%) | FCC | $^1$H NMR (300 MHz, DMSO-d6) δ 11.27 (s, 1H), 9.12 (s, 1H), 8.78 (s, 2H), 8.28 (s, 1H), 7.06 (s, 1H), 3.74 (s, 2H), 3.66 (s, 2H), 2.87 (d, J = 5.8 Hz, 2H), 2.74 (d, J = 5.6 Hz, 2H), 1.57 (s, 6H). LC-MS (ESI): method 2 $t_R$ = 2.01 min; m/z (M + 1) = 452.1 |
| 7 | 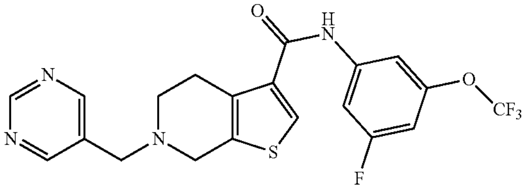 [SMILES: O=C(Nc1cc(F)cc(OC(F)(F)F)c1)c1csc2c1CCN(Cc1cncnc1)C2] | 100 mg (1 eq.) | 10.7 mg (7%) | prepHPLC | $^1$H NMR (300 MHz, DMSO-d6) δ 10.48 (s, 1H), 9.12 (s, 1H), 8.79 (s, 2H), 8.10 (s, 1H), 7.73-7.62 (m, 2H), 7.06 (d, J = 9.1 Hz, 1H), 3.75 (s, 2H), 3.67 (s, 2H), 2.86 (d, J = 5.5 Hz, 2H), 2.74 (t, J = 5.5 Hz, 2H). LC-MS (ESI): method 5 $t_R$ = 2.13 min; m/z (M + 1) = 453.01 |
| 8 | 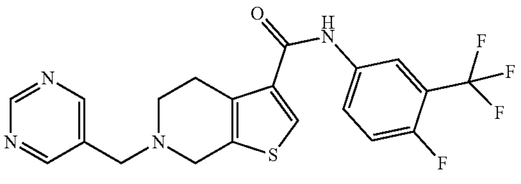 [SMILES: O=C(Nc1ccc(F)c(C(F)(F)F)c1)c1csc2c1CCN(Cc1cncnc1)C2] | 50 mg (1 eq.) General procedure A | 19 mg (23%) | prepHPLC | $^1$H NMR (400 MHz, DMSO) δ 10.38 (s, 1H), 9.14 (s, 1H), 8.80 (s, 2H), 8.22 (dd, J = 2.6, 6.5 Hz, 1H), 8.11 (s, 1H), 8.05-8.00 (m, 1H), 7.50 (t, J = 9.7 Hz, 1H), 3.77 (s, 2H), 3.69 (s, 2H), 2.89 (t, J = 5.5 Hz, 2H), 2.76 (t, J = 5.5 Hz, 2H) LC-MS (ESI): method 8 $t_R$ = 4.53 min; m/z (M + 1) = 437 |

Example 9

Step 1: 6-(pyrimidin-5-ylmethyl)-4,5,6,7-tetrahydrothieno[2,3-c]pyridine-3-carboxylic acid (Intermediate 9)

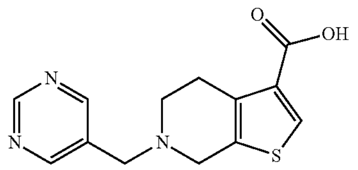 [SMILES: O=C(O)c1csc2c1CCN(Cc1cncnc1)C2]

To a solution of Intermediate 7 (880 mg, 2.90 mmol, 1.00 eq) in MeOH (20 mL) was added 5M $NaOH_{(aq)}$ (1.50 mL). The reaction mixture was stirred at 60° C. for 2 h. The reaction mixture was allowed to cool to room temperature, neutralized by addition of 1M $HCl_{(aq)}$ and concentrated under vacuum. The residue was washed with water and filtered to yield the title compound (478 mg, 57%)

$^1$H NMR (400 MHz, DMSO) δ 9.16 (s, 1H), 8.83 (s, 2H), 8.12 (s, 1H), 3.79 (s, 2H), 3.70 (s, 2H), 2.91 (t, J=5.7 Hz, 2H), 2.78 (t, J=5.7 Hz, 2H)

Step 2; N-(3-(1,1-difluoroethyl)phenyl)-6-(pyrimidin-5-ylmethyl)-4,5,6,7-tetrahydrothieno[2,3-c]pyridine-3-carboxamide (Example 9)

Prepared from 3-(1,1-difluoroethyl)aniline (31 mg, 0.197 mmol) and Intermediate 9 (54 mg 0.197 mmol) according to general procedure B. By purification by reverse phase pre-pHPLC (Sunfire C18 3x50 mm, 3 um 5-95% ACN/$H_2O$ (0.1% HCOOH), 1.7 ml/min, RT) the title compound was obtained (17.5 mg, 22.2%).

$^1$H NMR (400 MHz, DMSO) δ 10.21 (s, 1H), 9.14 (s, 1H), 8.80 (s, 2H), 8.10 (s, 1H), 7.98 (s, 1H), 7.83 (d, J=8.4 Hz, 1H), 7.46 (t, J=7.9, 7.9 Hz, 1H), 7.26 (d, J=7.8 Hz, 1H), 3.77 (s, 2H), 3.69 (s, 2H), 2.89 (t J=5.5 Hz, 2H), 2.76 (t, J=5.8 Hz, 2H), 1.97 (t, J=18.8 Hz, 3H).

LC-MS (ESI): m/z (M+1)=415; $t_R$=4.28 min Method 9

The following compounds were prepared via amido coupling as described for Example 9, steps 1-2, applying the corresponding commercially available aryl amine in step 2.

| Example No | Structure | Intermediate Amount | Product Amount (yield) | Method Purification | Data |
|---|---|---|---|---|---|
| 10 | 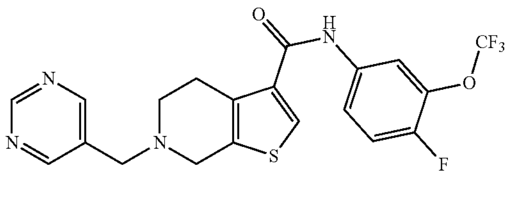 [SMILES: O=C(Nc1ccc(F)c(OC(F)(F)F)c1)c1csc2c1CCN(Cc1cncnc1)C2] | Aniline: (38.5 mg, 0.197 mmol) Intermediate 9: (54 mg 0.197 mmol) | 15.7 mg (19%) | PrepHPLC | $^1$H NMR (400 MHz, DMSO) δ 10.34 (s, 1H), 9.13 (s, 1H), 8.80 (s, 2H), 8.09 (s, 1H), 8.04 (m, 1H), 7.72 (ddd, J = 2.6, 4.2, 9.2 Hz, 1H), 7.49 (dd, J = 9.2 Hz, 1H), 3.77 (s, 2H), 3.69 (s, 2H), 2.88 (t, J = 5.7 Hz, 2H), 2.75 (t, J = 5.7 Hz, 2H) LC-MS (ESI): method 9 $t_R$ = 3.51 min; m/z (M + 1) = 453.3 |
| 11 | 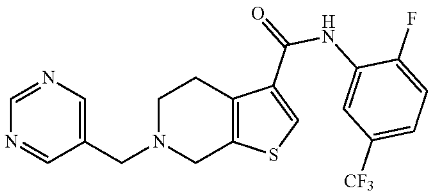 [SMILES: O=C(Nc1cc(C(F)(F)F)ccc1F)c1csc2c1CCN(Cc1cncnc1)C2] | Aniline: (35.3 mg, 0.197 mmol) Intermediate 9: (54 mg 0.197 mmol) | 4.7 mg (6%) | prepHPLC | $^1$H NMR (400 MHz, DMSO) δ 10.10 (s, 1H), 9.13 (s, 1H), 8.80 (s, 2H), 8.18 (s, 1H), 8.11 (dd, J = 2.3, 6.9 Hz, 1H), 7.67-7.63 (m, 1H), 7.56 (t, J = 9.3 Hz, 1H), 3.77 (s, 2H), 3.69 (s, 2H), 2.89 (t, J = 5.7 Hz, 2H), 2.76 (t, 2H). LC-MS (ESI): method 9 $t_R$ = 3.27 min; m/z (M + 1) = 437.2 |
| 12 | 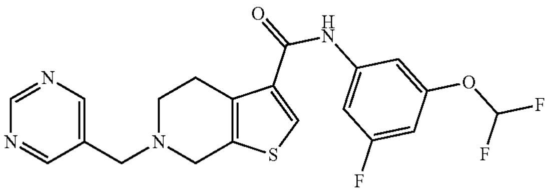 [SMILES: O=C(Nc1cc(F)cc(OC(F)F)c1)c1csc2c1CCN(Cc1cncnc1)C2] | Aniline: (35 mg, 0.197 mmol) Intermediate 9: (54 mg 0.197 mmol) | 4.5 mg (6%) | prepHPLC | $^1$H NMR (400 MHz, DMSO) δ 10.38 (s, 1H), 9.14 (s, 1H), 8.80 (s, 2H), 8.10 (s, 1H), 7.57-7.53 (m, 1H), 7.47-7.09 (t, J = 74 Hz 1H), 6.88-6.83 (m, 1H), 3.77 (s, 2H), 3.69 (s, 2H), 2.87 (t, J = 5.3 Hz, 2H), 2.76 (t, J = 5.3, 5.3 Hz, 2H) LC-MS (ESI): method 8 $t_R$ = 4.42 min; m/z (M + 1) = 435.2 |

-continued

| Example No | Structure | Intermediate Amount | Product Amount (yield) | Method Purification | Data |
|---|---|---|---|---|---|
| 13 | 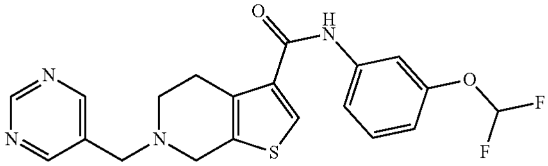 [SMILES: O=C(Nc1cccc(OC(F)F)c1)c1csc2c1CCN(Cc1cncnc1)C2] | Aniline: (31.4 mg, 0.197 mmol) Intermediate 9: (54 mg 0.197 mmol) | 19.5 mg (26%) | prepHPLC | $^1$H NMR (400 MHz, DMSO) δ 10.22 (s, 1H), 9.14 (s, 1H), 8.80 (s, 2H), 8.09 (s, 1H), 7.69 (t, J = 2.1 Hz, 1H), 7.57 (dd, J = 1.3, 8.1 Hz, 1H), 7.39 (d, J = 8.2 Hz, 1H), 7.20 (t, J = 65.8 Hz, 1H), 6.90 (dd, J = 2.3, 8.2 Hz, 1H), 3.77 (s, 2H), 3.69 (s, 2H), 2.88 (t, J = 5.6 Hz, 2H), 2.76 (t, J = 5.8 Hz, 2H). LC-MS (ESI): method 8 $t_R$ = 4.17 min; m/z (M + 1) = 417.2 |
| 14 | 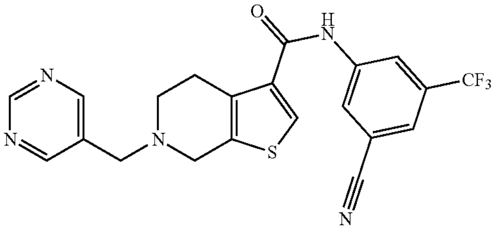 [SMILES: N#Cc1cc(NC(=O)c2csc3c2CCN(Cc2cncnc2)C3)cc(C(F)(F)F)c1] | Aniline: (38.4 mg, 0.206 mmol) Intermediate 9: (57 mg 0.206 mmol) | 15.7 mg (19%) | prepHPLC | $^1$H NMR (400 MHz, DMSO) δ 10.64 (s, 1H), 9.14 (s, 1H), 8.81 (s, 2H), 8.43 (dd, J = 8.9 Hz, 2H), 8.18 (s, 1H), 8.05 (s, 1H), 3.77 (s, 2H), 3.70 (s, 2H), 2.90 (t, J = 5.5 Hz, 2H), 2.77 (t, J = 5.8 Hz, 2H). LC-MS (ESI): method 9 $t_R$ = 3.35 min; m/z (M + 1) = 444 |

Example 15: preparation of 6-((3-aminopyrazin-2-yl)methyl)-N-(3-(tert-butyl)-1-methyl-1H-pyrazol-5-yl)-4,5,6,7-tetrahydrothieno[2,3-c]pyridine-3-carboxamide Example 15

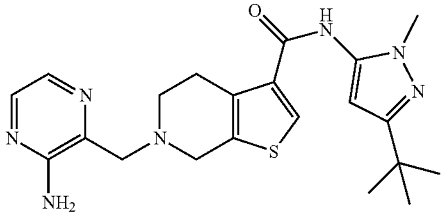

Step 1; sodium 6-(tert-butoxycarbonyl)-4,5,6,7-tetrahydrothieno[2,3-c]pyridine-3-carboxylate (Intermediate 10)

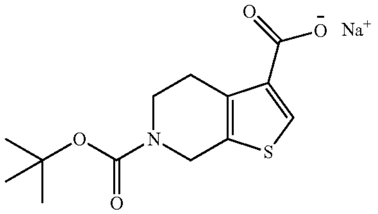 [SMILES: CC(C)(C)OC(=O)N1CCc2c(C(=O)[O-])csc2C1 ; [Na+]]

6-(tert-butyl) 3-ethyl 4,7-dihydrothieno[2,3-c]pyridine-3,6(5H)-dicarboxylate (15 g, 48.2 mmol) was dissolved in MeOH (482 ml) then NaOH 1M (120.5 ml, 120.5 mmol) was added and the RM stirred at RT until to obtain full conversion. RM was dried under reduced pressure to afford the title compound.

$^1$H NMR (300 MHz, DMSO-d6) δ 7.46 (s, 1H), 4.49 (s, 2H), 3.51 (t, J=5.8 Hz, 2H), 2.89 (t, J=5.8 Hz, 2H), 1.41 (s, 9H).

Step 2; tert-butyl 3-((3-(tert-butyl)-1-methyl-1H-pyrazol-5-yl)carbamoyl)-4,7-dihydrothieno[2,3-c]pyridine-6(5H)-carboxylate (Intermediate 11)

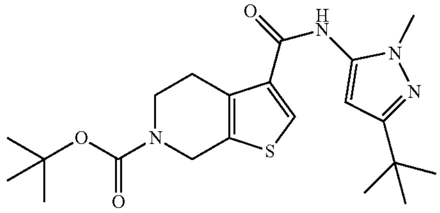 [SMILES: Cn1nc(C(C)(C)C)cc1NC(=O)c1csc2c1CCN(C(=O)OC(C)(C)C)C2]

Intermediate 10 (1 g, 3.28 mmol) and HATU (4.982 g, 13.10 mmol) were weighed into a reaction tube which was backfilled with argon (×3). DCM (24.56 ml) and DMF (8.19 ml) were added to the reaction mixture followed by DIPEA (9.16 ml, 52.4 mmol). The reaction mixture was stirred for 30 mins and 3-(tert-butyl)-1-methyl-1H-pyrazol-5-amine (0.502 g, 3.28 mmol) was added and the reaction was heated to 45 C and stirred until LC-MS indicated consumption of starting material. Further additions of HATU and DIPEA were necessary to obtain complete conversion. The reaction mixture was then extracted with DCM/$H_2O$ (×3) and the combined organic layers washed with 1:1 NaCl(sat):$H_2O$ solution followed by brine. The combined organic layers were then concentrated under vacuum to yield the crude material which was purified via flash column chromatography (0-50% EtOAc/Hexane. Product eluted at 50% EtOAc) to give title compound (1.13 g, 2.70 mmol, 82% yield).

$^1$H NMR (300 MHz, DMSO-d6) δ 10.01 (s, 1H), 8.14 (s, 1H), 6.08 (s, 1H), 4.59 (s, 2H), 3.59 (m, 5H), 2.82 (d, J=5.7 Hz, 2H), 1.43 (s, 9H), 1.23 (s, 9H).

Step 3; N-(3-(tert-butyl)-1-methyl-1H-pyrazol-5-yl)-4,5,6,7-tetrahydrothieno[2,3-c]pyridine-3-carboxamide hydrochloride (Intermediate 12)

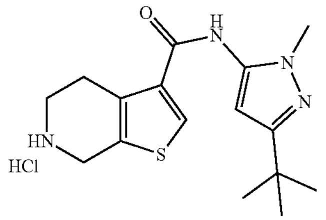 [SMILES: Cl ; Cn1nc(C(C)(C)C)cc1NC(=O)c1csc2c1CCNC2]

Intermediate 11 (1.13 g, 2.70 mmol) was dissolved in DCM (27.0 ml) and cooled to 0° C. HCl in dioxane (3.37 ml, 13.50 mmol) was added dropwise and the reaction left to stir at RT for 16 h. The reaction mixture was concentrated and the residue triturated with diethyl ether to afford the title compound.

$^1$H NMR (300 MHz, DMSO-d6) δ 10.21 (s, 1H), 9.46 (s, 2H), 8.34 (s, 1H), 6.09 (s, 1H), 4.38 (s, 2H), 3.63 (s, 3H), 3.37 (t, J=6.8 Hz, 2H), 3.07 (t, J=6.0 Hz, 2H), 1.23 (s, 9H).

Step 4; 6-((3-aminopyrazin-2-yl)methyl)-N-(3-(tert-butyl)-1-methyl-1H-pyrazol-5-yl)-4,5,6,7-tetrahydrothieno[2,3-c]pyridine-3-carboxamide (Example 15)

Intermediate 12 (100 mg, 0.282 mmol) and 3-aminopyrazine-2-carbaldehyde (41.6 mg, 0.338 mmol) were added to a small reaction tube and backfilled with argon (×3). MeOH (1409 μl) was added to the reaction mixture followed by AcOH (48.4 μl, 0.845 mmol) and the tube was sealed and stirred at 50° C. for 1 h. The reaction was then cooled to RT and $NaBH_3CN$ (80 mg, 1.268 mmol) was added and the reaction stirred at 50° C. Further addictions of aldehyde (2 eq) and $NaBH_3CN$ (1 eq) were necessary to lead a full conversion. The reaction mixture was quenched with sat $NaHCO_3$, transferred to a separatory funnel and the desired product extracted with DCM (×3) and the combined organic layers washed once with brine, concentrated under vacuum and the crude mixture purified via prepHPLC to afford the title compound (28 mg, 0.066 mmol, 23.35% yield).

$^1$H NMR (300 MHz, DMSO-d6) δ 10.00 (s, 1H), 8.10 (s, 1H), 7.89 (d, J=2.8 Hz, 1H), 7.70 (d, J=2.8 Hz, 1H), 6.45 (s, 2H), 6.07 (s, 1H), 3.77 (s, 2H), 3.66 (s, 2H), 3.61 (s, 3H), 2.85 (d, J=5.9 Hz, 2H), 2.74 (d, J=5.4 Hz, 2H), 1.22 (s, 9H).

LC-MS (ESI): m/z (M+1)=425.8; $t_R$=3.07 min Method 4

The following compounds were prepared via reductive amination as described for Example 15, steps 1-4, applying the previously synthesized or commercially available aryl aldehyde in step 4. Such procedures may involve minor variations. In some cases, where any modification involved the used procedure or reductive agents (e.g. STAB instead of $NaBH_3CN$) or chromatographic purification conditions, such changes were reported in the table.

| Example No | Structure | Reagent Amount s | Product Amount (yield) | Purification | Data |
|---|---|---|---|---|---|
| 16 | 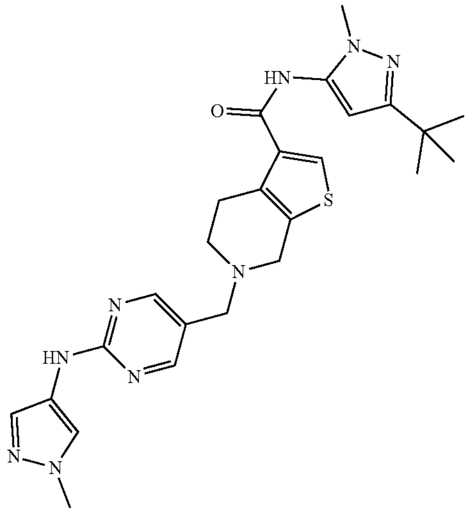 [SMILES: Cn1cc(Nc2ncc(CN3CCc4c(C(=O)Nc5cc(C(C)(C)C)nn5C)csc4C3)cn2)cn1] | Intermediate 12:100 mg (1 eq.) Intermediate 1: 1.1 eq. | 21 mg (15%) | prepHPLC | $^1$H NMR (300 MHz, DMSO-d6) δ 9.96 (s, 1H), 9.42 (s, 1H), 8.36 (s, 2H), 8.08 (s, 1H), 7.88 (d, J = 0.7 Hz, 1H), 7.46 (d, J = 0.7 Hz, 1H), 6.07 (s, 1H), 3.80 (s, 3H), 3.65-3.61 (m, 2H), 3.60 (s, 3H), 3.58-3.54 (m, 2H), 2.88-2.82 (m, 2H), 2.75-2.69 (m, 2H), 1.22 (s, 9H). LC-MS (ESI): method 2 $t_R$ = 1.37 min; m/z (M + 1) = 506.2 |

-continued

| Example No | Structure | Reagent Amount s | Product Amount (yield) | Purification | Data |
|---|---|---|---|---|---|
| 26 | 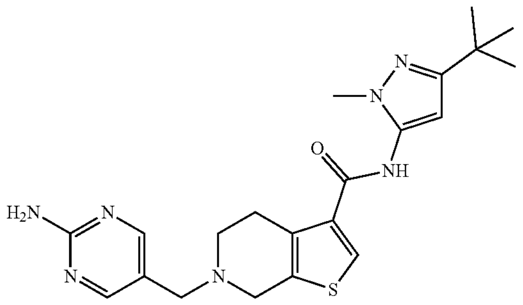 [SMILES: Cn1nc(C(C)(C)C)cc1NC(=O)c1csc2c1CCN(Cc1cnc(N)nc1)C2] | General procedure C Intermediate 12: 50 mg (1 eq.) 2-aminopyrimidine-5-carboxaldehyde: 1.0 eq. | 12 mg (19%) | prepHPLC | $^1$H NMR (400 MHz, DMSO-d6) δ 9.97 (s, 1H), 8.19 (s, 2H), 8.08 (s, 1H), 6.58 (s, 2H), 6.09 (s, 1H), 3.62 (s, 3H), 3.60 (s, 2H), 3.50 (s, 2H), 2.84 (t, J = 5.6 Hz, 2H), 2.70 (t, J = 5.5 Hz, 2H), 1.24 (s, 9H). LC-MS (ESI): Method 9 $t_R$ = 2.62 min; m/z (M + 1) = 426.4 |

Example 17: preparation of 6-((4-(2-methoxyacetamido)pyridin-3-yl)methyl)-N-(3-(trifluoromethyl)phenyl)-4,5,6,7-tetrahydrothieno[2,3-c]pyridine-3-carboxamide Example 17

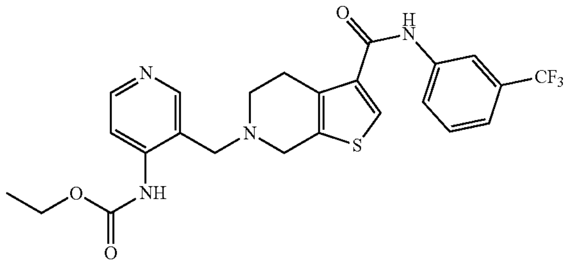

Step 1; tert-butyl 3-((3-(trifluoromethyl)phenyl)carbamoyl)-4,7-dihydrothieno[2,3-c]pyridine-6(5H)-carboxylate (Intermediate 13)

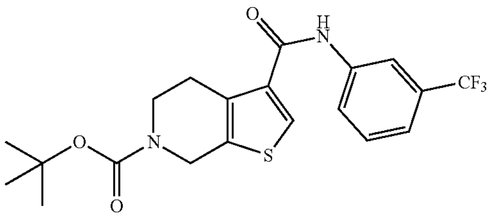 [SMILES: CC(C)(C)OC(=O)N1CCc2c(C(=O)Nc3cccc(C(F)(F)F)c3)csc2C1]

Intermediate 10 (4 g, 13.10 mmol) were dissolved in DMF (32.8 ml) and DCM (98 ml) then DIPEA (4.58 ml, 26.2 mmol) and HATU (9.96 g, 26.2 mmol) were added. RM was stirred at RT for 15 min and 3-(trifluoromethyl)aniline (1.964 ml, 15.72 mmol) was added. The RM was stirred at 40° C. overnight. RM was diluted with DCM and water was added. This mixture was stirred 15 min and phases separated, organic phases was washed with water, 5% wt solution of citric acid, twice with water and brine, dryed over $Na_2SO_4$, filtered and concentrated under reduced pressure. Crude material was purified by FCC (DCM to 10% MeOH in DCM) to afford the title compound (4.36 g, 10.22 mmol, 78% yield).

$^1$H NMR (300 MHz, DMSO-d6) δ 10.38 (s, 1H), 8.19 (d, J=2.0 Hz, 1H), 8.16 (s, 1H), 8.00-7.92 (m, 1H), 7.58 (t, J=8.0 Hz, 1H), 7.47-7.38 (m, 1H), 4.59 (s, 2H), 3.58 (t, J=5.8 Hz, 2H), 2.85 (t, J=5.8 Hz, 2H), 1.43 (s, 9H).

Step 2; N-(3-(trifluoromethyl)phenyl)-4,5,6,7-tetrahydrothieno[2,3-c]pyridine-3-carboxamide hydrochloride (Intermediate 14)

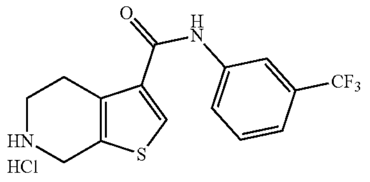 [SMILES: O=C(Nc1cccc(C(F)(F)F)c1)c1csc2c1CCNC2 ; Cl]

Intermediate 13 (2.82 g, 6.61 mmol) was dissolved in minimal amount of DCM (6.01 ml) then $Et_2O$ (60.1 ml) was added, followed by 4N HCl in Dioxane (16.53 ml, 66.1 mmol) and the RM was stirred at RT overnight. $Et_2O$ was added to RM till no more precipitation was observed, then solid was filtered off and residual solvent evaporated under vacuum, and title compound was obtained (2.3353 g, 6.44 mmol, 97% yield).

$^1$H NMR (300 MHz, DMSO-d6) δ 10.51 (s, 1H), 8.27 (s, 1H), 8.16 (d, J=2.1 Hz, 1H), 7.95-7.86 (m, 1H), 7.58 (t, J=8.0 Hz, 1H), 7.48-7.40 (m, 1H), 4.36 (s, 2H), 3.36 (td, J=6.5, 5.1 Hz, 2H), 3.09 (t, J=6.1 Hz, 2H).

Step 3; 6-((4-aminopyridin-3-yl)methyl)-N-(3-(trifluoromethyl)phenyl)-4,5,6,7-tetrahydrothieno[2,3-c]pyridine-3-carboxamide (Intermediate 15)

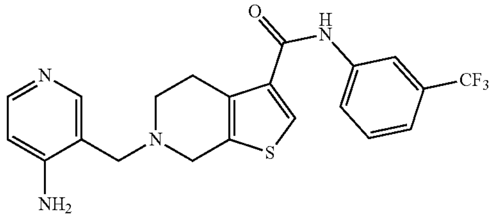 [SMILES: Nc1ccncc1CN1CCc2c(C(=O)Nc3cccc(C(F)(F)F)c3)csc2C1]

Intermediate 14 (100 mg, 0.276 mmol) and 4-aminonicotinaldehyde (37.0 mg, 0.303 mmol) were weighed in a reaction tube which was backfilled with argon (×3). MeOH (1378 μl) was added followed by AcOH (47.3 μl, 0.827 mmol) and the solution was stirred for 1 h at 50° C. $NaBH_3CN$ (78 mg, 1.240 mmol) was added to the reaction mixture and stirred at 50° C. until LCMS indicated consumption of starting material. Further addictions of aldehyde (1.2 eq) and $NaBH_3CN$ (1 eq) were necessary to lead a full conversion. The reaction mixture was transferred to a separatory funnel and diluted with DCM. $NaHCO_3$ (sat) was added and the organic layers separated (×3). The combined organic layers were washed once with brine, concentrated under vacuum and the crude material purified via FCC (0-2% 6.5M $NH_3$ in MeOH and 10% MeOH in DCM) to afford the title compound (75 mg, 0.173 mmol, 62.9% yield).

$^1$H NMR (300 MHz, DMSO-d6) δ 10.35 (s, 1H), 8.19 (d, J=2.1 Hz, 1H), 8.11 (s, 1H), 7.97 (d, J=8.3 Hz, 3H), 7.58 (t, J=8.0 Hz, 1H), 7.43 (d, J=7.8 Hz, 1H), 6.54 (d, J=5.5 Hz, 1H), 6.08 (s, 2H), 3.61 (d, J=3.3 Hz, 4H), 2.87 (d, J=5.9 Hz, 2H), 2.71 (t, J=5.7 Hz, 2H).

Step 4: 6-((4-(2-methoxyacetamido)pyridin-3-yl)methyl)-N-(3-(trifluoromethyl)phenyl)-4,5,6,7-tetrahydrothieno[2,3-c]pyridine-3-carboxamide Example 17

A flask containing Intermediate 15 (75 mg, 0.173 mmol) was backfilled with argon (×3). THE (867 μl) was added to dissolve the starting material followed by TEA (48.3 μl, 0.347 mmol) and the reaction mixture was stirred for 10 mins before 2-methoxyacetyl chloride (20.70 mg, 0.191 mmol) was added at 0° C. The reaction mixture was stirred for 1 h and after confirming completion by UPLC, the reaction mixture was transferred to a separatory funnel and quenched with water. The desired product was extracted with DCM (×3) and the combined organic layers were washed once with brine (×1) and concentrated. The crude material was purified by prepHPLC, then triturated with water to afford the tile compound (22.38 mg, 0.044 mmol, 25.6% yield).

$^1$H NMR (300 MHz, DMSO-d6) δ 11.33 (s, 1H), 10.38 (s, 1H), 8.49-8.38 (m, 2H), 8.24-8.12 (m, 3H), 7.98 (d, J=8.2 Hz, 1H), 7.58 (t, J=8.0 Hz, 1H), 7.43 (d, J=7.8 Hz, 1H), 3.96 (s, 2H), 3.86 (s, 2H), 3.71 (s, 2H), 3.11 (s, 3H), 2.94 (s, 2H), 2.78 (d, J=5.6 Hz, 2H). LC-MS (ESI): m/z (M+1)=505.1; $t_R$=2.27 min. Method 2

The following compounds were prepared via reductive amination as described for Example 17, step 1-4, applying the previously synthesized or commercially available aryl aldehyde in step 3. Such procedures may involve minor variations. In some cases, where modifications involve the used procedure or chromatographic purification conditions, such changes are reported in the table.

| Example No | Structure | Reagents amount | Product Amount (yield) | Purification | Data |
|---|---|---|---|---|---|
| 18 | 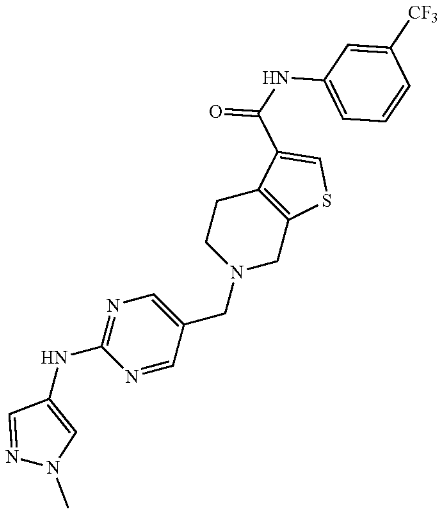 [SMILES: Cn1cc(Nc2ncc(CN3CCc4c(C(=O)Nc5cccc(C(F)(F)F)c5)csc4C3)cn2)cn1] | Intermediate 15: 100 mg (1 eq.) Intermediate 1: 1.1 eq. | 32 mg (23%) | prepHPLC | $^1$H NMR (300 MHz, DMSO-d6) δ 10.34 (s, 1H), 9.43 (s, 1H), 8.37 (s, 2H), 8.19 (s, 1H), 8.10 (s, 1H), 7.96 (d, J = 8.2 Hz, 1H), 7.89 (s, 1H), 7.57 (t, J = 8.0 Hz, 1H), 7.49-7.38 (m, 2H), 3.80 (s, 3H), 3.63 (s, 2H), 3.57 (s, 2H), 2.87 (s, 2H), 2.73 (d, J = 5.4 Hz, 2H). LC-MS (ESI): method 7 $t_R$ = 1.87 min; m/z (M + 1) = 514.1 |

-continued

| Example No | Structure | Reagents amount | Product Amount (yield) | Purification | Data |
|---|---|---|---|---|---|
| 19 | 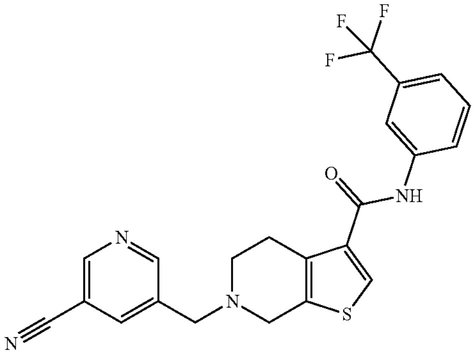 [SMILES: N#Cc1cncc(CN2CCc3c(C(=O)Nc4cccc(C(F)(F)F)c4)csc3C2)c1] | General procedure C 5-Formyl-3-pyridinecarbonitrile: 22 mg (0.153 mmol) Intermediate 15: 55 mg (1.0) eq. | 9.5 mg (14%) | prepHPLC | $^1$H NMR (400 MHz, DMSO) δ 10.36 (s, 1H), 8.97 (d, J = 2.0 Hz, 1H), 8.87 (d, J = 2.0 Hz, 1H), 8.29 (t, J = 2.0 Hz, 1H), 8.21 (s, 1H), 8.13 (s, 1H), 7.98 (d, J = 8.7 Hz, 1H), 7.59 (t, J = 8.0 Hz, 1H), 7.44 (d, J = 7.8 Hz, 1H), 3.81 (s, 2H), 3.69 (s, 2H), 2.90 (t, J = 5.6 Hz, 2H), 2.77 (t, J = 5.7 Hz, 2H). LC-MS (ESI): method 9 $t_R$ = 3.70 min; m/z (M + 1) = 443.2 |
| 20 | 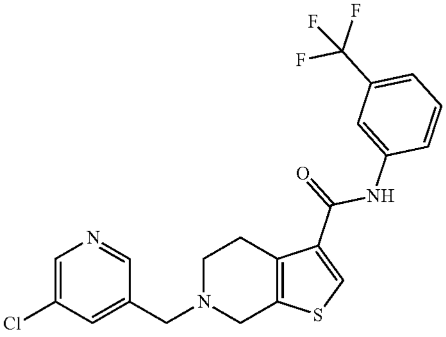 [SMILES: O=C(Nc1cccc(C(F)(F)F)c1)c1csc2c1CCN(Cc1cncc(Cl)c1)C2] | General procedure C 5-Chloro-3-pyridinecarboxaldehyde: 21 mg (0.153 mmol) Intermediate 15: 55 mg (1.0 eq.) | 9.5 mg (14%) | prepHPLC | $^1$H NMR (400 MHz, DMSO) δ 10.36 (s, 1H), 8.57 (d, J = 2.4 Hz, 1H), 8.54 (d, J = 1.8 Hz, 1H), 8.21 (s, 1H), 8.12 (s, 1H), 7.98 (d, J = 8.5 Hz, 1H), 7.92 (t, J = 2.1 Hz, 1H), 7.59 (t, J = 8.0 Hz, 1H), 7.44 (d, J = 7.8 Hz, 1H), 3.77 (s, 2H), 3.68 (s, 2H), 2.89 (t, J = 5.5 Hz, 2H), 2.76 (t, J = 5.8 Hz, 2H). LC-MS (ESI): method 9 $t_R$ = 3.77 min; m/z (M + 1) = 452.4 |
| 21 | 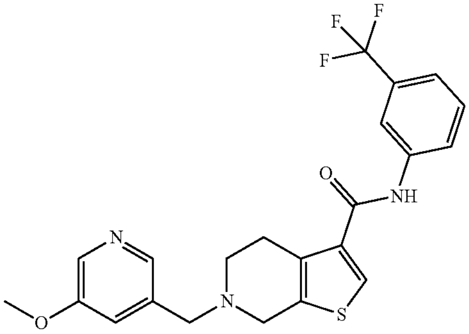 [SMILES: COc1cncc(CN2CCc3c(C(=O)Nc4cccc(C(F)(F)F)c4)csc3C2)c1] | General procedure C 5-Methoxy-3-pyridinecarboxaldehyde: 19 mg (0.153 mmol) Intermediate 15: 55 mg (1.0 eq) | 24 mg (35%) | prepHPLC | $^1$H NMR (400 MHz, DMSO) & 10.36 (s, 1H), 8.23 (d, J = 2.9 Hz, 1H), 8.22-8.20 (m, 1H), 8.17 (d, J = 1.5 Hz, 1H), 8.12 (s, 1H), 7.98 (d, J = 8.5 Hz, 1H), 7.59 (t, J = 8.0 Hz, 1H), 7.44 (d, J = 7.8 Hz, 1H), 7.36 (dd, J = 1.8, 2.8 Hz, 1H), 3.85 (s, 3H), 3.74 (s, 2H), 3.67 (s, 2H), 2.92-2.87 (m, 2H), 2.77-2.73 (m, 2H). LC-MS (ESI): method 9 $t_R$ = 3.48 min; m/z (M + 1) = 448.2 |
| 22 | 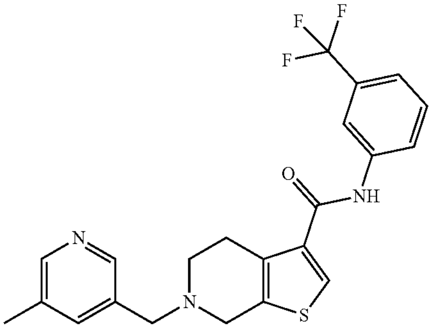 [SMILES: Cc1cncc(CN2CCc3c(C(=O)Nc4cccc(C(F)(F)F)c4)csc3C2)c1] | General procedure C 5-Methyl-3-pyridinecarboxaldehyde: 27 mg (0.153 mmol) Intermediate 15: 55 mg (1.0 eq) | 32 mg (47%) | prepHPLC | $^1$H NMR (400 MHz, DMSO) & 10.35 (s, 1H), 8.36 (s, 2H), 8.19 (s, 1H), 8.12 (s, 1H), 7.96 (d, J = 8.2 Hz, 1H), 7.62-7.55 (m, 2H), 7.42 (d, J = 7.7 Hz, 1H), 3.75-3.69 (m, 4H), 2.90 (s, 2H), 2.77 (s, 2H), 2.32-2.30 (m, 3H). LC-MS (ESI): method 8 $t_R$ = 5.03 min; m/z (M + 1) = 432.2 |

-continued

| Example No | Structure | Reagents amount | Product Amount (yield) | Purification | Data |
|---|---|---|---|---|---|
| 23 | 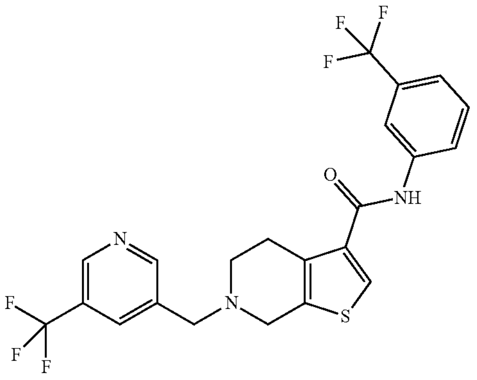 [SMILES: O=C(Nc1cccc(C(F)(F)F)c1)c1csc2c1CCN(Cc1cncc(C(F)(F)F)c1)C2] | General procedure C 5-(Trifluoromethyl)-3-pyridinecarboxaldehyde: 19 mg (0.153 mmol) Intermediate 15: 55 mg (1.0 eq.) | 37 mg (49%) | prepHPLC | $^1$H NMR (400 MHz, DMSO) & 10.36 (s, 1H), 8.90 (dd, J = 1.4, 12.0 Hz, 2H), 8.22-8.12 (m, 3H), 7.98 (d, J = 8.3 Hz, 1H), 7.59 (t, J = 8.0 Hz, 1H), 7.44 (d, J = 7.8 Hz, 1H), 3.87 (s, 2H), 3.71 (s, 2H), 2.90 (t, J = 5.6 Hz, 2H), 2.77 (t, J = 5.8 Hz, 2H). LC-MS (ESI): method 8 $t_R$ = 4.07 min; m/z (M + 1) = 486.2 |
| 24 | 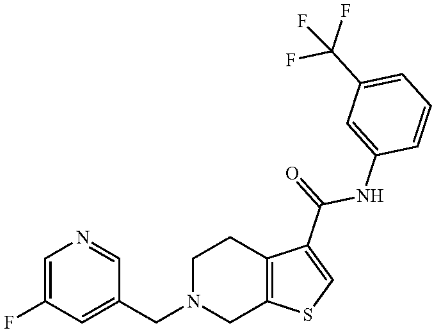 [SMILES: O=C(Nc1cccc(C(F)(F)F)c1)c1csc2c1CCN(Cc1cncc(F)c1)C2] | General procedure C 5-Fluoronicotinaldehyde: 16 mg (0.153 mmol) Intermediate 15: 55 mg (1.0 eq.) | 33 mg (49%) | prepHPLC | $^1$H NMR (400 MHz, DMSO) δ 10.36 (s, 1H), 8.52 (d, J = 2.3 Hz, 1H), 8.47 (s, 1H), 8.21 (s, 1H), 8.13 (s, 1H), 7.98 (d, J = 8.7 Hz, 1H), 7.72 (d, J = 9.9 Hz, 1H), 7.59 (t, J = 8.0 Hz, 1H), 7.44 (d, J = 7.8 Hz, 1H), 3.80 (s, 2H), 3.68 (s, 2H), 2.93-2.87 (m, 2H), 2.76 (t, J = 5.5 Hz, 2H). LC-MS (ESI): method 9 $t_R$ = 3.57 min; m/z (M + 1) = 436.2 |
| 25 | 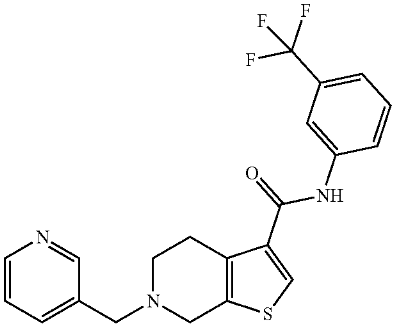 [SMILES: O=C(Nc1cccc(C(F)(F)F)c1)c1csc2c1CCN(Cc1cccnc1)C2] | General procedure C 3-Pyridinecarboxaldehyde: 20 mg (0.153 mmol) Intermediate 15: 55 mg (1.0 eq) | 28 mg (43%) | prepHPLC | $^1$H NMR (400 MHz, DMSO) δ 10.48 (s, 1H), 8.69 (s, 1H), 8.64 (d, J = 3.9 Hz, 1H), 8.32 (s, 1H), 8.25 (s, 1H), 8.09 (d, J = 8.8 Hz, 1H), 7.92 (d, J = 7.7 Hz, 1H), 7.70 (t, J = 8.0 Hz, 1H), 7.57-7.50 (m, 2H), 3.90 (s, 2H), 3.81 (s, 2H), 3.03-2.91 (m, 4H). LC-MS (ESI): method 9 $t_R$ = 3.24 min; m/z (M + 1) = 418.2 |
| 27 | 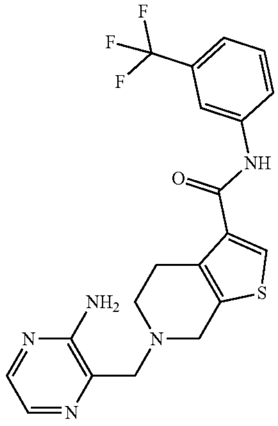 [SMILES: Nc1nccnc1CN1CCc2c(C(=O)Nc3cccc(C(F)(F)F)c3)csc2C1] | General procedure C Workup: RM was washed with $NH_4Cl$, water, water:brine (1:1) and brine then concentrated 3-aminopyrazine-2-carbaldehyde: 38 mg (0.306 mmol, 1.0 eq.) Intermediate 15: 100 mg (1.0 eq) | 27 mg (21%) | prepHPLC | ’H NMR (400 MHz, DMSO-d6) δ 10.40 (s, 1H), 8.24 (s, 1H), 8.17 (s, 1H), 8.02 (d, J = 8.1 Hz, 1H), 7.95 (d, J = 2.8 Hz, 1H), 7.75 (d, J = 2.8 Hz, 1H), 7.63 (t, J = 8.0 Hz, 1H), 7.48 (d, J = 7.8 Hz, 1H), 6.50 (s, 2H), 3.83 (s, 2H), 3.72 (s, 2H), 2.94 (t, J = 5.4 Hz, 2H), 2.79 (t, J = 5.8 Hz, 2H). LC-MS (ESI): Method 8 $t_R$ = 4.71 min; m/z (M + 1) = 434.2 |

-continued

| Example No | Structure | Reagents amount | Product Amount (yield) | Purification | Data |
|---|---|---|---|---|---|
| 28 | 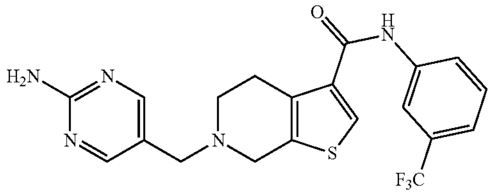 [SMILES: Nc1ncc(CN2CCc3c(C(=O)Nc4cccc(C(F)(F)F)c4)csc3C2)cn1] | General procedure H 2-Aminopyrimidine-5-carboxaldehyde:30 mg, 0.244 mmol, (1.47 eq) Intermediate 15: 60 mg (1.0 eq) | 34 mg (47%) | prepHPLC | $^1$H NMR (400 MHz, DMSO-d6) δ 10.35 (s, 1H), 8.20 (s, 3H), 8.11 (s, 1H), 7.98 (d, J = 7.0 Hz, 1H), 7.59 (t, J = 8.0 Hz, 1H), 7.44 (d, J = 7.8 Hz, 1H), 6.58 (s, 2H), 3.61 (s, 2H), 3.51 (s, 2H), 2.87 (t, J = 5.5 Hz, 2H), 2.71 (t, J = 5.7 Hz, 2H). LC-MS (ESI): Method 9 $t_R$ = 4.21 min; m/z (M + 1) = 434.5 |

Example 29: preparation of 6-((5-(4-methyl-3-oxopiperazin-1-yl)pyridin-3-yl)methyl)-N-(3-(trifluoromethyl)phenyl)-4,5,6,7-tetrahydrothieno[2,3-c]pyridine-3-carboxamide

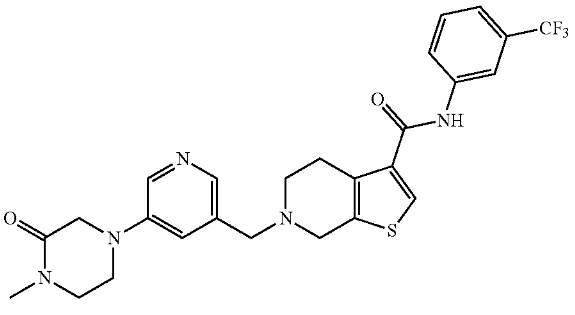 [SMILES: CN1CCN(c2cncc(CN3CCc4c(C(=O)Nc5cccc(C(F)(F)F)c5)csc4C3)c2)CC1=O]

Example 29

Step 1; 6-((5-Bromopyridin-3-yl)methyl-N-(3-(trifluoromethyl)phenyl)-4,5,6,7-tetrahydrothieno[2,3-c]pyridine-3-carboxamide Intermediate 41)

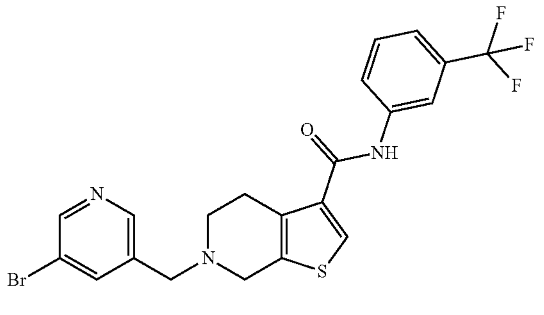 [SMILES: O=C(Nc1cccc(C(F)(F)F)c1)c1csc2c1CCN(Cc1cncc(Br)c1)C2]

To a mixture of intermediate 14 (200 mg, 0.613 mmol, 1.00 eq), $MgSO_4$ (148 mg, 1.23 mmol, 2.00 eq) and 5-bromo-3-pyridinecarboxaldehyde (114 mg, 0.613 mmol, 1.00 eq) in DCM (10 mL), STAB (325 mg, 1.53 mmol, 2.50 eq) was added and the mixture was stirred at room temperature for 21 h. The mixture was slowly added to a saturated acqueous solution of $NaHCO_3$ and extracted with DCM (×3). The combined organic extracts were dried ($Na_2SO_4$) and evaporated. The crude compound was purified the residue was purified by Silica FCC (12 g cartridge, 0-70% EtOAc in cyclohexane) to afford the title compound (128 mg, 0.257 mmol, 42%).

$^1$H NMR (400 MHz, DMSO-d6) δ 10.34 (s, 1H), 8.63 (d, J=2.3 Hz, 1H), 8.55 (d, J=1.7 Hz, 1H), 8.19 (s, 1H), 8.11 (s, 1H), 8.04-7.95 (m, 2H), 7.57 (t, J=8.0 Hz, 1H), 7.44-7.41 (m, 1H), 3.75 (s, 2H), 3.67-3.65 (m, 2H), 2.88 (t, J=5.6 Hz, 2H), 2.74 (t, J=5.7 Hz, 2H).

Step 2: 6-((5-(4-methyl-3-oxopiperazin-1-yl)pyridin-3-yl)methyl)-N-(3-(trifluoromethyl)phenyl)-4,5,6,7-tetrahydrothieno[2,3-c]pyridine-3-carboxamide Example 29

A mixture of Intermediate 41 (50 mg, 0.101 mmol, 1.00 eq), 1-methylpiperazin-2-one (13 mg, 0.111 mmol, 1.10 eq) and $Cs_2CO_3$ (66 mg, 0.201 mmol, 2.00 eq) in anhydrous 1,4-dioxane (1.50 mL) was degassed and RuPhos Pd G3 (8.4 mg, 0.0101 mmol, 0.10 eq) was added. The reaction mixture was stirred at 80° C. under argon for 21 h. The reaction mixture was cooled, filtered through a pad of celite and concentrated. Purification by reverse phase HPLC (Sunfire C18 19×150 mm, 10 um 20-80% ACN/H2O (10 mM NH4CO3), 20 ml/min, RT) gave the title compound (15.8 mg, 29%)

$^1$H NMR (400 MHz, DMSO-d6) δ 10.36 (s, 1H), 8.23 (d, J=2.9 Hz, 1H), 8.21 (s, 1H), 8.12 (s, 1H), 8.02 (d, J=1.5 Hz, 1H), 7.98 (d, J=8.7 Hz, 1H), 7.59 (t, J=8.0 Hz, 1H), 7.45-7.43 (m, 1H), 7.31 (t, J=2.1 Hz, 1H), 3.85 (s, 2H), 3.69 (s, 2H), 3.66 (s, 2H), 3.57 (dd, J4.3, 6.4 Hz, 2H), 3.46 (dd, J4.4, 6.6 Hz, 2H), 2.92-2.91 (m, 3H), 2.90-2.88 (m, 2H), 2.74 (t, J=5.8 Hz, 2H). LC-MS (ESI): m/z (M+1)=530; $t_R$=3.06 min. Method 9

The following compound was prepared via Hartwig-Buchwald C—N coupling as described for Example 29, step 1-2, applying the commercially available amine in step 2. Such procedures may involve minor variations.

| Ex. No | Structure | Reagents Amount | Product Amount (yield) | Purification | Data |
|---|---|---|---|---|---|
| 30 | 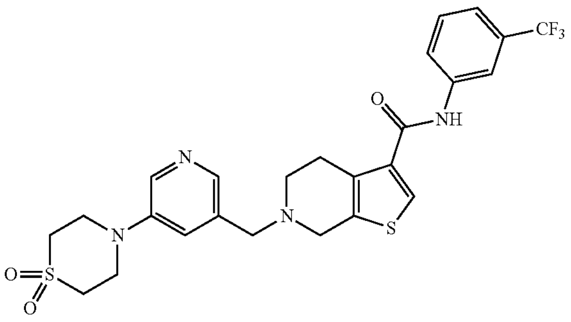 [SMILES: O=C(Nc1cccc(C(F)(F)F)c1)c1csc2c1CCN(Cc1cncc(N3CCS(=O)(=O)CC3)c1)C2] | Intermediate 41: 50 mg, 0.101 mmol (1 eq.) 1,4-thiazinane 1,1-dioxide: 15 mg, 0.111 mmol, 1.10 eq | 7 mg (13%) | prepHPLC | $^1$H NMR (400 MHz, DMSO-d6) δ 10.36 (s, 1H), 8.32 (d, J = 2.9 Hz, 1H), 8.21 (s, 1H), 8.12 (s, 1H), 8.04 (d, J = 1.5 Hz, 1H), 7.98 (d, J = 8.3 Hz, 1H), 7.59 (t, J = 8.0 Hz, 1H), 7.46-7.42 (m, 1H), 7.40 (dd, J = 1.7, 2.7 Hz, 1H), 3.87-3.81 (m, 4H), 3.69 (s, 2H), 3.67 (s, 2H), 3.20-3.15 (m, 4H), 2.91-2.88 (m, 2H), 2.77-2.73 (m, 2H). LC-MS (ESI): Method 9 $t_R$ = 3.21 min; m/z (M + 1) = 551.3 |

Example 31: preparation of N-6-((5-(2-(Dimethylamino)acetamido)pyridine-3-yl)methyl-N-(3-(trifluoromethyl)phenyl)-4,5,6,7-tetrahydrothieno[2,3-c]pyridine-3-carboxamide

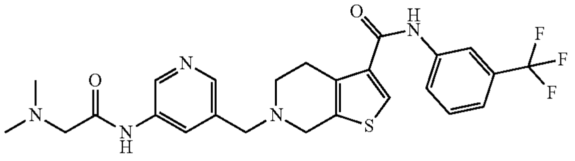 [SMILES: CN(C)CC(=O)Nc1cncc(CN2CCc3c(C(=O)Nc4cccc(C(F)(F)F)c4)csc3C2)c1]

Example 31

Step 1; preparation of N-6-((5-(2-(Dimethylamino)acetamido)pyridine-3-yl)methyl-N-(3-(trifluoromethyl)phenyl)-4,5,6,7-tetrahydrothieno[2,3-c]pyridine-3-carboxamide (Example 31)

A degassed (argon) mixture of aluminum trifluoromethanesulfonate (1.9 mg, 4.03 μmol, 0.100 eq), Intermediate 41 (20 mg, 0.0403 mmol, 1.00 eq), 2-(dimethylamino)acetamide (4.1 mg, 0.0403 mmol, 1.00 eq), $Pd(dba)_2$ (2.3 mg, 4.03 mmol, 0.100 eq), XantPhos (2.3 mg, 4.03 mmol, 0.100 eq) and $Cs_2CO_3$ (13 mg, 0.0403 mmol, 1.00 eq) in toluene (2.00 mL) was heated at 110° C. for 64 h. The reaction mixture was diluted with DCM (15 mL), dried ($Na_2SO_4$) and evaporated. The crude was purified by reverse phase preparative HPLC (Luna Phenyl-Hexyl 21.2×150 mm, 10 um 20-80% $MeOH/H_2O$ (0.1% FA), 20 ml/min, RT) gave the title compound (7 mg, 34%)

$^1$H NMR (400 MHz, DMSO-d6) δ 10.37 (s, 1H), 9.99 (s, 1H), 8.76 (d, J=2.4 Hz, 1H), 8.24 (t, J=1.6 Hz, 1H), 8.21 (t, J=2.0 Hz, 1H), 8.16 (t, J=2.0 Hz, 1H), 8.12 (s, 1H), 8.00-7.96 (m, 1H), 7.62-7.56 (m, 1H), 7.45-7.42 (m, 1H), 3.72 (s, 2H), 3.66 (s, 2H), 3.11 (s, 2H), 2.90 (t, J=5.4 Hz, 2H), 2.75 (t, J=6.4 Hz, 2H), 2.29 (s, 6H). LC-MS (ESI): m/z (M+1)=518.3; $t_R$=2.71 min. Method 9.

Example 32: preparation of 6-((5-methoxypyridin-3-yl)methyl)-N-(5-(trifluoromethyl)pyridin-3-yl)-4,5,6,7-tetrahydrothieno[2,3-c]pyridine-3-carboxamide

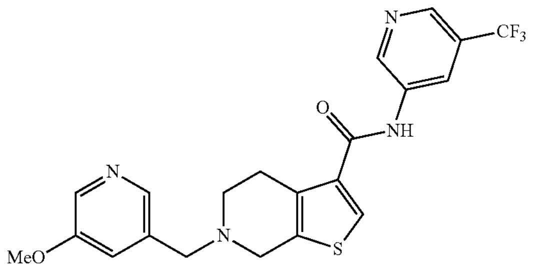 [SMILES: COc1cncc(CN2CCc3c(C(=O)Nc4cncc(C(F)(F)F)c4)csc3C2)c1]

Example 32

Step 1: preparation of tert-butyl 3-((5-(trifluoromethyl)pyridin-3-yl)carbamoyl)-4,7-dihydrothieno[2,3-c]pyridine-6(5H)-carboxylate (Intermediate 42)

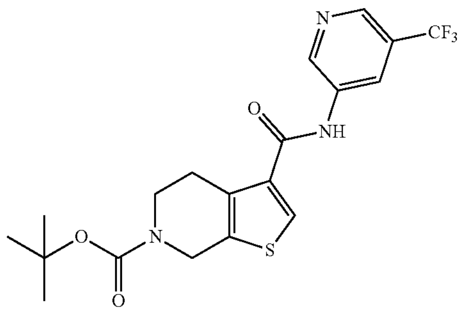 [SMILES: CC(C)(C)OC(=O)N1CCc2c(C(=O)Nc3cncc(C(F)(F)F)c3)csc2C1]

Prepared from 6-tert-butoxycarbonyl-5,7-dihydro-4H-thieno[2,3-c]pyridine-3-carboxylic acid (250 mg, 0.882 mmol, 1.00 eq) and 5-(trifluoromethyl)pyridin-3-amine (157 mg, 0.971 mmol, 1.10 eq) according to general procedure G. The residue was purified by silica FCC (80 g cartridge, 0-25% EtOAc in cyclohexane+0.1% NEt3) gave the title compound (265 mg, 70%).

$^1$H NMR (400 MHz, DMSO-d6) δ 10.63 (s, 1H), 9.12 (d, J=2.3 Hz, 1H), 8.68 (d, J=1.0 Hz, 1H), 8.58 (t, J=1.9 Hz, 1H), 8.22 (s, 1H), 4.60 (s, 2H), 3.61-3.56 (m, 2H), 2.89-2.84 (m, 2H), 1.43 (s, 9H).

Step 2: preparation of N-(5-(trifluoromethyl)pyridin-3-yl)-4,5,6,7-tetrahydrothieno[2,3-c]pyridine-3-carboxamide Intermediate 43)

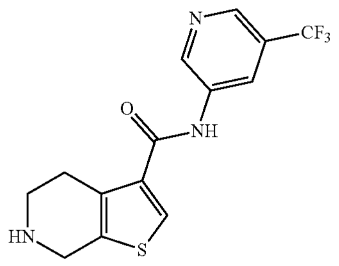 [SMILES: O=C(Nc1cncc(C(F)(F)F)c1)c1csc2c1CCNC2]

To a stirred solution of Intermediate 42 (290 mg, 0.678 mmol, 1.00 eq) in anhydrous DCM (6.78 mL), cooled over an ice/water bath under an argon atmosphere, TFA (0.52 mL, 6.78 mmol, 10.0 eq) was added dropwise over 5 min. The reaction mixture was stirred for 3 h. Further TFA (0.17 mL, 2.26 mmol, 3.33 eq) was added, the reaction mixture was allowed to warm to room temperature and stirred for 1 h. The reaction mixture was concentrated under vacuum, the residue was dissolved in 1:1 DCM:MeOH and applied to a MeOH pre-conditioned 5 g Isolute SCX-II cartridge, washed with MeOH, then released with 2 M $NH_3$/MeOH. The 2 M $NH_3$/MeOH eluent was concentrated under vacuum to give the title compound (193 mg, 87%).

$^1$H NMR (400 MHz, DMSO-d6) δ 10.58 (s, 1H), 9.12 (d, J=2.3 Hz, 1H), 8.67 (d, J=1.0 Hz, 1H), 8.59-8.57 (m, 1H), 8.12 (s, 1H), 3.88 (s, 2H), 3.17 (d, J=5.0 Hz, 1H), 2.90 (t, J=5.7 Hz, 2H), 2.78-2.73 (m, 2H).

Step 3: preparation of 6-((5-methoxypyridin-3-yl)methyl)-N-(5-(trifluoromethyl)pyridin-3-yl)-4,5,6,7-tetrahydrothieno[2,3-c]pyridine-3-carboxamide (Example 32)

Prepared from Intermediate 43 (45 mg, 0.138 mmol) and 5-Methoxy-3-pyridinecarboxaldehyde (18 mg, 0.131 mmol) according to general procedure D. Purification by reverse phase preparative HPLC (Xbridge Phenyl 19×150 mm, 10 μm 40-100% MeOH/water (10 mM $NH_4HCO_3$), 20 mL/min, RT) gave the title compound (19 mg, 30%).

$^1$H NMR (400 MHz, DMSO-d6) δ 10.61 (s, 1H), 9.13 (d, J=2.3 Hz, 1H), 8.69 (d, J=1.0 Hz, 1H), 8.60-8.59 (m, 1H), 8.23 (d, J=2.9 Hz, 1H), 8.19-8.16 (m, 2H), 7.36 (dd, J=1.8, 2.8 Hz, 1H), 3.85 (s, 3H), 3.74 (s, 2H), 3.67 (s, 2H), 2.93-2.88 (m, 2H), 2.78-2.72 (m, 2H). LC-MS (ESI): m/z (M+1)=449.4; $t_R$=2.95 min. Method 9.

The following compounds were prepared via reductive amination as described for Example 32, step 1-3, applying the previously synthesized or commercially available aryl aldehyde in step 3. Such procedures may involve minor variations. In some cases, where modification involved reductive agents (e.g. $NaBH_3CN$ instead of STAB) or chromatographic purification conditions, such changes were reported in the table.

| Example No | Structure | Reagents Amount | Product Amount (yield) | Purification | Data |
|---|---|---|---|---|---|
| 33 | 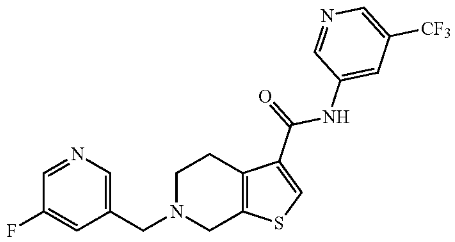 [SMILES: O=C(Nc1cncc(C(F)(F)F)c1)c1csc2c1CCN(Cc1cncc(F)c1)C2] | Intermediate 43: 49 mg, 0.151 mmol (1 eq.) 5-fluoropyridine-3-carbaldehyde: 18 mg, 0.144 mmol, (0.95 eq) | 35 mg (54%) | prepHPLC | $^1$H NMR (400 MHz, DMSO-d6) δ 10.60 (s, 1H), 9.13 (d, J = 2.3 Hz, 1H), 8.69 (d, J = 1.1 Hz, 1H), 8.59 (t, J = 1.9 Hz, 1H), 8.52 (d, J = 2.8 Hz, 1H), 8.47 (t, J = 1.7 Hz, 1H), 8.18 (s, 1H), 7.72 (ddd, J = 1.7, 2.7, 9.8 Hz, 1H), 3.80 (s, 2H), 3.69 (s, 2H), 2.94-2.88 (m, 2H), 2.79-2.74 (m, 2H). LC-MS (ESI): Method 9 $t_R$ = 3.05 min; m/z (M + 1) = 437.2 |
| 34 | 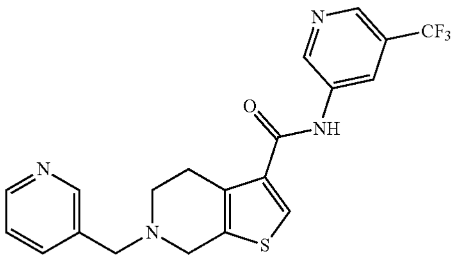 [SMILES: O=C(Nc1cncc(C(F)(F)F)c1)c1csc2c1CCN(Cc1cccnc1)C2] | Intermediate 43: 48 mg, 0.147 mmol (1 eq.) 3-pyridinecarboxaldehyde: 0.013 mL, 0.140 mmol (0.95 eq) | 40 mg (67%) | prepHPLC | $^1$H NMR (400 MHz, DMSO) δ 10.60 (s, 1H), 9.13 (d, J = 2.4 Hz, 1H), 8.69 (d, J = 1.0 Hz, 1H), 8.61-8.58 (m, 1H), 8.57 (d, J = 1.9 Hz, 1H), 8.51 (dd, J = 1.7, 4.8 Hz, 1H), 8.18 (s, 1H), 7.79 (td, J = 1.9, 7.8 Hz, 1H), 7.40 (ddd, J = 0.7, 4.8, 7.8 Hz, 1H), 3.75 (s, 2H), 3.66 (s, 2H), 2.93-2.87 (m, 2H), 2.78-2.73 (m, 2H). LC-MS (ESI): Method 9 $t_R$ = 2.72 min; m/z (M + 1) = 419.3. |

-continued

| Example No | Structure | Reagents Amount | Product Amount (yield) | Purification | Data |
|---|---|---|---|---|---|
| 35 | 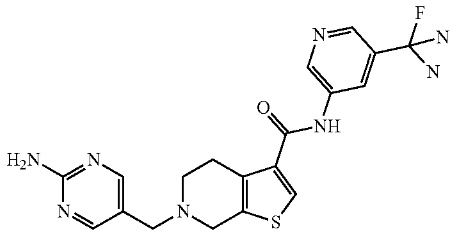 [SMILES: Nc1ncc(CN2CCc3c(C(=O)Nc4cncc(C(N)(N)F)c4)csc3C2)cn1] | Intermediate 43 HCl salt: 50 mg, 0.13 mmol (1 eq.) 2-aminopyrimidine-5-carboxaldehyde: 16 mg, 0.13 mmol (1.00 eq) | 19 mg (31%) | prepHPLC | $^1$H NMR (400 MHz, DMSO-d6) δ 10.59 (s, 1H), 9.13 (d, J = 2.3 Hz, 1H), 8.69 (d, J = 1.1 Hz, 1H), 8.60 (t, J = 2.0 Hz, 1H), 8.20 (s, 2H), 8.17 (s, 1H), 6.59 (s, 2H), 3.62 (s, 2H), 3.52 (s, 2H), 2.88 (t, J = 5.2 Hz, 2H), 2.74-2.67 (m, 2H). LC-MS (ESI): Method 9 $t_R$ = 4.02 min; m/z (M + 1) = 435.3 |
| 36 | 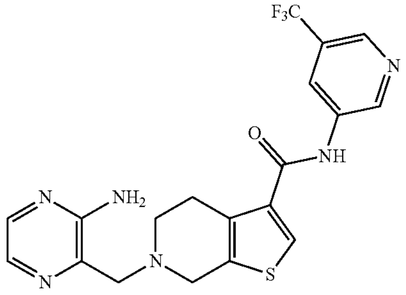 [SMILES: Nc1nccnc1CN1CCc2c(C(=O)Nc3cncc(C(F)(F)F)c3)csc2C1] | Intermediate 43: 109 mg, 0.336 mmol (1 eq.) 3-aminopyrazine-2-carbaldehyde: 41 mg, 0.336 mmol, (1.00 eq) | 30 mg (20%) | prepHPLC | $^1$H NMR (400 MHz, DMSO-d6) d 10.61 (s, 1H), 9.13 (d, J = 2.3 Hz, 1H), 8.69 (s, 1H), 8.59 (t, J = 2.1 Hz, 1H), 8.19 (s, 1H), 7.91 (d, J = 2.8 Hz, 1H), 7.71 (d, J = 2.8 Hz, 1H), 6.46 (s, 2H), 3.79 (s, 2H), 3.69 (s, 2H), 2.91 (t, J = 5.5 Hz, 2H), 2.76 (t, J = 5.8 Hz, 2H). LC-MS (ESI): Method 8 $t_R$ = 4.14 min; m/z (M + 1) = 435.2 |

Example 37: preparation of N-[3-fluoro-5-(trifluoromethyl)phenyl]-6-[[2-(oxetan-3-ylamino)pyrimidin-5-yl]methyl]-5,7-dihydro-4H-thieno[2,3-c]pyridine-3-carboxamide

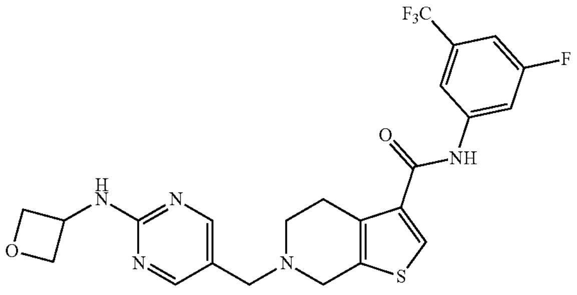 [SMILES: O=C(Nc1cc(F)cc(C(F)(F)F)c1)c1csc2c1CCN(Cc1cnc(NC3COC3)nc1)C2]

Example 37

Step 1: preparation of N-(3-Fluoro-5-(trifluoromethyl)phenyl)-4,5,6,7-tetrahydrothieno[2,3-c]pyridine-3-carboxamide (Intermediate 44)

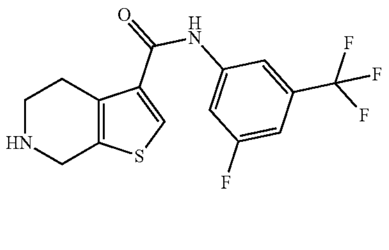 [SMILES: O=C(Nc1cc(F)cc(C(F)(F)F)c1)c1csc2c1CCNC2]

To a solution of 6-tert-butoxycarbonyl-5,7-dihydro-4H-thieno[2,3-c]pyridine-3-carboxylic acid (1590 mg, 5.61 mmol, 1.00 eq) and HATU (2560 mg, 6.73 mmol, 1.20 eq) in DMF (22.50 mL) was added DIPEA (2.9 mL, 16.8 mmol, 3.00 eq) and the RM was stirred at room temperature for 15 minutes before addition of 3-fluoro-5-(trifluoromethyl)aniline (1055 mg, 5.89 mmol, 1.05 eq). The reaction mixture was stirred at room temperature for a further 16 hours. The reaction mixture was purified by silica FCC (EtOAc/cyclohexane from 0% to 100) to yield tert-butyl 3-((3-fluoro-5-(trifluoromethyl)phenyl)carbamoyl)-4,7-dihydrothieno[2,3-c]pyridine-6(5H)-carboxylate, (1.35 g, 3.04 mmol, 1.00 eq) that was dissolved in DCM (35 mL) and TFA (5.0 mL, 65.9 mmol, 21.7 eq) was added. The reaction mixture was stirred at room temperature for 2 hours and concentrated under reduced pressure. The reaction mixture was partitioned between saturated aqueous $Na_2CO_3$ (50 mL) and EtOAc (40 mL) Aqueous layer were extracted with EtOAc (30 mL), dried with $MgSO_4$, filtered through a hydrophobic frit and concentrated under reduced pressure. The crude was purified on silica FCC (EtOAc/cyclohexane from 0% to 100% followed 3:1 EtOAc:EtOH/EtOAc from 0% to 100%) to yield the title compound (500 mg, 2.69 mmol, yield 48%).

$^1$H NMR (400 MHz, $CDCl_3$) δ 7.80 (td, J=2.1, 10.4 Hz, 1H), 7.73 (s, 1H), 7.63 (s, 1H), 7.52 (s, 1H), 7.10 (d, J=8.3 Hz, 1H), 4.07 (s, 2H), 3.15 (t, J=5.8 Hz, 2H), 2.93 (t, J=5.7 Hz, 2H), 1.27-1.22 (m, 1H).

Step 2: preparation of N-[3-fluoro-5-(trifluoromethyl)phenyl]-6-[[2-(oxetan-3-ylamino)pyrimidin-5-yl]methyl]-5,7-dihydro-4H-thieno[2,3-c]pyridine-3-carboxamide (Example 37)

Prepared from Intermediate 20 (62 mg, 0.34 mmol, 1.00 eq) and Intermediate 44 (119 mg, 0.34 mmol, 1.00 eq) according to general procedure C. The residue was purified by reverse phase preparative HPLC (Luna Phenyl-Hexyl 21.2×150 mm, 10 um 20-80% MeOH/H2O (0.1% FA), 20 ml/min, RT). The resulting solid was dissolved in EtOAc, washed with sat. aq. $NaHCO_3$, dried ($MgSO_4$) and concentrated. The residue was lyophilised to give the title compound (12 mg, 7%)

$^1$H NMR (400 MHz, DMSO-d6) δ 10.52 (s, 1H), 8.27 (s, 2H), 8.13 (s, 1H), 7.99-7.90 (m, 3H), 7.38 (d, J=8.5 Hz, 1H), 4.96-4.88 (m, 1H), 4.77 (t, J=6.7 Hz, 2H), 4.52 (t, J=6.3, Hz, 2H), 3.61 (s, 2H), 3.53 (s, 2H), 2.90-2.82 (m, 2H), 2.73-2.68 (m, 2H).

LC-MS (ESI): m/z (M+1)=508.2; $t_R$=2.95 min. Method 8.

The following compounds were prepared via reductive amination as described for Example 37, step 1-2, applying the previously synthesized or commercially available aryl aldehyde in step 2. Such procedures may involve minor variations. In some cases, where modification involved reductive agents (e.g. $NaBH_3CN$ instead of STAB) or chromatographic purification conditions, such changes were reported in the table.

| Example No | Structure | Reagents Amount | Product Amount (yield) | Purification | Data |
|---|---|---|---|---|---|
| 38 | 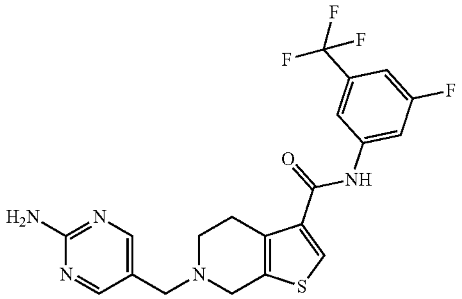 [SMILES: Nc1ncc(CN2CCc3c(C(=O)Nc4cc(F)cc(C(F)(F)F)c4)csc3C2)cn1] | General procedure D Intermediate 44: 40 mg, 0.116 mmol (1 eq.) 2-aminopyrimidine-5-carboxaldehyde: 14 mg, 0.116 mmol (1 eq) | 6 mg (10%) | prepHPLC | $^1$H NMR (400 MHz, DMSO-d6) δ 10.53 (s, 1H), 8.20 (s, 2H), 8.13 (s, 1H), 7.99-7.93 (m, 2H), 7.40-7.36 (m, 1H), 6.59 (s, 2H), 3.61 (s, 2H), 3.51 (s, 2H), 2.87 (t, J = 5.3 Hz, 2H), 2.71 (t, J = 5.8 Hz, 2H). LC-MS (ESI): Method 9 $t_R$ = 3.28 min; m/z (M + 1) = 452.2 |
| 39 | 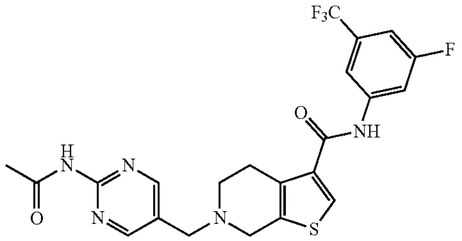 [SMILES: CC(=O)Nc1ncc(CN2CCc3c(C(=O)Nc4cc(F)cc(C(F)(F)F)c4)csc3C2)cn1] | General procedure E Intermediate 44: 60 mg, 0.17 mmol (1 eq.) Intermediate 40: 35 mg, 0.21 mmol (1.2 eq) | 27 mg (31%) | prepHPLC | $^1$H NMR (400 MHz, DMSO-d6) δ 10.50-10.33 (m, 2H), 8.53 (s, 2H), 8.06 (s, 1H), 7.91-7.85 (m, 2H), 7.28 (d, J = 8.3 Hz, 1H), 3.65-3.55 (m, 4H), 2.81 (t, J = 5.7 Hz, 2H), 2.67 (t, J = 5.7 Hz, 2H), 2.11 (s, 3H). LC-MS (ESI): Method 9 $t_R$ = 3.37 min; m/z (M + 1) = 494.5 |
| 40 | 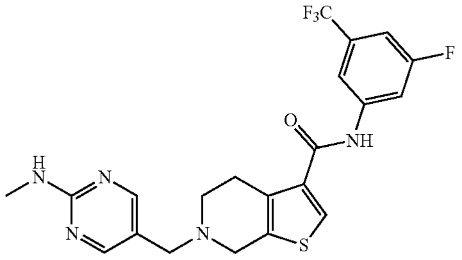 [SMILES: CNc1ncc(CN2CCc3c(C(=O)Nc4cc(F)cc(C(F)(F)F)c4)csc3C2)cn1] | General procedure E Intermediate 44: 60 mg, 0.17 mmol (1 eq.) 2-(methylamino)pyrimidine-5-carbaldehyde: 29 mg, 0.2 mmol (1.2 eq) | 20 mg (20%) | prepHPLC | $^1$H NMR (300 MHz, DMSO-d6) δ 10.52 (s, 1H), 8.24 (s, 2H), 8.13 (s, 1H), 7.99-7.93 (m, 2H), 7.38 (d, J = 8.5 Hz, 1H), 7.05 (q, J = 4.8 Hz, 1H), 3.61 (s, 2H), 3.52 (s, 2H), 2.87 (dd, J = 5.5, 5.5 Hz, 2H), 2.81 (d, J = 4.9 Hz, 3H), 2.71 (dd, J = 5.7, 5.7 Hz, 2H). LC-MS (ESI): Method 9 $t_R$ = 3.42 min; m/z (M + 1) = 466.2 |
| 41 | 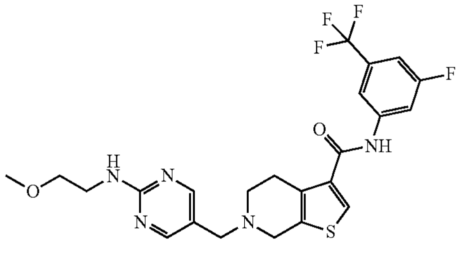 [SMILES: COCCNc1ncc(CN2CCc3c(C(=O)Nc4cc(F)cc(C(F)(F)F)c4)csc3C2)cn1] | General procedure F Intermediate 44: 64 mg, 0.186 mmol (1 eq.) Intermediate 21: 42 mg, 0.371 mmol ( 2.0 eq) | 31 mg (33%) | prepHPLC | $^1$H NMR (400 MHz, DMSO-d6) δ 10.52 (s, 1H), 8.24 (s, 2H), 8.13 (s, 1H), 7.99-7.93 (m, 2H), 7.39 (d, J = 8.4 Hz, 1H), 7.09 (dd, J = 5.2, 5.2 Hz, 1H), 3.61 (s, 2H), 3.52 (s, 2H), 3.46-3.43 (m, 4H), 3.27 (s, 3H), 2.87 (t, J = 5.4 Hz, 2H), 2.74-2.68 (m, 2H). LC-MS (ESI): Method 8 $t_R$ = 4.87 min; m/z (M + 1) = 510.5 |

-continued

| Example No | Structure | Reagents Amount | Product Amount (yield) | Purification | Data |
|---|---|---|---|---|---|
| 42 | 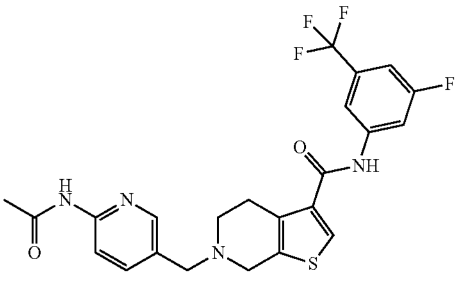 [SMILES: CC(=O)Nc1ccc(CN2CCc3c(C(=O)Nc4cc(F)cc(C(F)(F)F)c4)csc3C2)cn1] | General procedure C Intermediate 44: 80 mg, 0.232 mmol (1 eq.) N-(5-formyl-2-pyridyl)acetamide: 38 mg, 0.232 mmol (1 eq) | 69 mg (60%) | prepHPLC | $^1$H NMR (400 MHz, DMSO-d6) δ 10.53-10.48 (m, 2H), 8.27 (d, J = 1.9 Hz, 1H), 8.13 (s, 1H), 8.07 (d, J = 8.5 Hz, 1H), 7.99-7.93 (m, 2H), 7.75 (dd, J = 2.3, 8.5 Hz, 1H), 7.38 (d, J = 8.5 Hz, 1H), 3.68 (s, 2H), 3.64 (s, 2H), 2.88 (dd, J = 5.3, 5.3 Hz, 2H), 2.74 (dd, J = 5.7, 5.7 Hz, 2H), 2.10 (s, 3H). LC-MS (ESI): Method 8 $t_R$ = 4.85 min; m/z (M + 1) = 493.2 |
| 43 | 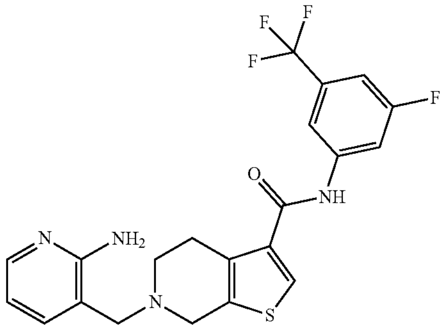 [SMILES: Nc1ncccc1CN1CCc2c(C(=O)Nc3cc(F)cc(C(F)(F)F)c3)csc2C1] | General procedure C Intermediate 44: 100 mg, 0.29 mmol (1 eq.) 2-Amino-3-pyridinecarboxaldehyde: 35 mg, 0.29 mmol (1 eq) | 7.3 mg (6%) | prepHPLC | $^1$H NMR (400 MHz, DMSO-d6) δ 10.53 (s, 1H), 8.15 (s, 1H), 7.99-7.90 (m, 3H), 7.41-7.33 (m, 2H), 6.57-6.54 (m, 1H), 5.99 (s, 2H), 3.64-3.58 (m, 4H), 2.92-2.87 (m, 2H), 2.75-2.68 (m, 2H). LC-MS (ESI): Method 9 $t_R$ = 3.68 min; m/z (M + 1) = 451.2 |
| 44 | 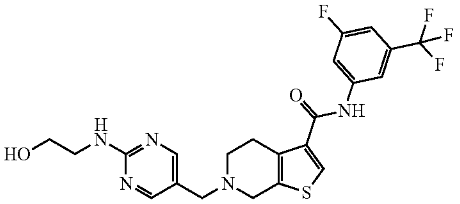 [SMILES: O=C(Nc1cc(F)cc(C(F)(F)F)c1)c1csc2c1CCN(Cc1cnc(NCCO)nc1)C2] | General procedure C Intermediate 44: 70 mg, 0.20 mmol (1 eq) Intermediate 24: 42 mg, 0.40 mmol (2 eq) | 10 mg (10%) | prepHPLC | $^1$H NMR (400 MHz, DMSO-d6) δ 10.52 (s, 1H), 8.23 (s, 2H), 8.13 (s, 1H), 7.99-7.93 (m, 2H), 7.38 (d, J = 8.5 Hz, 1H), 6.99 (t, J = 5.8 Hz, 1H), 4.68 (t, J = 5.5 Hz, 1H), 3.61 (s, 2H), 3.56-3.48 (m, 4H), 3.29 (s, 2H), 2.87 (t, J = 5.3 Hz, 2H), 2.74-2.68 (m, 2H). LC-MS (ESI): Method 9 $t_R$ = 3.32 min; m/z (M + 1) = 496.5 |
| 45 | 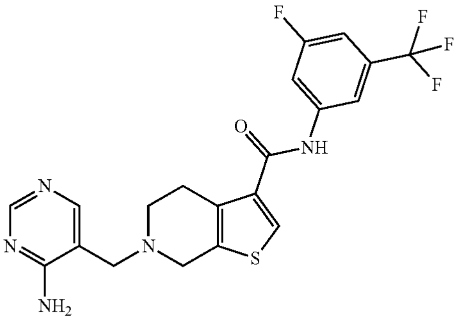 [SMILES: Nc1ncncc1CN1CCc2c(C(=O)Nc3cc(F)cc(C(F)(F)F)c3)csc2C1] | General procedure C Intermediate 44: 100 mg, 0.290 mmol (1 eq) 4-aminopyrimidine-5-carboxaldehyde (35 mg, 0.40 mmol, 1.5 eq) | 29 mg (22%) | prepHPLC | $^1$H NMR (400 MHz, DMSO-d6) δ 10.55 (s, 1H), 8.23 (s, 2H), 8.17 (s, 1H), 8.03-7.96 (m, 2H), 7.41 (d, J = 8.6 Hz, 1H), 6.62 (s, 2H), 3.65 (s, 2H), 3.55 (s, 2H), 2.91 (t, J = 5.7 Hz, 2H), 2.75 (t, J = 5.7 Hz, 2H). LC-MS (ESI): Method 8 $t_R$ = 4.63 min; m/z (M + 1) = 452.4 |

-continued

| Example No | Structure | Reagents Amount | Product Amount (yield) | Purification | Data |
|---|---|---|---|---|---|
| 46 | 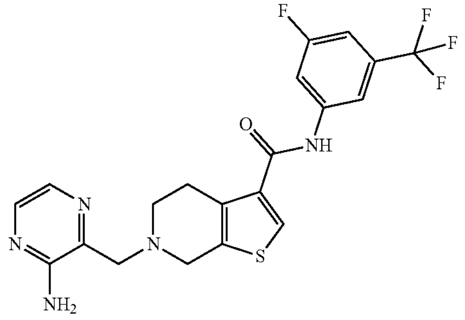 [SMILES: Nc1nccnc1CN1CCc2c(C(=O)Nc3cc(F)cc(C(F)(F)F)c3)csc2C1] | General procedure C Intermediate 44: 100 mg, 0.29 mmol (1 eq) 3-aminopyrazine-2-carbaldehyde: 35 mg, 0.40 mmol (1.5 eq) | 9 mg (6%) | prepHPLC | $^1$H NMR (400 MHz, DMSO-d6) δ 10.54 (s, 1H), 8.13 (s, 1H), 7.92-7.88 (m, 3H), 7.69 (d, J = 2.8 Hz, 1H), 7.35 (d, J = 8.2 Hz, 1H), 6.44 (s, 2H), 3.77 (s, 2H), 3.66 (s, 2H), 2.88 (t, J = 5.5 Hz, 2H), 2.74 (t, J = 5.8 Hz, 2H). LC-MS (ESI): Method 8 $t_R$ = 4.96 min; m/z (M + 1) = 452.2 |
| 47 | 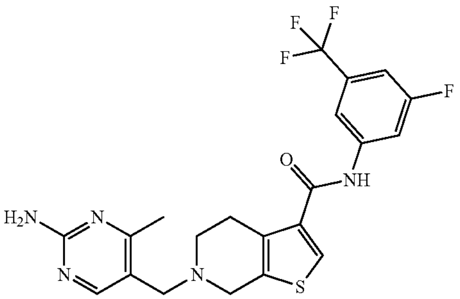 [SMILES: Cc1nc(N)ncc1CN1CCc2c(C(=O)Nc3cc(F)cc(C(F)(F)F)c3)csc2C1] | General procedure C Intermediate 44: 100 mg, 0.29 mmol (1 eq) Intermediate 26 : 80 mg, 0.29 mmol (1 eq, assumed pure 50%) | 7.5 mg (5.5%) | prepHPLC | $^1$H NMR (400 MHz, DMSO-d6) δ 10.52 (s, 1H), 8.13 (s, 1H), 7.99 (s, 1H), 7.97-7.93 (m, 2H), 7.41-7.36 (m, 1H), 6.44 (s, 2H), 3.61 (s, 2H), 3.50 (s, 2H), 2.86 (t, J = 5.8 Hz, 2H), 2.72 (t, J = 5.6 Hz, 2H), 2.32 (s, 3H). LC-MS (ESI): Method 9 $t_R$ = 3.42 min; m/z (M + 1) = 466.2 |

Example 48: preparation of N-[3-fluoro-5-(trifluoromethyl)phenyl]-6-[[6-(methylamino)-3-pyridyl]methyl]-5,7-dihydro-4H-thieno[2,3-c]pyridine-3-carboxamide

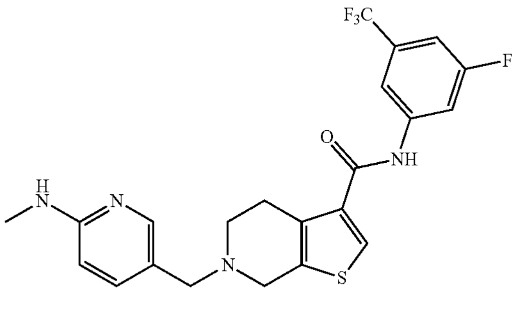 [SMILES: CNc1ccc(CN2CCc3c(C(=O)Nc4cc(F)cc(C(F)(F)F)c4)csc3C2)cn1]

Example 48

Step 1; preparation of N-[3-fluoro-5-(trifluoromethyl)phenyl]-6-[[6-(methylamino)-3-pyridyl]methyl]-5,7-dihydro-4H-thieno[2,3-c]pyridine-3-carboxamide (Example 48)

To a solution of Intermediate 44 HCl salt (150 mg, 0.394 mmol, 1.00 eq), DIPEA (0.14 mL, 0.788 mmol, 2.00 eq) and 6-(methylamino)pyridine-3-carbaldehyde (54 mg, 0.394 mmol, 1.00 eq) in MeOH (7.5 mL) Titanium(IV) isopropoxide (0.35 mL, 1.18 mmol, 3.00 eq) was added. The reaction mixture was heated at reflux overnight. The reaction mixture was allowed to cool to room temperature and $NaBH_3CN$ (62 mg, 0.985 mmol, 2.50 eq) was added. The reaction mixture was stirred at room temperature for 4 hours. The reaction was diluted with DCM, quenched with $NH_4Cl$ and the solid filtered off. The organic layer was separated, and the aqueous layer washed twice with DCM. The combined organic phases were filtered through a hydrophobic frit and the solvent was concentrated under vacuum to afford 190 mg of crude material. The compound was purified by preparative HPLC (Sunfire C18 19×150 mm, 10 um 20-80% ACN/$H_2O$ (10 mM $NH_4CO_3$), 20 ml/min, RT) to afford the title compound (29 mg, 0.0579 mmol, 15%).

$^1$H NMR (400 MHz, DMSO-d6) δ 10.52 (s, 1H), 8.12 (s, 1H), 7.99-7.90 (m, 3H), 7.40-7.35 (m, 2H), 6.45-6.41 (m, 2H), 3.57 (s, 2H), 3.51 (s, 2H), 2.86 (t, J=5.7 Hz, 2H), 2.77 (d, J=4.8 Hz, 3H), 2.71 (t, J=5.8 Hz, 2H). LC-MS (ESI): m/z (M+1)=465.2; $t_R$=2.98 min. Method 9

Example 49: preparation of N-(3-fluoro-5-(trifluoromethyl)phenyl)-6-(1-methyl-1H-imidazole-5-carbonyl)-4,5,6,7-tetrahydrothieno[2,3-c]pyridine-3-carboxamide

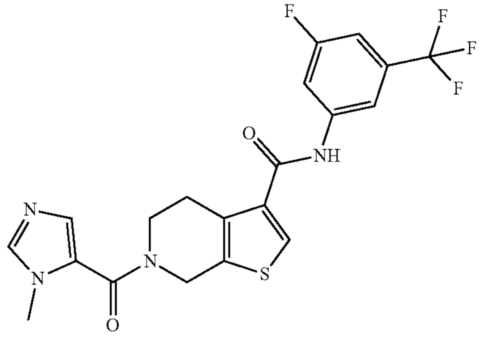 [SMILES: Cn1cncc1C(=O)N1CCc2c(C(=O)Nc3cc(F)cc(C(F)(F)F)c3)csc2C1]

Example 49

Step 1: preparation of N-(3-fluoro-5-(trifluoromethyl)phenyl)-6-(1-methyl-1H-imidazole-5-carbonyl)-4,5,6,7-tetrahydrothieno[2,3-c]pyridine-3-carboxamide Example 49

Prepared from 1-Methyl-1H-imidazole-5-carboxylic acid (22 mg, 0.174 mmol, 1.20 eq) and Intermediate 44 (50 mg, 0.145 mmol, 1.00 eq) according to general procedure A. The residue was purified by preparative HPLC (Xbridge Phenyl 19×150 mm, 10 um 40-100% MeOH/$H_2O$ (10 mM $NH_4CO_3$), 20 ml/min, RT to yield crude product (34 mg). This was repurified by preparative HPLC (Sunfire C18 19×150 mm, 10 um 5-60% ACN/$H_2O$ (0.1% FA), 20 ml/min, RT) to yield the title compound (16 mg, 25%)

$^1$H NMR (400 MHz, DMSO-d6) δ 10.58 (s, 1H), 8.23 (s, 1H), 8.00-7.94 (m, 2H), 7.81 (s, 1H), 7.42-7.38 (m, 1H), 7.35 (d, J=1.0 Hz, 1H), 4.91 (s, 2H), 3.89 (t, J=5.7 Hz, 2H), 3.72 (s, 3H), 3.05-2.98 (m, 2H). LC-MS (ESI): m/z (M+1) =453.3; $t_R$=3.71 min.

Method 9 Example 50: preparation of (R)-6-((2-aminopyrimidin-5-yl)methyl)-N-(3-((3-(dimethylamino)pyrrolidin-1-yl)methyl)-5-(trifluoromethyl)phenyl)-4,5,6,7-tetrahydrothieno[2,3-c]pyridine-3-carboxamide

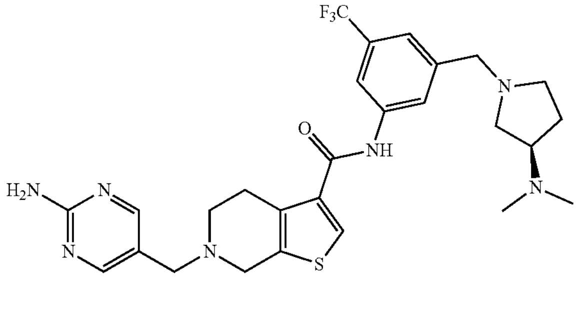 [SMILES: CN(C)[C@@H]1CCN(Cc2cc(NC(=O)c3csc4c3CCN(Cc3cnc(N)nc3)C4)cc(C(F)(F)F)c2)C1]

Example 50

Step 1: preparation of tert-butyl (R)-3-((3-((3-(dimethylamino)pyrrolidin-1-yl)methyl)-5-(trifluoromethyl)phenyl)carbamoyl)-4,7-dihydrothieno[2,3-c]pyridine-6(5H)-carboxylate (Intermediate 45)

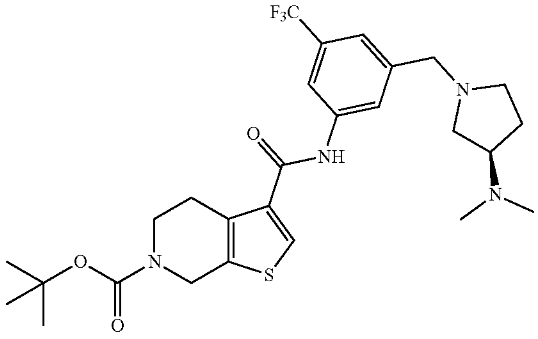 [SMILES: CN(C)[C@@H]1CCN(Cc2cc(NC(=O)c3csc4c3CCN(C(=O)OC(C)(C)C)C4)cc(C(F)(F)F)c2)C1]

Prepared from 6-(tert-butoxycarbonyl)-4,5,6,7-tetrahydrothieno[2,3-c]pyridine-3-carboxylic acid (350 mg, 1.24 mmol, 1.0 eq) and Intermediate 28 (355 mg, 1.24 mmol, 1.0 eq) according to general procedure G. The residue was purified by silica FCC (40 g cartridge, 0-10% 2M $NH_3$/MeOH in DCM) gave the title compound (580 mg, 84%).

$^1$H NMR (300 MHz, $CDCl_3$) δ 8.29-8.22 (m, 2H), 7.86 (s, 1H), 7.67 (s, 1H), 7.19 (s, 1H), 4.61 (s, 2H), 3.70-3.55 (m, 5H), 3.05-2.96 (m, 4H), 2.82 (s, 6H), 2.57 (dd, J=6.4, 11.5 Hz, 1H), 2.46-2.23 (m, 2H), 2.07-1.99 (m, 1H), 1.48 (s, 9H)

Step 2: preparation of (R)—N-(3-((3-(dimethylamino)pyrrolidin-1-yl)methyl)-5-(trifluoromethyl)phenyl)-4,5,6,7-tetrahydrothieno[2,3-c]pyridine-3-carboxamide (Intermediate 46)

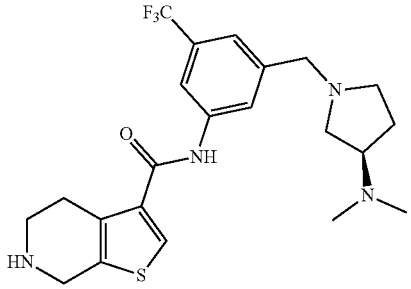 [SMILES: CN(C)[C@@H]1CCN(Cc2cc(NC(=O)c3csc4c3CCNC4)cc(C(F)(F)F)c2)C1]

To a solution of tert-butyl Intermediate 45 (576 mg, 1.04 mmol) in anhydrous DCM (10.4 mL), stirred over an ice/water bath under an atmosphere of argon, was added TFA (1.6 mL, 20.8 mmol), dropwise over 5 min. The reaction mixture was stirred for 1.5 h, concentrated under vacuum and the residue was dissolved in MeOH, applied to a methanol pre-conditioned 20 g Isolute SCX-II cartridge, washed with MeOH, then released with 2M $NH_3$/MeOH. The 2M $NH_3$/MeOH eluent was concentrated under vacuum to give the title compound (356 mg, 75%).

$^1$H NMR (300 MHz, $CDCl_3$) δ 8.00-7.92 (m, 2H), 7.69 (d, J=5.3 Hz, 2H), 7.34 (s, 1H), 4.06 (s, 2H), 3.71 (d, J=13.5 Hz, 1H), 3.59 (d, J=13.3 Hz, 1H), 3.17-3.11 (m, 2H), 2.99-2.92

(m, 2H), 2.87-2.54 (m, 5H), 2.45 (dd, J=6.3, 8.5 Hz, 1H), 2.24 (s, 6H), 2.09-1.95 (m, 1H), 1.84-1.72 (m, 1H)

Step 3: preparation of (R)—N-(3-((3-(dimethylamino)pyrrolidin-1-yl)methyl)-5-(trifluoromethyl)phenyl)-4,5,6,7-tetrahydrothieno[2,3-c]pyridine-3-carboxamide Example 50

Prepared from Intermediate 46 (58 mg, 0.128 mmol) and 2-aminopyrimidine-5-carbaldehyde (15 mg, 0.122 mmol) according to general procedure D. Purification by reverse phase preparative HPLC (Sunfire C18 19×150 mm, 10 μm 20-80%, acetonitrile/water (10 mM $NH_4HCO_3$), 20 mL/min, RT), followed by re-purification (Luna Phenyl-Hexyl 21.2×150 mm, 10 μm 5-60% MeOH/water (0.1% FA), 20 mL/min, RT) gave the formate salt of the title compound. The material was dissolved in MeOH, applied to a MeOH pre-conditioned 2 g Isolute SCX-II cartridge, washed with MeOH, then released with 2 M $NH_3$/MeOH. The 2 M $NH_3$/MeOH eluent was concentrated and dried under vacuum to give the title compound (23 mg, 33%).

$^1$H NMR (400 MHz, DMSO-d6) δ 10.30 (s, 1H), 8.18 (s, 2H), 8.11-8.08 (m, 2H), 7.92 (s, 1H), 7.32 (s, 1H), 6.56 (s, 2H), 3.69 (d, J=13.7 Hz, 1H), 3.60-3.53 (m, 3H), 3.49 (s, 2H), 2.88-2.84 (m, 2H), 2.72-2.64 (m, 4H), 2.62-2.56 (m, 1H), 2.46-2.43 (m, 1H), 2.29 (dd, J=5.7, 7.7 Hz, 1H), 2.07 (s, 6H), 1.91-1.81 (m, 1H), 1.66-1.57 (m, 1H).

LC-MS (ESI): m/z (M+1)=560.1; $t_R$=3.91 min. Method 10

The following compounds were prepared via reductive amination as described for Example 50, step 1-3, applying the previously synthesized or commercially available aryl aldehyde in step 3. Such procedures may involve minor variations. In some cases, where modification involved reductive agents (e.g. $NaBH_3CN$ instead of STAB) or chromatographic purification conditions, such changes were reported in the table.

| Example No | Structure | Reagents Amount | Product Amount (yield) | Purification | Data |
|---|---|---|---|---|---|
| 51 | 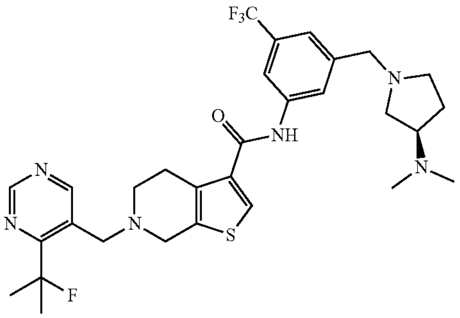 [SMILES: CN(C)[C@@H]1CCN(Cc2cc(NC(=O)c3csc4c3CCN(Cc3cncnc3C(C)(C)F)C4)cc(C(F)(F)F)c2)C1] | General procedure D Intermediate 46: 40 mg, 0.088 mmol (1 eq) 4-(2-fluoropropan-2-yl)pyrimidine-5-carbaldehyde: 26 mg, 0.088 mmol (1 eq) | 25 mg (45%) | prepHPLC | $^1$H NMR (400 MHz, DMSO-d6) δ 10.33 (s, 1H), 9.10 (d, J = 1.4 Hz, 1H), 8.94 (s, 1H), 8.14 (s, 1H), 8.11 (s, 1H), 7.94 (s, 1H), 7.33 (s, 1H), 3.96 (d, J = 2.4 Hz, 2H), 3.74-3.68 (m, 3H), 3.57 (d, J = 13.7 Hz, 1H), 2.93-2.87 (m, 2H), 2.80-2.76 (m, 2H), 2.74-2.67 (m, 2H), 2.64-2.58 (m, 1H), 2.49-2.44 (m, 1H), 2.31 (dd, J = 5.5, 7.7 Hz, 1H), 2.09 (s, 6H), 1.93-1.83 (m, 1H), 1.75 (d, J = 22.0 Hz, 6H), 1.68-1.60 (m, 1H). LC-MS (ESI): Method 9 $t_R$ = 2.59 min; m/z (M + 1) = 605.4 |
| 52 | 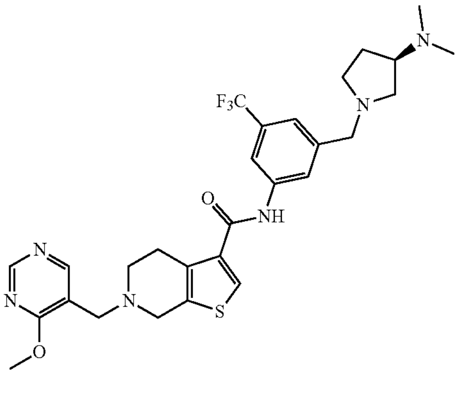 [SMILES: COc1ncncc1CN1CCc2c(C(=O)Nc3cc(CN4CC[C@@H](N(C)C)C4)cc(C(F)(F)F)c3)csc2C1] | General procedure D Intermediate 46: 40 mg, 0.088 mmol (1 eq) 4-methoxypyrimidine-5-carbaldehyde: 12 mg, 0.088 mmol (1 eq) | 22 mg (43%) | prepHPLC | $^1$H NMR (400 MHz, DMSO-d6) δ 10.33 (s, 1H), 8.75 (s, 1H), 8.52 (s, 1H), 8.14-8.10 (m, 2H), 7.94 (s, 1H), 7.33 (s, 1H), 3.98 (s, 3H), 3.73-3.68 (m, 5H), 3.57 (d, J = 13.6 Hz, 1H), 2.93-2.87 (m, 2H), 2.80-2.75 (m, 2H), 2.74-2.67 (m, 2H), 2.64-2.58 (m, 1H), 2.49-2.44 (m, 1H), 2.31 (dd, J = 5.7, 7.8 Hz, 1H), 2.09 (s, 6H), 1.92-1.83 (m, 1H), 1.68-1.59 (m, 1H). LC-MS (ESI): Method 9 $t_R$ = 2.23 min; m/z (M + 1) = 575.4 |

-continued

| Example No | Structure | Reagents Amount | Product Amount (yield) | Purification | Data |
|---|---|---|---|---|---|
| 53 | 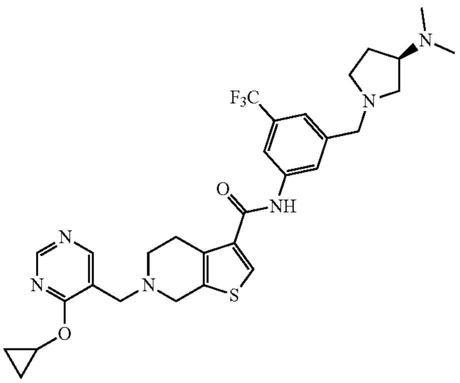 [SMILES: CN(C)[C@@H]1CCN(Cc2cc(NC(=O)c3csc4c3CCN(Cc3cncnc3OC3CC3)C4)cc(C(F)(F)F)c2)C1] | General procedure D Intermediate 46: 70 mg, 0.15 mmol (1 eq) Intermediate 32: 50 mg, 0.30 mmol (2 eq) | 9.8 mg (10%) | prepHPLC | $^1$H NMR (400 MHz, DMSO-d6) δ 10.33 (s, 1H), 8.77 (s, 1H), 8.53 (s, 1H), 8.14-8.10 (m, 2H), 7.94 (s, 1H), 7.33 (s, 1H), 4.45-4.39 (m, 1H), 3.73-3.67 (m, 3H), 3.63 (s, 2H), 3.57 (d, J = 13.8 Hz, 1H), 2.91-2.86 (m, 2H), 2.76-2.67 (m, 4H), 2.64-2.57 (m, 1H), 2.49-2.44 (m, 1H), 2.31 (dd, J = 5.6, 7.7 Hz, 1H), 2.09 (s, 6H), 1.92-1.83 (m, 1H), 1.68-1.59 (m, 1H), 0.86-0.72 (m, 4H). LC-MS (ESI): Method 9 $t_R$ = 2.29 min; m/z (M + 1) = 601.5 |
| 54 | 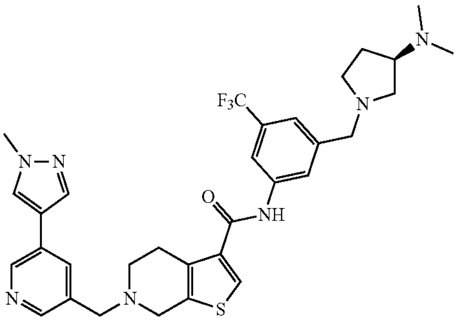 | General procedure C Intermediate 46: 83 mg, 0.183 mmol (1 eq) 5-(1-methylpyrazol-4-yl)pyridine-3-carbaldehyde: 34 mg, 0.183 mmol (1 eq) | 39 mg (34%) | prepHPLC | $^1$H NMR (400 MHz, DMSO-d6) δ 10.32 (s, 1H), 8.76 (d, J = 2.3 Hz, 1H), 8.38 (d, J = 1.9 Hz, 1H), 8.29 (s, 1H), 8.14 (s, 1H), 8.12 (s, 1H), 7.99 (s, 1H), 7.95-7.91 (m, 2H), 7.33 (s, 1H), 3.89 (s, 3H), 3.76 (s, 2H), 3.69 (s, 2H), 2.90 (t, J = 5.1 Hz, 2H), 2.77 (t, J = 5.8 Hz, 2H), 2.73-2.55 (m, 3H), 2.49-2.43 (m, 1H), 2.35-2.29 (m, 1H), 2.09 (s, 6H), 1.92-1.83 (m, 1H), 1.68-1.59 (m, 1H). CH2 peak under DMSO peak. LC-MS (ESI): Method 9 $t_R$ = 2.16 min; m/z (M + 1) = 624.2 |

The following compounds were prepared via reductive amination as described for Example 50, step 1-3, applying the previously synthesized or commercially available aryl amine in step 1.

| Example No | Structure | Step 1 Amount reagents | Step 1 Amount (yield) | Step 3 Finale product Amount (yield) | Purification | Data |
|---|---|---|---|---|---|---|
| 55 | 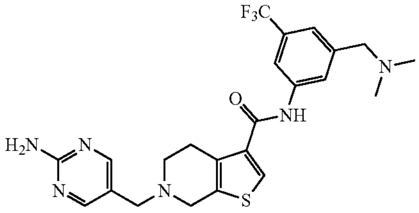 [SMILES: CN(C)Cc1cc(NC(=O)c2csc3c2CCN(Cc2cnc(N)nc2)C3)cc(C(F)(F)F)c1] | General procedure G 6-(tert-butoxycarbonyl)-4,5,6,7-tetrahydrothieno[2,3-c]pyridine-3-carboxylic acid: 223 mg, 0.788 mmol (1 eq) Intermediate 30: 172 mg, 0.788 mmol (1 eq) | 313 mg 82% | 25 mg 38% | prepHPLC | $^1$H NMR (400 MHz, DMSO-d6) δ 10.31 (s, 1H), 8.20 (s, 2H), 8.14-8.10 (m, 2H), 7.97 (s, 1H), 7.33 (s, 1H), 6.59 (s, 2H), 3.61 (s, 2H), 3.51 (s, 2H), 3.47 (s, 2H), 2.90-2.85 (m, 2H), 2.74-2.68 (m, 2H), 2.19 (s, 6H). LC-MS (ESI): Method 9 $t_R$ = 2.21 min; m/z (M + 1) = 491.3 |

-continued

| Example No | Structure | Step 1 Amount reagents | Step 1 Amount (yield) | Step 3 Finale product Amount (yield) | Purification | Data |
|---|---|---|---|---|---|---|
| 56 | 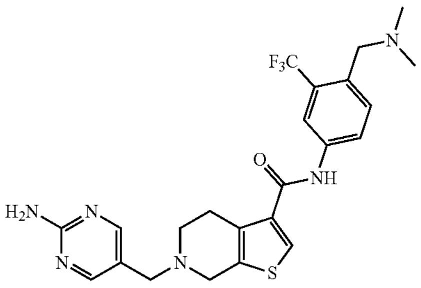 [SMILES: CN(C)Cc1ccc(NC(=O)c2csc3c2CCN(Cc2cnc(N)nc2)C3)cc1C(F)(F)F] | General procedure G 6-(tert-butoxycarbonyl)-4,5,6,7-tetrahydrothieno[2,3-c]pyridine-3-carboxylic acid: 96 mg, 0.339 mmol (1 eq) Intermediate 31: 74 mg, 0.339 mmol (1 eq) | 121 mg 73% | 27 mg (52%) | prepHPLC | $^1$H NMR (400 MHz, DMSO-d6) δ 10.30 (s, 1H), 8.20 (s, 2H), 8.15 (d, J = 2.2 Hz, 1H), 8.09 (s, 1H), 7.98 (dd, J = 1.8, 8.6 Hz, 1H), 7.69 (d, J = 8.5 Hz, 1H), 6.58 (s, 2H), 3.61 (s, 2H), 3.52-3.48 (m, 4H), 2.88-2.84 (m, 2H), 2.73-2.68 (m, 2H), 2.19 (s, 6H) LC-MS (ESI): Method 9 $t_R$ = 2.04 min; m/z (M + 1) = 491.3 |
| 57 | 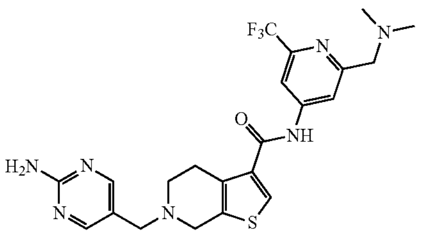 [SMILES: CN(C)Cc1cc(NC(=O)c2csc3c2CCN(Cc2cnc(N)nc2)C3)cc(C(F)(F)F)n1] | General procedure G 6-(tert-butoxycarbonyl)-4,5,6,7-tetrahydrothieno[2,3-c]pyridine-3-carboxylic acid: 96 mg, 0.339 mmol (1 eq) Intermediate 35: 115 mg, 0.525 mmol | 70 mg 27% | 7 mg (17%) | prepHPLC | $^1$H NMR (400 MHz, DMSO-d6) δ 10.68 (s, 1H), 8.23 (s, 1H), 8.20 (s, 2H), 8.18 (d, J = 1.9 Hz, 1H), 8.10 (d, J = 1.4 Hz, 1H), 6.59 (s, 2H), 3.62 (s, 2H), 3.57 (s, 2H), 3.51 (s, 2H), 2.91-2.86 (m, 2H), 2.74-2.69 (m, 2H), 2.24 (s, 6H) LC-MS (ESI): Method 9 $t_R$ = 2.12 min; m/z (M + 1) = 492.3 |

Example 58: preparation of 6-((2-aminopyrimidin-5-yl)methyl)-N-(3-(1,1-difluoroethyl)phenyl)-4,5,6,7-tetrahydrothieno[2,3-c]pyridine-3-carboxamide

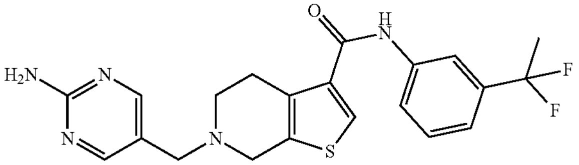 [SMILES: CC(F)(F)c1cccc(NC(=O)c2csc3c2CCN(Cc2cnc(N)nc2)C3)c1]

Example 58

Step 1: preparation of tert-butyl 3-((3-(1,1-difluoroethyl)phenyl)carbamoyl)-4,7-dihydrothieno[2,3-c]pyridine-6(5H)-carboxylate (Intermediate 47)

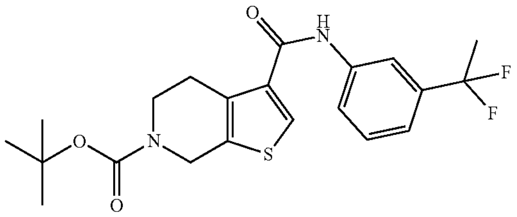 [SMILES: CC(C)(C)OC(=O)N1CCc2c(C(=O)Nc3cccc(C(C)(F)F)c3)csc2C1]

Prepared from 6-(tert-butoxycarbonyl)-4,5,6,7-tetrahydrothieno[2,3-c]pyridine-3-carboxylic acid (500 mg, 1.76 mmol, 1.0 eq) and was added 3-(1,1-difluoroethyl)aniline (291 mg, 1.85 mmol, 1.05 eq) according to general procedure G. The combined organic phases were dried over $MgSO_4$, filtered, concentrated and dried under vacuum overnight to afford the title compound (1140 mg, 1.78 mmol, 101%).

$^1$H NMR (400 MHz, $CDCl_3$) δ 7.91 (s, 1H), 7.77-7.67 (m, 2H), 7.65 (s, 1H), 7.41 (t, J=8.0 Hz, 1H), 7.28 (s, 1H), 4.62 (s, 2H), 3.67 (t, J=5.3 Hz, 2H), 3.00-2.96 (m, 2H), 1.93 (t, J=18.2 Hz, 3H), 1.49 (s, 9H).

Step 2: preparation of N-(3-(1,1-difluoroethyl)phenyl)-4,5,6,7-tetrahydrothieno[2,3-c]pyridine-3-carboxamide (Intermediate 48)

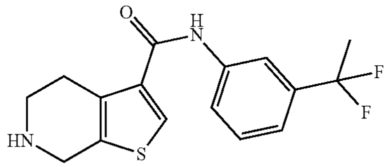 [SMILES: CC(F)(F)c1cccc(NC(=O)c2csc3c2CCNC3)c1]

To a solution of Intermediate 47 (750 mg, 1.17 mmol, 1.00 eq) in 1,4-dioxane (10 mL) was added 4N HCl in 1,4-dioxane (10 mL). The reaction mixture was stirred at room temperature overnight. Reaction quenched with $Et_2O$ and filtered, the solid obtained was washed with $Et_2O$ and dried under vacuum. Obtained the tile compound (684 mg, 1.72 mmol, 146%). The material was taken on to the next step without further purification.

$^1$H NMR (400 MHz, DMSO-d6) δ 10.47 (s, 1H), 8.44 (s, 1H), 8.06 (s, 1H), 7.92 (d, J=7.8 Hz, 1H), 7.73 (m, 1H), 7.51 (t, J=8.0 Hz, 1H), 7.33 (d, J=7.3 Hz, 1H), 4.42 (s, 2H), 3.40 (m, 2H), 3.16 (t, J=5.7 Hz, 2H), 2.01 (t, J=18.8 Hz, 3H).

Step 3: preparation of 6-((2-aminopyrimidin-5-yl) methyl)-N-(3-(1,1-difluoroethyl)phenyl)-4,5,6,7-tetrahydrothieno[2,3-c]pyridine-3-carboxamide Example 58

Prepared from Intermediate 48 (90%, 60 mg, 0.150 mmol, 1.00 eq) and 2-Aminopyrimidine-5-carboxaldehyde (19 mg, 0.150 mmol, 1.00 eq) according to general procedure C. The residue was washed with DCM/MeOH, combined washings evaporated and the residue dried under vacuum. The residue was submitted for purification by preparative HPLC. Sunfire C18 19×150 mm, 10 um 5-60% ACN/$H_2O$ (0.1% FA), 20 ml/min, RT. Obtained the title compound (20.47 mg, 0.0469 mmol, 31.3% yield).

$^1$H NMR (400 MHz, DMSO) δ 10.20 (s, 1H), 8.20 (s, 2H), 8.08 (s, 1H), 7.99 (t, J=2.1 Hz, 1H), 7.84 (d, J=8.2 Hz, 1H), 7.46 (t J=8.0 Hz, 1H), 7.27 (d, J=8.0 Hz, 1H), 6.58 (s, 2H), 3.61 (s, 2H), 3.51 (s, 2H), 2.88 (t, J=5.4 Hz, 2H), 2.74-2.68 (m, 2H), 1.97 (t, J=18.8 Hz, 3H). LC-MS (ESI): m/z (M+1)=430.6; $t_R$=4.02 min. Method 8 The following compounds were prepared via reductive amination as described for Example 58, step 1-3, applying the previously synthesized or commercially available aryl amine in step 1.

Example 61

Step 1. Preparation of tert-butyl 3-((4-chloro-3-(trifluoromethyl)phenyl)carbamoyl)-4,7-dihydrothieno[2,3-c]pyridine-6(5H)-carboxylate (Intermediate 49)

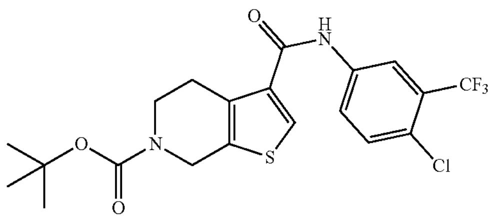

| Example No | Structure | Step 1 Reagents Amount | Step 1 Amount (yield) | Step 3 Final product Amount (yield) | Purification | Data |
|---|---|---|---|---|---|---|
| 59 | 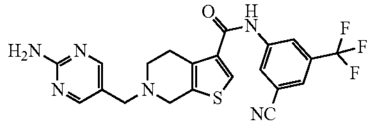 [SMILES: N#Cc1cc(NC(=O)c2csc3c2CCN(Cc2cnc(N)nc2)C3)cc(C(F)(F)F)c1] | General procedure G 6-(tert-butoxycarbonyl)-4,5,6,7-tetrahydrothieno[2,3-c]pyridine-3-carboxylic acid: 500 mg, 1.76 mmol (1 eq) 3-amino-5-(trifluoromethyl)benzonitrile (345 mg, 1.85 mmol (1.05 eq) | 704 mg, 1.56 mmol, 88% | 23 mg, 0.0449 mmol, 35% | prepHPLC | $^1$H NMR (400 MHz, DMSO-d6) δ 10.62 (s, 1H), 8.42 (d, J = 7.9 Hz, 2H), 8.20 (s, 2H), 8.16 (s, 1H), 8.05 (s, 1H), 6.58 (s, 2H), 3.61 (s, 2H), 3.51 (s, 2H), 2.89 (t, J = 5.6 Hz, 2H), 2.72 (t, J = 5.7 Hz, 2H). LC-MS (ESI): Method 11 $t_R$ = 3.21 min; m/z (M + 1) = 459.6 |
| 60 | 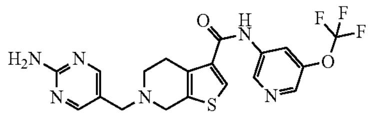 [SMILES: Nc1ncc(CN2CCc3c(C(=O)Nc4cncc(OC(F)(F)F)c4)csc3C2)cn1] | General procedure G 6-(tert-butoxycarbonyl)-4,5,6,7-tetrahydrothieno[2,3-c]pyridine-3-carboxylic acid: 85 mg, 0.298 mmol, (1.0 eq) Intermediate 38, 64 mg, 0.298 mmol, (1.0 eq) | 100 mg, 0.226 mmol, 76% | 5.6 mg, 0.0119 mmol, 11% | prepHPLC | $^1$H NMR (400 MHz, DMSO-d6) δ 10.56 (s, 1H), 8.90 (d, J = 2.0 Hz, 1H), 8.40 (d, J = 2.5 Hz, 1H), 8.33 (s, 1H), 8.20 (s, 2H), 8.15 (s, 1H), 6.58 (s, 2H), 3.61 (s, 2H), 3.51 (s, 2H), 2.87 (t, J = 5.5 Hz, 2H), 2.74-2.68 (m, 2H). LC-MS (ESI): Method 9 $t_R$ = 2.83 min; m/z (M + 1) = 451.4 |

Example 61: preparation of 6-((2-aminopyrimidin-5-yl)methyl)-N-(4-chloro-3-(trifluoromethyl)phenyl)-4,5,6,7-tetrahydrothieno[2,3-c]pyridine-3-carboxamide

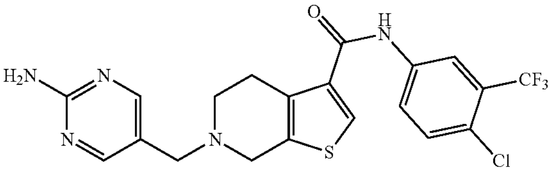 [SMILES: Nc1ncc(CN2CCc3c(C(=O)Nc4ccc(Cl)c(C(F)(F)F)c4)csc3C2)cn1]

Prepared from 6-(tert-butoxycarbonyl)-4,5,6,7-tetrahydrothieno[2,3-c]pyridine-3-carboxylic acid (250 mg, 0.882 mmol, 1.0 eq) and was added 4-Chloro-3-(trifluoromethyl) aniline (181 mg, 0.926 mmol, 1.05 eq) according to general procedure G. The reaction mixture was stirred at room temperature for 90 min, quenched with water stirred for 30 min and filtered. The solid was washed with water and dried under vacuum. Obtained title compound (360 mg, 0.781 mmol, 89%). The material was taken on to the next step without further purification.

$^1$H NMR (400 MHz, $CDCl_3$) δ 7.93 (s, 2H), 7.86-7.82 (m, 1H), 7.64 (s, 1H), 7.48 (d, J=8.8 Hz, 1H), 4.61 (s, 2H), 3.68 (t, J=5.3 Hz, 2H), 2.99 (t, J=5.7 Hz, 2H), 1.57 (s, 4H), 1.50 (s, 9H).

Step 2: preparation of N-(4-chloro-3-(trifluoromethyl)phenyl)-4,5,6,7-tetrahydrothieno[2,3-c]pyridine-3-carboxamide (Intermediate 50)

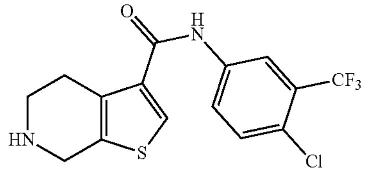 [SMILES: O=C(Nc1ccc(Cl)c(C(F)(F)F)c1)c1csc2c1CCNC2]

To a solution of Intermediate 49 (360 mg, 0.781 mmol, 1.00 eq) in 1,4-dioxane (3 mL) was added 4N HCl in 1,4-dioxane (3.0 mL). The reaction mixture was stirred at room temperature for 18 hrs. Reaction quenched with $Et_2O$ and filtered, solid washed with $Et_2O$ and dried under vacuum to give the title compound as hydrochloride salt (289 mg, 0.666 mmol, 85%).

$^1H$ NMR (400 MHz, DMSO-d6) δ 10.76 (s, 1H), 9.66-9.57 (m, 2H), 8.49 (s, 1H), 8.42 (d, J=2.5 Hz, 1H), 8.14 (dd, J=2.3, 8.8 Hz, 1H), 7.75 (d, J=8.8 Hz, 1H), 4.43 (s, 2H), 3.16 (t, J=5.8 Hz, 2H)—

Step. 3: preparation of 6-((2-aminopyrimidin-5-yl)methyl)-N-(4-chloro-3-(trifluoromethyl)phenyl)-4,5,6,7-tetrahydrothieno[2,3-c]pyridine-3-carboxamide Example 61

It was prepared from Intermediate 49 (60 mg, 0.151 mmol, 1.00 eq) and 2-Aminopyrimidine-5-carboxaldehyde (27 mg, 0.223 mmol, 1.47 eq) according to general procedure H. The crude was purified by preparative HPLC (Luna Phenyl-Hexyl 21.2×150 mm, 10 um 20-80% $MeOH/H_2O$ (0.1% FA), 20 ml/min, RT) to afford the title compound (17 mg, 0.0352 mmol, 23%)

$^1H$ NMR (400 MHz, DMSO-d6) δ 10.44 (s, 1H), 8.32 (d, J=2.3 Hz, 1H), 8.19 (s, 2H), 8.12 (s, 1H), 8.04 (dd, J=2.4, 8.8 Hz, 1H), 7.70 (d, J=8.7 Hz, 1H), 6.58 (s, 2H), 3.61 (s, 2H), 3.51 (s, 2H), 2.87 (d, J=5.0 Hz, 2H), 2.71 (t, J=5.8 Hz, 2H). LC-MS (ESI): m/z (M+1)=468.4; $t_R$=4.57 min. Method 8

Example 62: preparation of 6-((2-aminopyrimidin-5-yl)methyl)-N-(5-(1,1,1-trifluoro-2-methylpropan-2-yl)isoxazol-3-yl)-4,5,6,7-tetrahydrothieno[2,3-c]pyridine-3-carboxamide

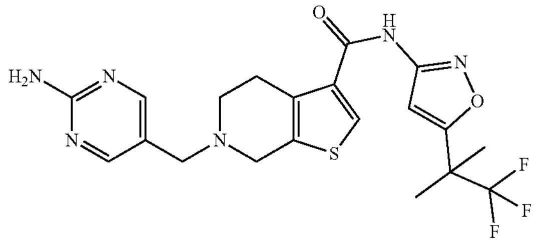 [SMILES: CC(C)(c1cc(NC(=O)c2csc3c2CCN(Cc2cnc(N)nc2)C3)no1)C(F)(F)F]

Example 62

Step 1: preparation of tert-butyl 3-((5-(1,1,1-trifluoro-2-methylpropan-2-yl)isoxazol-3-yl)carbamoyl)-4,7-dihydrothieno[2,3-c]pyridine-6(5H)-carboxylate (Intermediate 51)

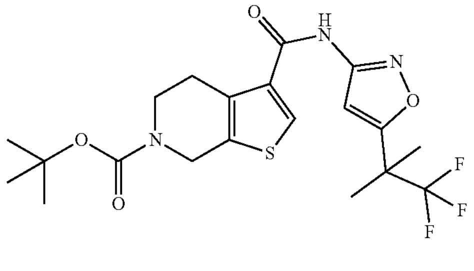 [SMILES: CC(C)(C)OC(=O)N1CCc2c(C(=O)Nc3cc(C(C)(C)C(F)(F)F)on3)csc2C1]

To a solution of 6-tert-butoxycarbonyl-5,7-dihydro-4H-thieno[2,3-c]pyridine-3-carboxylic acid (250 mg, 0.882 mmol, 1.00 eq) and DMF (0.0034 mL, 0.0441 mmol, 0.05 eq) in cyclopentyl methyl ether (2 mL) at 20° C. Oxalyl chloride (0.088 mL, 1.06 mmol, 1.20 eq) was added dropwise. The reaction mixture was stirred at room temperature for 2 hours. The reaction mixture was concentrated under vacuum and the residue azeotroped with cyclopentyl methyl ether, the residue was suspended in ACN (1 mL) and cooled to 0° C. in an ice bath, to the mixture was added 5-(2,2,2-trifluoro-1,1-dimethyl-ethyl)isoxazol-3-amine (171 mg, 0.882 mmol, 1.00 eq) and Pyridine (0.14 mL, 1.76 mmol, 2.00 eq) in ACN (1 mL). The reaction mixture was allowed to warm to room temperature and stirred for 45 min. The reaction mixture was concentrated under vacuum.

The residue was partitioned between DCM and water. The combined organic phases were filtered through a hydrophobic frit and the solvent was concentrated under vacuum. The residue was purified by silica FCC (eluting with 0-100% EtOAc in Cyclohexane) to yield title compound (255 mg, 0.555 mmol, 63%) The material was taken on to the next step without further purification.

$^1H$ NMR (400 MHz, $CDCl_3$) δ 9.65 (s, 1H), 7.91 (s, 1H), 7.13 (s, 1H), 4.64 (s, 2H), 3.68 (t, J=5.4 Hz, 2H), 3.01 (t, J=5.8 Hz, 2H), 1.60 (s, 6H), 1.49 (s, 9H).

Step 2: preparation of N-(5-(1,1,1-trifluoro-2-methylpropan-2-yl)isoxazol-3-yl)-4,5,6,7-tetrahydrothieno[2,3-c]pyridine-3-carboxamide (Intermediate 52)

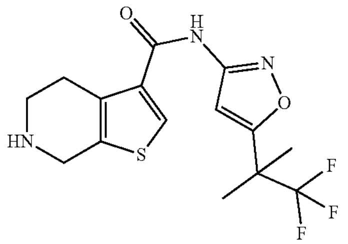 [SMILES: CC(C)(c1cc(NC(=O)c2csc3c2CCNC3)no1)C(F)(F)F]

To a solution of Intermediate 51 (255 mg, 0.555 mmol, 1.00 eq) in 1,4-dioxane (3 mL) at 0° C. was added 4N HCl in 1,4-dioxane (3.0 mL, 0.555 mmol, 1.00 eq). The reaction mixture was allowed to warm to room temperature and stirred at room temperature over the weekend. Reaction diluted with $Et_2O$ (20 mL) and filtered, solid washed with $Et_2O$ and dried under vacuum to obtained the title compound (190 mg, 0.480 mmol, 86%) as the HCl salt. $^1$H NMR (400 MHz, DMSO-d6) δ 11.49 (s, 1H), 9.64-9.55 (m, 2H), 8.52 (s, 1H), 7.11 (s, 1H), 4.42 (s, 2H), 3.15 (t, J=5.6 Hz, 2H), 1.63 (s, 6H).

Step 3: preparation of 6-((2-aminopyrimidin-5-yl) methyl)-N-(5-(1,1,1-trifluoro-2-methylpropan-2-yl) isoxazol-3-yl)-4,5,6,7-tetrahydrothieno[2,3-c]pyridine-3-carboxamide (Example 62)

To a solution of 2-Aminopyrimidine-5-carboxaldehyde (16 mg, 0.126 mmol, 1.00 eq), Intermediate 52 (50 mg, 0.126 mmol, 1.00 eq) and DMF (0.044 mL, 0.253 mmol, 2.00 eq) in MeOH (3.00 mL), Titanium(IV) isopropoxide (0.11 mL, 0.379 mmol, 3.00 eq) was added. The reaction mixture was heated at reflux for 2 hrs. The reaction mixture was allowed to cool to room temperature and $NaBH_3CN$ (20 mg, 0.316 mmol, 2.50 eq) was added. The reaction mixture was stirred at room temperature for 18 hrs. Reaction quenched with water (30 mL) and filtered through celite. The residue was washed with DCM/MeOH, combined washings evaporated and the residue dried under vacuum over $P_2O_5$. The residue was submitted for purification by preparative HPLC. Sunfire C18 19×150 mm, 10 um 5-60% $ACN/H_2O$ (0.1% FA), 20 ml/min, RT. Obtained title compound (17 mg, 0.0343 mmol, 27%)

$^1$H NMR (400 MHz, DMSO-d6) δ 11.27 (s, 1H), 8.29 (s, 1H), 8.19 (s, 2H), 7.08 (s, 1H), 6.58 (s, 2H), 3.60 (s, 2H), 3.50 (s, 2H), 2.87 (m, 2H), 2.71-2.67 (m, 2H), 1.59 (s, 6H). LC-MS (ESI): m/z (M+1)=467.7; $t_R$=3.17 min. Method 11

The following compounds were prepared via reductive amination as described for Example 62, step 1-3, applying the commercially available heteroaryl amine in step 1.

Example 65: preparation of N-(3-(tert-butyl)isoxazol-5-yl)-6-((5-methoxypyridin-3-yl)-4,5,6,7-tetrahydrothieno[2,3-c]pyridine-3-carboxamide

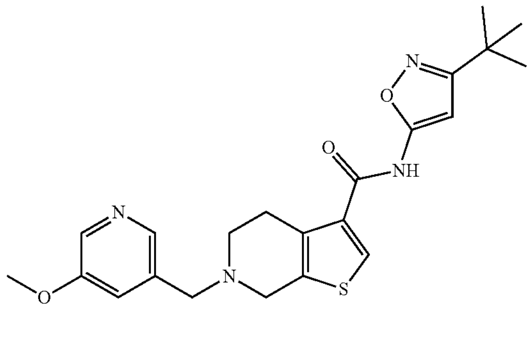 [SMILES: COc1cncc(CN2CCc3c(C(=O)Nc4cc(C(C)(C)C)no4)csc3C2)c1]

Example 65

Step 1: preparation of Ethyl (6-((5-methoxypyridin-3-yl)methyl)-4,5,6,7-tetrahydrothieno[2,3-c]pyridine-3-carboxylate (Intermediate 53)

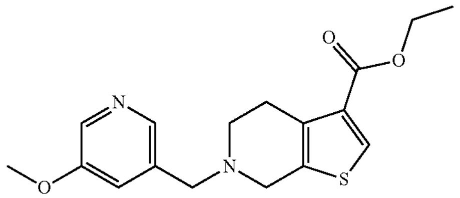 [SMILES: CCOC(=O)c1csc2c1CCN(Cc1cncc(OC)c1)C2]

| Example No | Structure | Step 1 Reagents Amount | Step 1 Amount (yield) | Step 3 Final product Amount (yield) | Purification | Data |
|---|---|---|---|---|---|---|
| 63 | 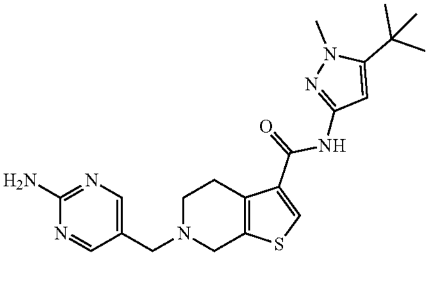 | 6-(tert-butoxycarbonyl)-4,5,6,7-tetrahydrothieno[2,3-c]pyridine-3-carboxylic acid: 142 mg, 0.50 mmol (1.0 eq) 3-Amino-5-tert-butylisoxazole: 70 mg, 0.500 mmol (1.0 eq) | 164 mg, 0.404 mmol, 81% | 11 mg, 0.027 mmol 19%, | prepHPLC | $^1$H NMR (400 MHz, DMSO-d6) δ 10.43 (s, 1H), 8.19 (s, 2H), 8.12 (s, 1H), 6.58 (s, 2H), 6.41 (s, 1H), 3.83 (s, 3H), 3.58 (s, 2H), 3.49 (s, 2H), 2.85 (t, J = 5.3 Hz, 2H), 2.68 (t, J = 5.6 Hz, 2H), 1.35 (s, 9H). LC-MS (ESI): Method 9 $t_R$ = 2.79 min; m/z (M + 1) = 426.4 |
| 64 | 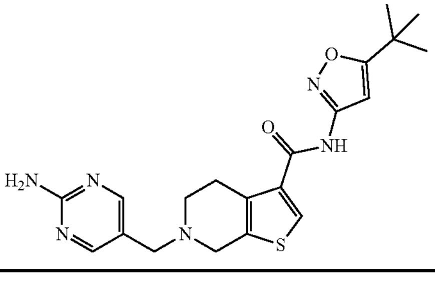 | 6-(tert-butoxycarbonyl)-4,5,6,7-tetrahydrothieno[2,3-c]pyridine-3-carboxylic acid: 142 mg, 0.50 mmol (1.0 eq) 5-tert-butyl-1-methyl-pyrazol-3-amine: 77 mg, 0.500 mmol (1.0 eq) | 161 mg, 0.358 mmol, 72% | 12 mg, 0.028 mmol 19%) | prepHPLC | $^1$H NMR (400 MHz, DMSO-d6) δ 11.10 (s, 1H), 8.26 (s, 1H), 8.19 (s, 2H), 6.70 (s, 1H), 6.58 (s, 2H), 3.59 (s, 2H), 3.50 (s, 2H), 2.86 (t, J = 5.5 Hz, 2H), 2.69 (t, J = 5.8 Hz, 2H), 1.33 (s, 9H). LC-MS (ESI): Method 9 $t_R$ = 3.01 min; m/z (M + 1) = 413.5 |

Prepared from 5-methoxy-3-pyridinecarboxaldehyde (91 mg, 0.666 mmol) and Intermediate 6 (150 mg, 0.605 mmol) according to general procedure F. Purification was performed by silica FCC (25 g), eluting with 2M methanolic ammonia in DCM (15:1) % in DCM (0 to 100%) gave the title compound (190 mg, 94%)

$^1$H NMR (400 MHz, $CDCl_3$) δ 8.25-8.23 (m, 1H), 8.18 (d, J=1.2 Hz, 1H), 7.95-7.94 (m, 1H), 7.28 (t, J=2.3 Hz, 1H), 4.29 (q, J=7.1 Hz, 2H), 3.86-3.86 (m, 3H), 3.72-3.66 (m, 4H), 3.03-2.98 (m, 2H), 2.83-2.79 (m, 2H), 1.35 (t, J=7.1 Hz, 3H)

Step 2: preparation of (6-((5-Methoxypyridin-3-yl) methyl)-4,5,6,7-tetrahydrothieno[2,3-c]pyridine-3-carboxylic acid (Intermediate 54)

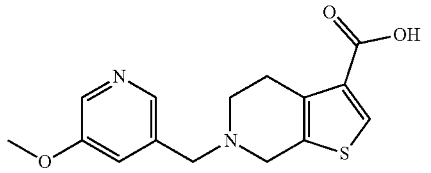 [SMILES: COc1cncc(CN2CCc3c(C(=O)O)csc3C2)c1]

NaOH (81 mg, 2.03 mmol, 3.10 eq) was added to a solution of Intermediate 53 (217 mg, 0.653 mmol, 1.00 eq) in MeOH (10 mL) and water (0.5 mL) and the mixture stirred at 50° C. for 18 h. The mixture was cooled in an ice bath and 1M HCl (1.8 mL, 1.78 mmol, 2.73 eq) was added dropwise. The solution was concentrated under vacuum resulting in solid precipitation, which was filtered off, washed with acetone (2 mL) to give the title compound (166 mg, 83%). LC-MS (ESI): m/z (M+1)=305.2; $t_R$=0.68 min. Method 12

Step 3: Preparation of N-(3-(tert-butyl)isoxazol-5-yl)-6-((5-methoxypyridin-3-yl)-4,5,6,7-tetrahydrothieno[2,3-c]pyridine-3-carboxamide (Example 65)

Intermediate 54 (30 mg, 0.0986 mmol) was suspended in thionyl chloride (0.21 mL, 2.93 mmol) and the reaction mixture was stirred at 50° C. for 2 h. The reaction mixture was allowed to cool to room temperature and concentrated under vacuum. The residue was suspended in toluene and re-concentrated to give the intermediate acyl chloride. To a solution of the 3-tert-butylisoxazol-5-amine (21 mg, 0.148 mmol) and DMAP (2.4 mg, 0.020 mmol) in pyridine (0.1M concentration), was added the acyl chloride followed by DIPEA (51.5 μL, 0.296 mmol). The reaction mixture was stirred at 40° C. until LCMS indicated consumption of starting material and then concentrated under vacuum. The purification was performed by reverse phase preparative HPLC (Luna Phenyl-Hexyl 21.2×150 mm, 10 um 20-80% MeOH/$H_2O$ (0.1% FA), 20 ml/min, RT) to gave the title compound (28 mg, 0.065 mmol, 66%).

$^1$H NMR (400 MHz, DMSO-d6) δ 11.73-11.69 (m, 1H), 8.28 (s, 1H), 8.23 (d, J=3.2 Hz, 1H), 8.16 (d, J=0.9 Hz, 1H), 7.35 (dd, J=1.8, 2.8 Hz, 1H), 6.37 (s, 1H), 3.84 (s, 3H), 3.73 (s, 2H), 3.65 (s, 2H), 2.90 (t, J=5.6 Hz, 2H), 2.76-2.71 (m, 2H), 1.29-1.28 (m, 9H). LC-MS (ESI): m/z (M+1)=427.2; $t_R$=3.14 min. Method 9

Comparative newly synthesised compounds characterized by alternatively:

- the absence of a linker between the tetrahydrothieno pyridine ring and the Hy group (Example C1) and
- both the absence of a linker between the tetrahydrothieno pyridine ring and the Hy group, and the —C(O)NH— group substituting the thienyl ring at the α position with respect to the sulphur atom (Example C2)

Example C1; Preparation of N-(3-((4-methylpiperazin-1-yl)methyl)-5-(trifluoromethyl)phenyl)-6-(pyrimidin-5-yl)-4,5,6,7-tetrahydrothieno[2,3-c]pyridine-3-carboxamide

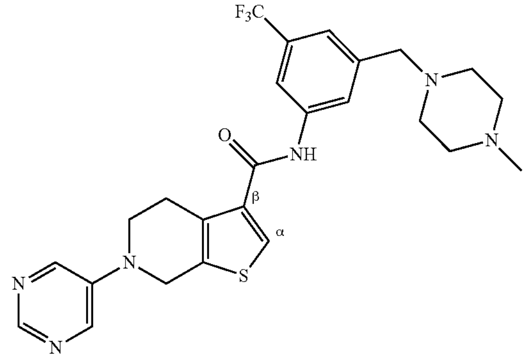 [SMILES: CN1CCN(Cc2cc(NC(=O)c3csc4c3CCN(c3cncnc3)C4)cc(C(F)(F)F)c2)CC1]

Example C1

Step 1; ethyl 6-(pyrimidin-5-yl)-4,5,6,7-tetrahydrothieno[2,3-c]pyridine-3-carboxylate (Intermediate 16)

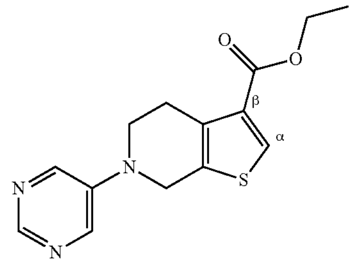 [SMILES: CCOC(=O)c1csc2c1CCN(c1cncnc1)C2]

A 20 mL vial, equipped with a magnetic stir bar and fitted with a seal cap, was charged with Intermediate 6 (163.1 mg, 0.658 mmol), 5-bromopyrimidine (0.105 ml, 0.658 mmol), $Cs_2CO_3$ (0.215 ml, 0.658 mmol), $Pd(dba)_2$ (0.379 ml, 0.658 mmol) and RuPhos (0.307 ml, 0.658 mmol). The vessel vas evacuated and backfilled with Argon, then Toluene (4 ml) was added via syringe. The solution was heated at 120° C. and stirred on. After cooling down to RT, the solution was filtered through a pad of Celite, then concentrated to dryness. The crude was purified by FCC (column silica-NH gradient n-Heptane/Acetone from 100:0 to 60:40) to provide the title compound (100 mg, 0.346 mmol, 52.5% yield).

$^1$H NMR (400 MHz, $CDCl_3$) δ ppm 8.72 (s, 1H) 8.47 (s, 2H) 8.03 (s, 1H) 4.54 (s, 2H) 4.32 (q, J=7.16 Hz, 2H) 3.70 (t, J=5.81 Hz, 2H) 3.16 (br t, J=5.59 Hz, 2H) 1.38 (t, J=7.13 Hz, 3H)

Step 2; N-(3-((4-methylpiperazin-1-yl)methyl)-5-(trifluoromethyl)phenyl)-6-(pyrimidin-5-yl)-4,5,6,7-tetrahydrothieno[2,3-c]pyridine-3-carboxamide (Example C1)

3-((4-methylpiperazin-1-yl)methyl)-5-(trifluoromethyl) aniline (76 mg, 0.276 mmol) was dissolved in dry THF (Volume: 6 ml, Ratio: 1.500) under Nitrogen the mixture was stirred at −78° C. for 15 min, then n-BuLi (0.105 ml, 0.263 mmol) was added dropwise in 5 min and the solution was stirred for 1 hr at −78° C. A solution of ethyl Intermediate 16 (40 mg, 0.138 mmol) in THF (Volume: 4 ml, Ratio: 1.000) was added dropwise for 10 min, then the temperature was increased at RT and the reaction was stirred for another 1 hr. 10 mL of water was added on the solution and the solvent was evaporated. The product was obtained by flash chromatography in reverse Phase (column C18 Ultra gradient A:B from 100:0 to 0:100 eluent A: $H_2O$:ACN:HCOOH 95:5:0.1 Eluent B:$H_2O$:ACN:HCOOH 5:95:0.1) The relevant fractions were combined and loaded onto an Isolute SCX-2 cartridge, washed with MeOH and the product was eluted with 7N methanolic ammonia. The residue was concentrated under vacuum to afford the title compound (23.5 mg, 0.045 mmol, 32.9% yield).

$^1$H NMR (400 MHz, ACN-d3) 6 ppm 8.74 (br s, 1H), 8.58 (s, 1H), 8.49 (s, 2H), 7.99 (s, 1H), 7.93 (s, 1H), 7.84 (s, 1H), 7.36 (s, 1H), 4.57 (s, 2H), 3.70 (t, J=5.81 Hz, 2H), 3.54 (s, 2H), 2.95-3.13 (m, 2H), 2.30-2.44 (br s, 8H), 2.20 (s, 3H). LC-MS (ESI): m/z (M+1)=517.2; $t_R$=1.03 min (method 1)

Example C2: N-(3-((4-methylpiperazin-1-yl) methyl)-5-trifluoromethyl)phenyl)-5-(pyrimidin-5-yl)-4,5,6,7-tetrahydrothieno[3,2-c]pyridine-2-carboxamide

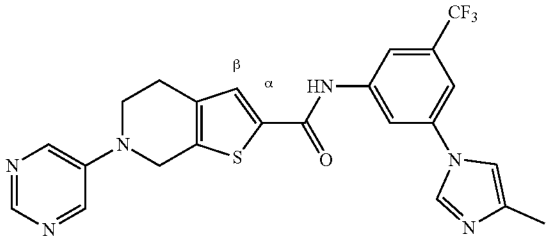 [SMILES: Cc1cn(-c2cc(NC(=O)c3cc4c(s3)CN(c3cncnc3)CC4)cc(C(F)(F)F)c2)cn1]

Example C2

Step 1; 6-(tert-butyl) 2-methyl 4,7-dihydrothieno[2,3-c]pyridine-2,6(5H)-dicarboxylate (Intermediate 17)

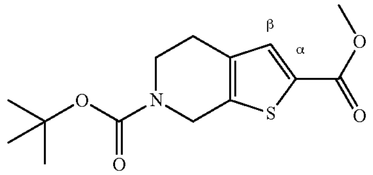 [SMILES: COC(=O)c1cc2c(s1)CN(C(=O)OC(C)(C)C)CC2]

6-(tert-butoxycarbonyl)-4,5,6,7-tetrahydrothieno[2,3-c] pyridine-2-carboxylic acid (200 mg, 0.706 mmol) and $Cs_2CO_3$ (345 mg, 1.059 mmol) were dissolved in anhydrous DMF (Volume: 10 ml) then $CH_3I$ (0.066 ml, 1.059 mmol) was added in one portion. The solution was stirred at room temperature for 3 h. the reaction mixture was diluted with $Et_2O$ (20 mL) then washed with sat $NH_4Cl$ (10 mL) and brine (10 mL). The organic phase was separated, dried over $Na_2SO_4$, filtered and concentrated to dryness to afford the title compound (182 mg, 0.611 mmol, 87% yield).

Step 2; methyl 4,5,6,7-tetrahydrothieno[2,3-c]pyridine-2-carboxylate hydrochloride (Intermediate 18)

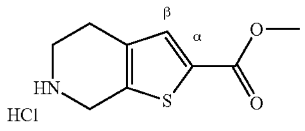

1 mL of concentrated HCl was added in a round bottom flask with Intermediate 17 (181.6 mg, 0.611 mmol). The reaction proceeded with a gas formation and was completed in 5 minutes ad rt. 30 mL of ethanol was added at the mixture and the solvent was evaporated with reduced pressure until obtained the title compound in quantitative yield.

Step 3; methyl 6-(pyrimidin-5-yl)-4,5,6,7-tetrahydrothieno[2,3-c]pyridine-2-carboxylate (Intermediate 19)

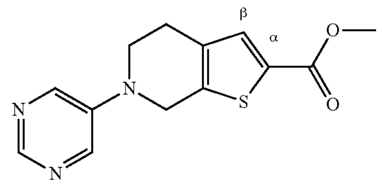 [SMILES: COC(=O)c1cc2c(s1)CN(c1cncnc1)CC2]

A 20 mL microwave vial, equipped with a magnetic stir bar and fitted with a seal cap, was charged with Intermediate 18 (125 mg, 0.535 mmol), 5-bromopyrimidine (111 mg, 0.695 mmol), $Cs_2CO_3$ (523 mg, 1.605 mmol), $Pd(dba)_2$ (30.8 mg, 0.053 mmol) and RuPhos (49.8 mg, 0.107 mmol). The vessel was evacuated and backfilled with Argon, then Toluene (Volume: 5 ml) was added via syringe. The solution was heated at 110° C. and stirred on. After cooling down to r.t., the solution was filtered through a pad of Celite, then concentrated to dryness. The crude was purified by FCC (gradient A:B from 100:0 to 60:40, eluent A:n-Heptane eluent B:Acetone) to afford the title compound (118.5 mg, 0.430 mmol, 80% yield).

$^1$H NMR (acetone, 400 MHz) δ 8.5-8.6 (m, 3H), 7.55 (s, 1H), 4.69 (s, 2H), 3.83 (s, 3H), 3.80 (t, 2H, J=5.8 Hz), 2.89 (t, 2H, J=5.8 Hz)

Step 4; N-(3-((4-methylpiperazin-1-yl)methyl)-5-trifluoromethyl)phenyl)-5-(pyrimidin-5-yl)-4,5,6,7-tetrahydrothieno[3,2-c]pyridine-2-carboxamide (Example C2)

3-(4-methyl-1H-imidazol-1-yl)-5-(trifluoromethyl)aniline (52.4 mg, 0.217 mmol) was dissolved in dry THF (Volume: 4) under Nitrogen and the mixture was stirred at −78° C. for 15 min, then n-BuLi 2.5 M in hexane (0.083 ml, 0.206 mmol) was added dropwise in 5 min and the solution was stirred for 1 hr at −78° C. A solution of methyl Intermediate 19 (29.9 mg, 0.109 mmol) in THF (Volume: 2 ml) was added dropwise for 10 min and the temperature was increased at rt and the reaction was stirred for 1 hr. 10 mL of water was added to quench the reaction, the crude was extracted in AcOEt (2×20 mL), the organic layers was combined and the solvent was evaporated by reduced pressure. The crude product was purified by FCC in reverse Phase (gradient A:B from 100:0 to 0:100. eluent A: $H_2O$: ACN:HCOOH 95:5:0.1 eluent B:$H_2O$:ACN:HCOOH 5:95: 0.1). Appropriate fractions were combined and evaporated to afford the title compound (8.7 mg, 0.018 mmol, 16.53% yield).

$^1H$ NMR (400 MHz, ACETONITRILE-d3) 6 ppm 8.97 (br s, 1H), 8.59 (s, 1H), 8.49 (s, 2H), 8.11 (s, 1H), 8.00 (s, 1H), 7.89 (s, 1H), 7.59 (s, 1H), 7.54 (s, 1H), 7.23 (s, 1H), 4.60 (s, 2H), 3.73 (t, J=5.81 Hz, 2H), 2.88 (br t, J=5.70 Hz, 2H), 2.23 (s, 3H). LC-MS (ESI): m/z (M+1)=485.1; $t_R$=1.15 min (method 1)

Pharmacological Activity of the Compounds of the Invention

In Vitro Assays

Binding Assays

DDR1 and DDR2 binding assays were performed using Life Technologies LanthaScreen™ Europium Kinase Binding assay. The compounds were incubated with 5 nM DDR1 (Carna Biosciences) or 5 nM DDR2 (Life Technologies) for 1 hour at room temperature in white 384-well OptiPlate (PerkinElmer), containing 20 nM or 10 nM Kinase Tracer 178 respectively and 2 nM Europium labelled anti-GST antibody (Life Technologies) in assay buffer (50 mM HEPES pH 7.5, 10 mM MgCl2, 1 mM EGTA and 0.01% BRIJ35).

The ratio of fluorescence emission 665 nm/615 nm after excitation at 340 nm was obtained using the Tecan Spark 20M plate reader. IC50 values were determined in GraphPad Prism 7.0 software, using 4 parameter model: log(inhibitor) vs. response. IC50 values were converted in Ki using the Cheng-Prusoff equation (Ki=IC50/(1+[Tracer]/Kd).

DDR1 Cell Based Assay

The inhibition of DDR1 receptor activation by compounds was evaluated by PathHunter® U2OS DDR1 assay (Eurofins DiscoverX), according to the manufacturer's instructions. Briefly, U2OS-DDR1 cells were seeded in white 384-well plates at a density of 5000 cells/well and incubated for 2 hours at 37° C. and 5% $CO_2$. Cells were then treated with compounds at different concentrations and incubated for 30 minutes, before stimulation with bovine Type II Collagen 20 μg/ml and incubation overnight at 37° C. and 5% $CO_2$. PathHunter Detection Reagents were prepared according to the protocol provided by DiscoverX and 20 μl/well of this mix were added to each well. After incubating the plates for 1 hour at room temperature in the dark, luminescence signal was acquired with a plate reader. Raw data were normalized to vehicle control (0% for normalization) and positive control (100% for normalization; cells treated with 20 μg/ml collagen II) and IC50 parameters were calculated in GraphPad Prism 8.0 software, using sigmoidal dose-response curve fitting with variable slope.

DDR2 Cell Based Assay

The inhibition of DDR2 phosphorylation by compounds was evaluated in HEK293T-DDR2 recombinant cells by phospho-ELISA assay. Briefly, HEK293T-DDR2 cells were seeded in poly-D-lysine-coated 24-well plates at a density of 250,000 cells/well and incubated for 1.5 hours at 37° C. and 5% $CO_2$ in DMEM+10% FBS. After that, the medium was changed to serum-free DMEM and cells were incubated for 3 hours. Then, test compounds were added at different concentrations 30 minutes before stimulation with bovine Type II Collagen at 50 μg/ml for further 3 hours. For DDR2 phospho-ELISA assay (DuoSet IC Human Phospho-DDR2; R&D Systems), protein extracts were obtained by adding 60 μl/well of lysis buffer prepared according to the manufacturer's instructions. Protein concentration in the samples was determined by BCA assay and the levels of phospho-DDR2 were determined following R&D Systems indications. Raw data were normalized to maximal inhibition control (0% for normalization) and positive control (100% for normalization; cells treated with 20 μg/ml collagen II) and IC50 parameters were calculated in GraphPad Prism 8.0 software, using sigmoidal dose-response curve fitting with variable slope.

The results for individual compounds are provided below in Table 5, wherein the compounds are classified in term of potency (nM) in binding and cell based assay with respect to their inhibitory activity on DDR1 and DDR2:

TABLE 5

| Example No. | Ki DDR1 | Ki DDR2 | IC50 DDR1 | IC50DDR2 |
|---|---|---|---|---|
| 1 | +++ | ++ | + | − |
| 2 | ++ | + | + | − |
| 3 | +++ | +++ | ++ | − |
| 4 | +++ | +++ | +++ | +++ |
| 5 | +++ | +++ | ++ | +++ |
| 6 | +++ | +++ | ++ | − |
| 7 | +++ | +++ | +++ | − |
| 8 | +++ | +++ | + | − |
| 9 | +++ | +++ | + | − |
| 10 | +++ | +++ | +++ | − |
| 11 | +++ | +++ | + | − |
| 12 | +++ | +++ | ++ | − |
| 13 | +++ | +++ | + | − |
| 14 | +++ | +++ | +++ | − |
| 15 | +++ | +++ | ++ | − |
| 16 | +++ | +++ | +++ | +++ |
| 17 | +++ | ++ | ++ | − |
| 18 | +++ | +++ | +++ | +++ |
| 19 | +++ | +++ | ++ | − |
| 20 | +++ | +++ | ++ | − |
| 21 | +++ | +++ | +++ | − |
| 22 | +++ | +++ | + | − |
| 23 | +++ | +++ | ++ | − |
| 24 | +++ | +++ | ++ | − |
| 25 | +++ | +++ | ++ | − |
| 26 | +++ | ++ | ++ | − |
| 27 | +++ | +++ | +++ | − |
| 28 | +++ | +++ | +++ | − |
| 29 | +++ | +++ | + | − |
| 30 | +++ | +++ | + | − |
| 31 | +++ | +++ | ++ | ++ |
| 32 | +++ | +++ | +++ | − |
| 33 | +++ | +++ | ++ | − |
| 34 | +++ | +++ | ++ | − |
| 35 | +++ | ++ | + | − |
| 36 | +++ | +++ | +++ | − |
| 37 | +++ | +++ | ++ | − |
| 38 | +++ | +++ | +++ | +++ |
| 39 | +++ | +++ | ++ | ++ |
| 40 | +++ | +++ | +++ | − |
| 41 | +++ | +++ | + | − |
| 42 | +++ | +++ | +++ | +++ |
| 43 | +++ | +++ | +++ | − |
| 44 | +++ | +++ | ++ | − |
| 45 | +++ | +++ | +++ | +++ |
| 46 | +++ | +++ | +++ | +++ |
| 47 | +++ | +++ | + | − |
| 48 | +++ | +++ | +++ | − |
| 49 | +++ | +++ | +++ | − |
| 50 | +++ | +++ | ++ | − |

TABLE 5-continued

| Example No. | Ki DDR1 | Ki DDR2 | IC50 DDR1 | IC50DDR2 |
|---|---|---|---|---|
| 51 | +++ | ++ | + | – |
| 52 | +++ | +++ | + | – |
| 53 | +++ | +++ | ++ | – |
| 54 | +++ | +++ | ++ | – |
| 55 | +++ | +++ | ++ | – |
| 56 | +++ | ++ | ++ | – |
| 57 | +++ | ++ | ++ | – |
| 58 | +++ | +++ | ++ | ++ |
| 59 | +++ | +++ | +++ | – |
| 60 | +++ | +++ | +++ | – |
| 61 | +++ | +++ | +++ | – |
| 62 | +++ | +++ | +++ | – |
| 63 | +++ | +++ | +++ | +++ |
| 64 | +++ | +++ | +++ | +++ |
| 65 | +++ | +++ | ++ | – |

+: Ki between 50 and 80 nM
++: Ki between 25 and 50 nM
+++: Ki lower than 25 nM
+: IC50 between 50 and 80 nM
++: IC50 between 25 and 50 nM
+++: IC50 lower than 25 nM
–: not available As it can be appreciated, the compounds of Table 5, i.e. the compounds of the invention, show a good activity as antagonist of DDR1 and DDR2. Accordingly, the compounds of the invention can be effectively used for treating disease, disorder or condition associated with DDR receptors, such as fibrosis, e.g. pulmonary fibrosis, idiopathic pulmonary fibrosis (IPF), hepatic fibrosis, renal fibrosis, ocular fibrosis, cardiac fibrosis, arterial fibrosis and systemic sclerosis.

COMPARATIVE EXAMPLES

Compounds of the Examples C1 and C2 were tested in the same binding assay described above.

TABLE 6

| Example No | DDR1 Ki (nM) | DDR2 Ki (nM) |
|---|---|---|
| C1 | 238 | 172 |
| C2 | 29000 | 50000 |

The compounds of the present invention, as shown in Table 5, have both a binding affinity for DDR1 and DDR2 receptors expressed as Ki and an inhibitory potency expressed as IC50 against DDR1 and DDR2 receptors lower than 80 nM, and for most of the compounds lower than 50 nM or even lower than 25 nM. Conversely, comparative Example C1 has a binding affinity higher than 230 nM on DDR1 receptor, and higher than 170 nM on DDR2; and comparative Example C2 has a binding affinity of 29000 nM on DDR1 receptor, and of 50000 nM on DDR2.

These data demonstrate that, conversely to the comparative compound of Example C1 characterized by lacking a linker between the tetrahydrothieno pyridine ring and Hy group, the presence in the compound of Example 2 of the present invention of a —$CH_2$— linker in that position, unexpectedly and remarkably determines a relevant increase in the inhibitory activity on the DDR1 and DDR2 receptors.

As a further evidence, conversely to the compound of Example C2, characterized by the absence of a linker between the tetrahydrothieno pyridine ring and Hy group and by the —C(O)NH— group substitution at the α position with respect to sulphur atom, instead of the β position as in Example 2 of the present invention, the presence of the above mentioned linker concurrently with the substitution at the β position in the present invention compounds unexpectedly and noteworthy determines a relevant increase in the inhibitory activity against the DDR1 and DDR2 receptors.

The invention claimed is:

1. A compound of formula (I) or a pharmaceutically acceptable salt thereof:

(I)

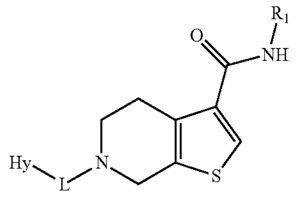

wherein:

L is selected from the group consisting of —C(O)— and —$CH_2$—;

Hy is a monocyclic heteroaryl optionally substituted with one or more groups selected from —($C_1$-$C_4$)alkyl, a halogen atom, cyano, —$(CH_2)_nNR_4R_5$, —NH-heterocycloalkyl, —O—($C_1$-$C_6$)alkyl, —($C_1$-$C_6$)haloalkyl, —C(O)NH—($C_1$-$C_6$)alkylene-$NR_4R_5$, —O—($C_1$-$C_6$)alkylene-cycloalkyl, —NHC(O)—($C_1$-$C_6$)alkyl, —NHC(O)—($C_1$-$C_6$)alkylene-$NR_4R_5$, —NHC(O)—($C_1$-$C_6$)alkylene-O—($C_1$-$C_4$)alkyl, —NH—($C_1$-$C_6$)alkylene-O—($C_1$-$C_4$)alkyl, —NH—($C_1$-$C_6$)alkylene-OH, -heteroaryl optionally substituted by one or more of —($C_1$-$C_4$)alkyl and —NH-heteroaryl, wherein the heteroaryl is optionally substituted by one or more —($C_1$-$C_4$)alkyl, and heterocycloalkyl optionally substituted by one or more groups selected from oxo and —($C_1$-$C_6$)alkyl;

$R_1$ is selected from the group consisting of:

Het which is an heteroaryl optionally substituted with one or more groups selected from —($C_1$-$C_4$)alkyl, —($C_1$-$C_4$)haloalkyl, and aryl, wherein the aryl is optionally substituted with one or more groups selected from —($C_1$-$C_4$)alkyl and a halogen atom; and

X (X)

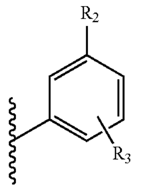

wherein:

$R_2$ is selected from the group consisting of —O($C_1$-$C_4$)haloalkyl, a halogen atom, —O($C_3$-$C_7$)cycloalkyl, and —($C_1$-$C_4$)haloalkyl; and $R_3$ is H or is selected from the group consisting of a halogen atom, cyano, —O($C_1$-$C_4$)alkyl, —O($C_1$-$C_4$)haloalkyl, heterocycloalkyl-($C_1$-$C_4$)alkylene-, —($C_1$-$C_4$)alkylene-heterocycloalkyl-$NR_4R_5$, and heteroaryl optionally substituted with one or more —($C_1$-$C_4$)alkyl, and wherein the heterocycloalkyl is optionally substituted with one or more —($C_1$-$C_4$) alkyl;

n is 0, 1 or 2;

$R_4$ is H or —($C_1$-$C_4$)alkyl; and $R_5$ is H or —($C_1$-$C_4$)alkyl.

2. The compound or pharmaceutically acceptable salt thereof according to claim 1, wherein the compound is represented by formula (Ia):

(Ia)

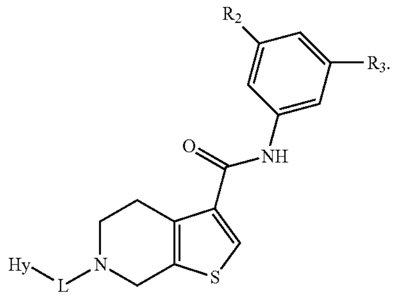

3. The compound or pharmaceutically acceptable salt thereof according to claim 2, wherein the compound is represented by formula (Iaa):

(Iaa)

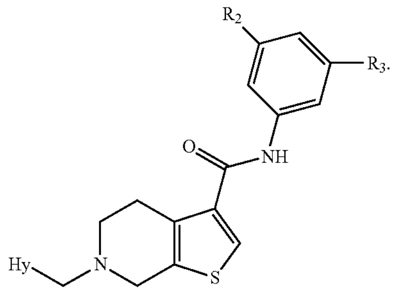

4. The compound or pharmaceutically acceptable salt thereof according to claim 1, wherein the compound is selected from the group consisting of:

N-(3-((4-methylpiperazin-1-yl)methyl)-5-(trifluoromethyl)phenyl)-6-(pyridin-3-ylmethyl)-4,5,6,7-tetrahydrothieno[2,3-c]pyridine-3-carboxamide;

N-(3-((4-methylpiperazin-1-yl)methyl)-5-(trifluoromethyl)phenyl)-6-(pyrimidin-5-ylmethyl)-4,5,6,7-tetrahydrothieno[2,3-c]pyridine-3-carboxamide;

N-(3-(4-methyl-1H-imidazol-1-yl)-5-(trifluoromethyl)phenyl)-6-(pyrimidin-5-ylmethyl)-4,5,6,7-tetrahydrothieno[2,3-c]pyridine-3-carboxamide;

N-(3-fluoro-5-(trifluoromethyl)phenyl)-6-(pyrimidin-5-ylmethyl)-4,5,6,7-tetrahydrothieno[2,3-c]pyridine-3-carboxamide;

6-(pyrimidin-5-ylmethyl)-N-(3-(trifluoromethyl)phenyl)-4,5,6,7-tetrahydrothieno[2,3-c]pyridine-3-carboxamide;

N-(3-fluoro-5-(trifluoromethoxy)phenyl)-6-(pyrimidin-5-ylmethyl)-4,5,6,7-tetrahydrothieno[2,3-c]pyridine-3-carboxamide;

N-(3-(1,1-difluoroethyl)phenyl)-6-(pyrimidin-5-ylmethyl)-4,5,6,7-tetrahydrothieno[2,3-c]pyridine-3-carboxamide;

N-(3-(difluoromethoxy)-5-fluorophenyl)-6-(pyrimidin-5-ylmethyl)-4,5,6,7-tetrahydrothieno[2,3-c]pyridine-3-carboxamide;

N-(3-(difluoromethoxy)phenyl)-6-(pyrimidin-5-ylmethyl)-4,5,6,7-tetrahydrothieno[2,3-c]pyridine-3-carboxamide;

N-(3-cyano-5-(trifluoromethyl)phenyl)-6-(pyrimidin-5-ylmethyl)-4,5,6,7-tetrahydrothieno[2,3-c]pyridine-3-carboxamide;

6-((4-(2-methoxyacetamido)pyridin-3-yl)methyl)-N-(3-(trifluoromethyl)phenyl)-4,5,6,7-tetrahydrothieno[2,3-c]pyridine-3-carboxamide;

6-((2-((1-methyl-1H-pyrazol-4-yl)amino)pyrimidin-5-yl)methyl)-N-(3-(trifluoromethyl)phenyl)-4,5,6,7-tetrahydrothieno[2,3-c]pyridine-3-carboxamide;

6-((5-cyanopyridin-3-yl)methyl)-N-(3-(trifluoromethyl)phenyl)-4,5,6,7-tetrahydrothieno[2,3-c]pyridine-3-carboxamide;

6-((5-chloropyridin-3-yl)methyl)-N-(3-(trifluoromethyl)phenyl)-4,5,6,7-tetrahydrothieno[2,3-c]pyridine-3-carboxamide;

6-((5-methoxypyridin-3-yl)methyl)-N-(3-(trifluoromethyl)phenyl)-4,5,6,7-tetrahydrothieno[2,3-c]pyridine-3-carboxamide;

6-((5-methylpyridin-3-yl)methyl)-N-(3-(trifluoromethyl)phenyl)-4,5,6,7-tetrahydrothieno[2,3-c]pyridine-3-carboxamide;

N-(3-(trifluoromethyl)phenyl)-6-((5-(trifluoromethyl)pyridin-3-yl)methyl)-4,5,6,7-tetrahydrothieno[2,3-c]pyridine-3-carboxamide;

6-((5-fluoropyridin-3-yl)methyl)-N-(3-(trifluoromethyl)phenyl)-4,5,6,7-tetrahydrothieno[2,3-c]pyridine-3-carboxamide;

6-(pyridin-3-ylmethyl)-N-(3-(trifluoromethyl)phenyl)-4,5,6,7-tetrahydrothieno[2,3-c]pyridine-3-carboxamide;

6-((3-aminopyrazin-2-yl)methyl)-N-(3-(trifluoromethyl)phenyl)-4,5,6,7-tetrahydrothieno[2,3-c]pyridine-3-carboxamide;

6-((2-aminopyrimidin-5-yl)methyl)-N-(3-(trifluoromethyl)phenyl)-4,5,6,7-tetrahydrothieno[2,3-c]pyridine-3-carboxamide;

6-((5-(4-methyl-3-oxopiperazin-1-yl) pyridin-3-yl)methyl)-N-(3-(trifluoromethyl)phenyl)-4,5,6,7-tetrahydrothieno[2,3-c]pyridine-3-carboxamide;

6-((5-(1,1-dioxidothiomorpholino)pyridin-3-yl)methyl)-N-(3-(trifluoromethyl)phenyl)-4,5,6,7-tetrahydrothieno[2,3-c]pyridine-3-carboxamide;

6-((5-(2-(dimethylamino) acetamido)pyridin-3-yl)methyl)-N-(3-(trifluoromethyl)phenyl)-4,5,6,7-tetrahydrothieno[2,3-c]pyridine-3-carboxamide;

N-(3-fluoro-5-(trifluoromethyl)phenyl)-6-((2-(oxetan-3-ylamino)pyrimidin-5-yl)methyl)-4,5,6,7-tetrahydrothieno[2,3-c]pyridine-3-carboxamide;

6-((2-aminopyrimidin-5-yl)methyl)-N-(3-fluoro-5-(trifluoromethyl)phenyl)-4,5,6,7-tetrahydrothieno[2,3-c]pyridine-3-carboxamide;

6-((2-acetamidopyrimidin-5-yl)methyl)-N-(3-fluoro-5-(trifluoromethyl)phenyl)-4,5,6,7-tetrahydrothieno[2,3-c]pyridine-3-carboxamide;

N-(3-fluoro-5-(trifluoromethyl)phenyl)-6-((2-(methylamino)pyrimidin-5-yl)methyl)-4,5,6,7-tetrahydrothieno[2,3-c]pyridine-3-carboxamide;

N-(3-fluoro-5-(trifluoromethyl)phenyl)-6-((2-((2-methoxyethyl)amino)pyrimidin-5-yl)methyl)-4,5,6,7-tetrahydrothieno[2,3-c]pyridine-3-carboxamide;

6-((6-acetamidopyridin-3-yl)methyl)-N-(3-fluoro-5-(trifluoromethyl)phenyl)-4,5,6,7-tetrahydrothieno[2,3-c]pyridine-3-carboxamide;

6-((2-aminopyridin-3-yl)methyl)-N-(3-fluoro-5-(trifluoromethyl)phenyl)-4,5,6,7-tetrahydrothieno[2,3-c]pyridine-3-carboxamide;

N-(3-fluoro-5-(trifluoromethyl)phenyl)-6-((2-((2-hydroxyethyl)amino)pyrimidin-5-yl)methyl)-4,5,6,7-tetrahydrothieno[2,3-c]pyridine-3-carboxamide;

6-((4-aminopyrimidin-5-yl)methyl)-N-(3-fluoro-5-(trifluoromethyl)phenyl)-4,5,6,7-tetrahydrothieno[2,3-c]pyridine-3-carboxamide;

6-((3-aminopyrazin-2-yl)methyl)-N-(3-fluoro-5-(trifluoromethyl)phenyl)-4,5,6,7-tetrahydrothieno[2,3-c]pyridine-3-carboxamide;

6-((2-amino-4-methylpyrimidin-5-yl)methyl)-N-(3-fluoro-5-(trifluoromethyl)phenyl)-4,5,6,7-tetrahydrothieno[2,3-c]pyridine-3-carboxamide;

N-(3-fluoro-5-(trifluoromethyl)phenyl)-6-((6-(methylamino)pyridin-3-yl)methyl)-4,5,6,7-tetrahydrothieno[2,3-c]pyridine-3-carboxamide;

(R)-6-((2-aminopyrimidin-5-yl)methyl)-N-(3-((3-(dimethylamino) pyrrolidin-1-yl)methyl)-5-(trifluoromethyl)phenyl)-4,5,6,7-tetrahydrothieno[2,3-c]pyridine-3-carboxamide;

(R)—N-(3-((3-(dimethylamino) pyrrolidin-1-yl)methyl)-5-(trifluoromethyl)phenyl)-6-((4-(2-fluoropropan-2-yl) pyrimidin-5-yl)methyl)-4,5,6,7-tetrahydrothieno[2,3-c]pyridine-3-carboxamide;

(R)—N-(3-((3-(dimethylamino) pyrrolidin-1-yl)methyl)-5-(trifluoromethyl)phenyl)-6-((4-methoxypyrimidin-5-yl)methyl)-4,5,6,7-tetrahydrothieno[2,3-c]pyridine-3-carboxamide;

(R)-6-((4-cyclopropoxypyrimidin-5-yl)methyl)-N-(3-((3-(dimethylamino) pyrrolidin-1-yl)methyl)-5-(trifluoromethyl)phenyl)-4,5,6,7-tetrahydrothieno[2,3-c]pyridine-3-carboxamide;

(R)—N-(3-((3-(dimethylamino) pyrrolidin-1-yl)methyl)-5-(trifluoromethyl)phenyl)-6-((5-(1-methyl-1H-pyrazol-4-yl) pyridin-3-yl)methyl)-4,5,6,7-tetrahydrothieno[2,3-c]pyridine-3-carboxamide;

6-((2-aminopyrimidin-5-yl)methyl)-N-(3-((dimethylamino)methyl)-5-(trifluoromethyl)phenyl)-4,5,6,7-tetrahydrothieno[2,3-c]pyridine-3-carboxamide;

6-((2-aminopyrimidin-5-yl)methyl)-N-(3-(1,1-difluoroethyl)phenyl)-4,5,6,7-tetrahydrothieno[2,3-c]pyridine-3-carboxamide; and 6-((2-aminopyrimidin-5-yl)methyl)-N-(3-cyano-5-(trifluoromethyl)phenyl)-4,5,6,7-tetrahydrothieno[2,3-c]pyridine-3-carboxamide.

5. The compound or pharmaceutically acceptable salt thereof according to claim 1, wherein the compound is represented by formula (Iaa'):

(Iaa')

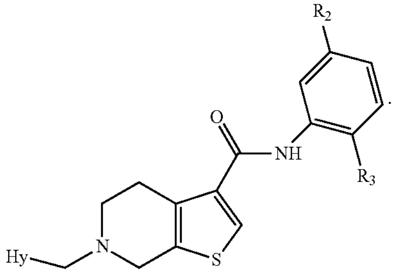

6. The compound or pharmaceutically acceptable salt thereof according to claim 1, wherein the compound is represented by formula (Iaa")

(Iaa")

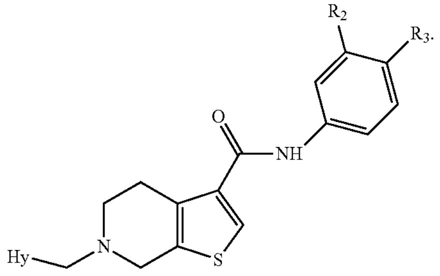

7. The compound or pharmaceutically acceptable salt thereof according to claim 2, wherein the compound is represented by formula (Iab):

(Iab)

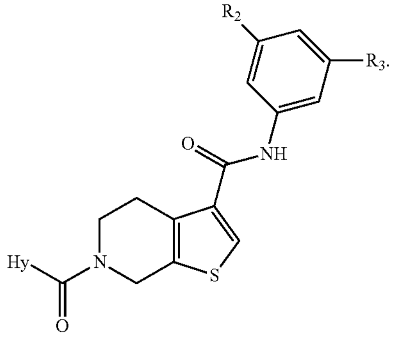

8. The compound or pharmaceutically acceptable salt thereof according to claim 1, wherein the compound is represented by formula (Ib):

(Ib)

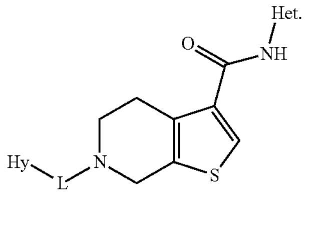

9. The compound or pharmaceutically acceptable salt thereof according to claim 8, wherein the compound is represented by formula (Iba):

(Iba)

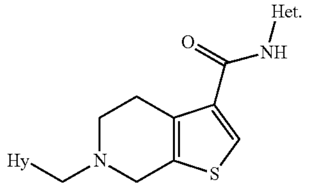

10. A pharmaceutical composition comprising the compound or pharmaceutically acceptable salt thereof according to claim 1, in admixture with one or more pharmaceutically acceptable carriers or excipients.

11. The pharmaceutical composition according to claim 10 formulated for administration by inhalation.

12. A method for treating a disease, disorder, or condition associated with dysregulation of Discoidin Domain Receptor, comprising administering the compound or pharmaceutically acceptable salt thereof according to claim 1 to subject in need of such treatment.

13. A method for treating at least one selected from fibrosis and a disease, disorder, or condition involving fibrosis comprising administering the compound or pharmaceutically acceptable salt thereof according to claim 1 to a subject in need of such treatment.

14. A method for treating at least one selected from pulmonary fibrosis, idiopathic pulmonary fibrosis (IPF), hepatic fibrosis, renal fibrosis, ocular fibrosis, cardiac fibrosis, arterial fibrosis, and systemic sclerosis, comprising administering the compound or pharmaceutically acceptable salt thereof according to claim 1 to a subject in need of such treatment.

15. A method for treating idiopathic pulmonary fibrosis (IPF), comprising administering the compound or pharmaceutically acceptable salt thereof according to claim 1 to a subject in need of such treatment.

* * * * *